US011149233B2

(12) United States Patent
Barrientos et al.

(10) Patent No.: US 11,149,233 B2
(45) Date of Patent: Oct. 19, 2021

(54) POLYPEPTIDES HAVING RNASE ACTIVITY

(71) Applicant: Novozymes A/S, Bagsvaerd (DK)

(72) Inventors: Fabian Barrientos, Birkerod (DK);
Morten Gjermansen, Greve (DK);
Klaus Gori, Dyssegaard (DK);
Henriette Draborg, Frederikssund
(DK); Mary Ann Stringer, Soborg
(DK); Dorotea Raventos Segura,
Rungsted (DK); **Marc Dominique
Morant**, Frederiksburg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/495,161

(22) PCT Filed: Mar. 27, 2018

(86) PCT No.: PCT/EP2018/057746
§ 371 (c)(1),
(2) Date: Sep. 18, 2019

(87) PCT Pub. No.: WO2018/178061
PCT Pub. Date: Oct. 4, 2018

(65) Prior Publication Data
US 2020/0308510 A1 Oct. 1, 2020

(30) Foreign Application Priority Data

Mar. 31, 2017 (EP) ..................... 17164342

(51) Int. Cl.
*C11D 3/386* (2006.01)
*C12N 9/22* (2006.01)

(52) U.S. Cl.
CPC ............ *C11D 3/38636* (2013.01); *C12N 9/22* (2013.01); *C12Y 301/27* (2013.01)

(58) Field of Classification Search
None
See application file for complete search history.

(56) References Cited

U.S. PATENT DOCUMENTS

2005/0079594 A1    4/2005  Marion
2016/0319225 A1*  11/2016  Lant .................... C11D 11/0017

FOREIGN PATENT DOCUMENTS

| EP | 3088505 A1 | 11/2016 |
| WO | 2004041988 A1 | 5/2004 |
| WO | 2006031554 A2 | 3/2006 |
| WO | 2008153805 A2 | 12/2008 |
| WO | 2015/155351 A1 | 10/2015 |

OTHER PUBLICATIONS

RefSeq submission WP_068853055 submitted on Nov. 2, 2016 by Wei, Y. et al. to EMBL/GenBank/DDBJ databases, (copy of sequence alignment in Office action) in Score USPTO sequence database with application folder. (Year: 2016).*
Dastager et al., 2017, EBI accession No. A0A231QZM6.
Liu et al, 2016, EBI Accession No. A0A1B8WEL8.
Yuki et al, 2014, EBI accession No. W7YUP7.

* cited by examiner

*Primary Examiner* — Anand U Desai
(74) *Attorney, Agent, or Firm* — Elias Lambiris

(57) ABSTRACT

The present invention relates to polypeptides having RNase activity and polynucleotides encoding the polypeptides. The invention also relates to nucleic acid constructs, vectors, and host cells comprising the polynucleotides as well as methods of producing and using the polypeptides.

18 Claims, 1 Drawing Sheet
Specification includes a Sequence Listing.

```
                                                                    10                  20
SEQ ID NO 3  Paenibacillus sp-18057                 ....................GCGQIGVDSPQGIASHSAEAP
SEQ ID NO 6  Paenibacillus sp-62770                 ........................LTVDD............
SEQ ID NO 9  Amycolatopsis azurea (DSM43854)        ......................FVKDGISGDDTKSSSAP
SEQ ID NO 12 Environmental bacterial community E    CSILDINYDGPEMPKLEEPSEGEIPNDEIPDIEIPEDEIP
SEQ ID NO 15 Acromonium alcalophilum                ....................APSGQLEKRATTCGSTY 30        40        50        60
SEQ ID NO 3  Paenibacillus sp-18057                 .GTQDVSRQAPLTGFKEVADYIRSYGALPDNFITKKEAER
SEQ ID NO 6  Paenibacillus sp-62770                 ....STQTQAVLNQFDEVANYLAEHQELPDNYITKKEARA
SEQ ID NO 9  Amycolatopsis azurea (DSM43854)        .ASSSAQPKPSGAAKGKVAGEESGLPVKPLTGLPSQASDT
SEQ ID NO 12 Environmental bacterial community E    EGESLIIEDGQYTRKDEVAEYIHIFGRLPENYITKNEAMD
SEQ ID NO 15 Acromonium alcalophilum                YSTSQVSAAASAACNHVRAGTRAGSSTYPHAY...NNYEG 70        80        90       100
SEQ ID NO 3  Paenibacillus sp-18057                 LGWVPSEGNLGKVAPGKSIGGDRFGNREGLLPKEKNRIWY
SEQ ID NO 6  Paenibacillus sp-62770                 LGWEPSEGNLQDVAPGKSIGGDIFQNREGLLPKKKGRTWY
SEQ ID NO 9  Amycolatopsis azurea (DSM43854)        ..WKLITA..GGPYPYPRNDDVTFQNREKVLPAKDSGYYR
SEQ ID NO 12 Environmental bacterial community E    LGWDASSGNLWDVTDEMSIGGDRFGNREGLLPEASGRKWY
SEQ ID NO 15 Acromonium alcalophilum                FNF.PISC......PYQ.........LFPLRTSGV..

110       120       130
SEQ ID NO 3  Paenibacillus sp-18057                 EADINYE.....GGTRGADRIVFSND.....GLIYMTDH
SEQ ID NO 6  Paenibacillus sp-62770                 EADINYS.....GGTRGSDRILYSSD.....GLIYKTDH
SEQ ID NO 9  Amycolatopsis azurea (DSM43854)        E....YTVKTPGSPDRGARRLVTGTG.....KELYYTDH
SEQ ID NO 12 Environmental bacterial community E    EADIDYE.....GGRRNAKRIVFSDD.....GLIYYDDH
SEQ ID NO 15 Acromonium alcalophilum                .....YT.....GGAPGPDRVIINRNTCAIACQITHIGAP 140
SEQ ID NO 3  Paenibacillus sp-18057                 YRSFTDITEGGPDP
SEQ ID NO 6  Paenibacillus sp-62770                 YRTFEQIK......
SEQ ID NO 9  Amycolatopsis azurea (DSM43854)        YKSFVVVD...PSR
SEQ ID NO 12 Environmental bacterial community E    YASFEKLY......
SEQ ID NO 15 Acromonium alcalophilum                GNAFVGCS...GTY
```

POLYPEPTIDES HAVING RNASE ACTIVITY

CROSS-REFERENCE TO RELATED APPLICATIONS

This application is a 35 U.S.C. 371 national application of international application no. PCT/EP2018/057746 filed Mar. 27, 2018 which claims priority or the benefit under 35 U.S.C. 119 of European application no. EP 17164342.2 filed Mar. 31, 2017, the contents of which are fully incorporated herein by reference.

REFERENCE TO A SEQUENCE LISTING

This application contains a Sequence Listing in computer readable form, which is incorporated herein by reference. The name of the file containing the Sequence Listing is SQ.txt, which was created on Feb. 19, 2020 and has 125 KB.

BACKGROUND OF THE INVENTION

Field of the Invention

The present invention relates to polypeptides having RNase activity and polynucleotides encoding the polypeptides. The invention also relates to nucleic acid constructs, vectors, and host cells comprising the polynucleotides as well as methods of producing and using the polypeptides.

Description of the Related Art

Compositions comprising enzyme mixtures including RNases are described in WO 2004/0441988 (Marion Karine). The compositions are useful for removal of biofilm in the medical field, such as on analytical instruments and other equipment. WO 2006/031554 (Novozymes) describes methods for preventing, removing, reducing or disrupting biofilm on a surface. The methods disclosed use alpha-amylases, which may be combined with other enzymes including RNases. However, no specific RNase and no effect of the use of RNase is disclosed. Similar disclosure may be found e.g. in WO 2008/153805 (Danisco US). The use in cleaning processes of RNases for removal of RNA staining on fabrics is not described in the prior art. The present invention provides novel RNases particularly suitable for reduction or removal of RNase soiling comprised in organic matter such as biofilm from a fabric, e.g. textiles.

SUMMARY OF THE INVENTION

The present invention relates to nucleases, in particular ribonucleases, methods and the use of polypeptides having RNase activity and compositions comprising polypeptides having RNase activity.

One aspect of the invention relates to a polypeptide having RNase activity, selected from the group consisting of:
  (a) a polypeptide having at least 80% sequence identity to the polypeptide of SEQ ID NO: 3;
  (b) a polypeptide having at least 80% sequence identity to the polypeptide of SEQ ID NO: 6;
  (c) a polypeptide having at least 80% sequence identity to the polypeptide of SEQ ID NO: 9;
  (d) a polypeptide having at least 80% sequence identity to the polypeptide of SEQ ID NO: 12;
  (e) a polypeptide having at least 80% sequence identity to the polypeptide of SEQ ID NO: 15;
  (f) a polypeptide having at least 80% sequence identity to the polypeptide of SEQ ID NO: 57;
  (g) a polypeptide having at least 80% sequence identity to the polypeptide of SEQ ID NO: 58;
  (h) a polypeptide having at least 80% sequence identity to the polypeptide of SEQ ID NO: 59;
  (i) a polypeptide having at least 80% sequence identity to the polypeptide of SEQ ID NO: 60;
  (j) a polypeptide having at least 80% sequence identity to the polypeptide of SEQ ID NO: 61;
  (k) a polypeptide having at least 80% sequence identity to the polypeptide of SEQ ID NO: 62;
  (l) a polypeptide having at least 80% sequence identity to the polypeptide of SEQ ID NO: 63;
  (m) a polypeptide having at least 80% sequence identity to the polypeptide of SEQ ID NO: 64;
  (n) a polypeptide having at least 80% sequence identity to the polypeptide of SEQ ID NO: 65;
  (o) a polypeptide having at least 80% sequence identity to the polypeptide of SEQ ID NO: 66;
  (p) a polypeptide having at least 80% sequence identity to the polypeptide of SEQ ID NO: 67;
  (q) a polypeptide having at least 80% sequence identity to the polypeptide of SEQ ID NO: 72;
  (r) a polypeptide having at least 80% sequence identity to the polypeptide of SEQ ID NO: 73;
  (s) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 72 and SEQ ID NO: 73, wherein the variant has RNase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
  (t) a polypeptide comprising the polypeptide of (a), (b), (c), (d), (e), (f), (g), (h), (i), (j), (k), (l), (m), (n), (o), (p), (q), (r) or (s) and an N-terminal and/or C-terminal His-tag and/or HQ-tag;
  (u) a polypeptide comprising the polypeptide of (a), (b), (c), (d), (e), (f), (g), (h), (i), (j), (k), (l), (m), (n), (o), (p), (q), (r) or (s) and an N-terminal and/or C-terminal extension of between 1 and 10 amino acids;
  (v) a fragment of the polypeptide of (a), (b), (c), (d), (e), (f), (g), (h), (i), (j), (k), (l), (m), (n), (o), (p), (q), (r) or (s) having RNase activity and having at least 90% of the length of the mature polypeptide;
  (w) a polypeptide comprising one or more of the motif(s) EYTV (SEQ ID NO: 28), [YRF]E[AYFWC]D (SEQ ID NO: 29), IGGD (SEQ ID NO: 30), YPH (SEQ ID NO: 31), HTGA (SEQ ID NO: 32) or DRV (SEQ ID NO:33); and
  (x) a polypeptide comprising one or more of the motifs YXEYTVXTPXXXXRGXRR (SEQ ID NO: 78), [WY][YRF]E[AYFWC]D[IV] (SEQ ID NO: 79), GXXIGGDXFXN (SEQ ID NO: 80), YPHX[YFA]X[ND]XE (SEQ ID NO: 81), PGXDRV (SEQ ID NO: 82) or THTGA[SR]G (SEQ ID NO: 83).

One aspect of the invention relates to a polynucleotide encoding a polypeptide of the invention. One aspect relates to a nucleic acid construct or an expression vector comprising a polynucleotide encoding a polypeptide of the invention wherein the polynucleotide is operably linked to one or more control sequences that direct the production of the polypeptide in an expression host. One aspect of the invention relates to a recombinant host cell comprising a polynucleotide encoding a polypeptide of the invention operably linked to one or more control sequences that direct the production of the polypeptide.

One aspect of the invention relates to a method of producing the polypeptide of the invention, comprising cultivating a cell, which in its wild-type form produces the polypeptide, under conditions conducive for production of the polypeptide.

One aspect relates to the use of a polypeptide comprising one or more of the motif(s) EYTV (SEQ ID NO: 28), [YRF]E[AYFWC]D (SEQ ID NO: 29), IGGD (SEQ ID NO: 30), YPH (SEQ ID NO: 31), HTGA (SEQ ID NO: 32) or DRV (SEQ ID NO: 33) and having RNase activity for deep cleaning of an item, wherein the item is a textile. One embodiment of this aspect relates to use of a polypeptide comprising one or more of the motifs YXEYTVXTPXXXXRGXRR (SEQ ID NO: 78), [WY][YRF]E[AYFWC]D[IV] (SEQ ID NO: 79), GXXIGGDXFXN (SEQ ID NO: 80), YPHX[YFA]X[ND]XE (SEQ ID NO: 81), PGXDRV (SEQ ID NO: 82) and THTGA[SR]G (SEQ ID NO: 83) and having RNase activity for deep cleaning of an item, wherein the item is a textile.

One aspect of relates to the use of a polypeptide having RNase activity,
(i) for preventing, reducing or removing stickiness of an item;
(ii) for pretreating stains on an item;
(iii) for preventing, reducing or removing redeposition of soil during a wash cycle;
(iv) for preventing, reducing or removing adherence of soil to an item;
(v) for maintaining or improving whiteness of an item;
(vi) for preventing, reducing or removal malodor from an item;
wherein the item is a textile.

One aspect relates to a laundering method for laundering an item comprising the steps of:
a. exposing an item to a wash liquor comprising a polypeptide of the invention or a cleaning composition comprising a polypeptide of the invention;
b. completing at least one wash cycle; and
c. optionally rinsing the item,
wherein the item is a textile.

Overview of Sequences

SEQ ID NO 1 DNA encoding full length polypeptide from *Paenibacillus* sp-18057
SEQ ID NO 2 polypeptide derived from SEQ ID NO 1
SEQ ID NO 3 mature polypeptide obtained from *Paenibacillus* sp-18057
SEQ ID NO 4 DNA encoding full length polypeptide from *Paenibacillus* sp-62770
SEQ ID NO 5 polypeptide derived from SEQ ID NO 4
SEQ ID NO 6 mature polypeptide obtained from *Paenibacillus* sp-62770
SEQ ID NO 7 DNA encoding full length polypeptide from *Amycolatopsis* azurea
SEQ ID NO 8 polypeptide derived from SEQ ID NO 7
SEQ ID NO 9 mature polypeptide obtained from *Amycolatopsis* azurea
SEQ ID NO 10 DNA encoding full length polypeptide from Environmental sample community E
SEQ ID NO 11 polypeptide derived from SEQ ID NO 10
SEQ ID NO 12 mature polypeptide obtained from Environmental sample communityE
SEQ ID NO 13 DNA encoding full length polypeptide from *Acremonium alcalophilum*
SEQ ID NO 14 polypeptide derived from SEQ ID NO 13
SEQ ID NO 15 mature polypeptide obtained from *Acremonium alcalophilum*
SEQ ID NO 16 DNA sequence of Environmental sample communityE
SEQ ID NO 17 polypeptide derived from SEQ ID NO 16
SEQ ID NO 18 DNA sequence of *Paenibacillus* sp-62770 with the inhibitor
SEQ ID NO 19 polypeptide derived from SEQ ID NO 18
SEQ ID NO 20 DNA sequence of *Paenibacillus* sp-18057 with the inhibitor
SEQ ID NO 21 polypeptide derived from SEQ ID NO 20
SEQ ID NO 22 DNA sequence of *Amycolatopsis* azurea with the inhibitor
SEQ ID NO 23 polypeptide derived from SEQ ID NO 22
SEQ ID NO 24 *Bacillus clausii* secretion signal
SEQ ID NO 25 His-tag
SEQ ID NO 26 Forward cloning primer Alca166-F
SEQ ID NO 27 Reverse cloning primer Alca166-R
SEQ ID NO 28 EYTV motif
SEQ ID NO 29 [YRF]E[AYFWC]D motif
SEQ ID NO 30 IGGD motif
SEQ ID NO 31 YPH motif
SEQ ID NO 32 HTGA motif
SEQ ID NO 33 DRV motif
SEQ ID NO 34 *Bacillus amyloliquefaciens* ribonuclease Barnase
SEQ ID NO 35 is a DNA sequence of *Stenotrophomonas rhizophila* with the inhibitor.
SEQ ID NO 36 is the polypeptide derived from SEQ ID NO 35, where the signal peptide is amino acids −20 to −1 and the mature polypeptide is amino acids 1-139.
SEQ ID NO 37 is a DNA sequence of *Erwinia persicina* with the inhibitor.
SEQ ID NO 38 is the polypeptide derived from SEQ ID NO 37, where the signal peptide is amino acids −20 to −1 and the mature polypeptide is amino acids 1-136.
SEQ ID NO 39 is a DNA sequence of *Paenibacillus tundrae* with the inhibitor.
SEQ ID NO 40 is the polypeptide derived from SEQ ID NO 39, where the signal peptide is amino acids −26 to −1 and the mature polypeptide is amino acids 1-119.
SEQ ID NO 41 is a DNA sequence of *Saccharothrix* sp-62935 with the inhibitor.
SEQ ID NO 42 polypeptide derived from SEQ ID NO 41, where the signal peptide is amino acids −26 to −1 and the mature polypeptide is amino acids 1-117.
SEQ ID NO 43 is a DNA sequence of *Saccharopolyspora endophytica* with the inhibitor.
SEQ ID NO 44 is the polypeptide derived from SEQ ID NO 43, where the signal peptide is amino acids −29 to −1 and the mature polypeptide is amino acids 1-108.
SEQ ID NO 45 is a DNA sequence of *Amycolatopsis circi* with the inhibitor.
SEQ ID NO 46 is the polypeptide derived from SEQ ID NO 45, where the signal peptide is amino acids −30 to −1 and the mature polypeptide is amino acids 1-120.
SEQ ID NO 47 is a DNA sequence of *Paenibacillus* sp-62770 with the inhibitor.
SEQ ID NO 48 is the polypeptide derived from SEQ ID NO 47, where the signal peptide is amino acids −26 to −1 and the mature polypeptide is amino acids 1-119.

SEQ ID NO 49 is a DNA sequence of *Paenibacillus* sp-18006 with the inhibitor.
SEQ ID NO 50 is the polypeptide derived from SEQ ID NO 49, where the signal peptide is amino acids −27 to −1 and the mature polypeptide is amino acids 1-117.
SEQ ID NO 51 is a DNA sequence of *Paenibacillus* sp-62724 with the inhibitor.
SEQ ID NO 52 is the polypeptide derived from SEQ ID NO 51, where the signal peptide is amino acids −34 to −1 and the mature polypeptide is amino acids 1-156.
SEQ ID NO 53 is a DNA sequence of *Alkalimonas* sp-62516 with the inhibitor.
SEQ ID NO 54 is the polypeptide derived from SEQ ID NO 54, where the signal peptide is amino acids −23 to −1 and the mature polypeptide is amino acids 1-115.
SEQ ID NO 55 is a DNA sequence of *Nonomuraea dietziae* with the inhibitor.
SEQ ID NO 56 is the polypeptide derived from SEQ ID NO 55, where the signal peptide is amino acids −27 to −1 and the mature polypeptide is amino acids 1-108.
SEQ ID NO 57 is the mature polypeptide obtained from *Stenotrophomonas rhizophila*.
SEQ ID NO 58 is the mature polypeptide obtained from *Erwinia persicina*.
SEQ ID NO 59 is the mature polypeptide obtained from *Paenibacillus tundrae*.
SEQ ID NO 60 is the mature polypeptide obtained from *Saccharothrix* sp-62935.
SEQ ID NO 61 is the mature polypeptide obtained from *Saccharopolyspora endophytica*.
SEQ ID NO 62 is the mature polypeptide obtained from *Amycolatopsis circi*.
SEQ ID NO 63 is the mature polypeptide obtained from *Paenibacillus* sp-62770 (DNA SEQ ID NO 47).
SEQ ID NO 64 is the mature polypeptide obtained from *Paenibacillus* sp-18006.
SEQ ID NO 65 is the mature polypeptide obtained from *Paenibacillus* sp-62724.
SEQ ID NO 66 is the mature polypeptide obtained from *Alkalimonas* sp-62516.
SEQ ID NO 67 is the mature polypeptide obtained from *Nonomuraea dietziae*.
SEQ ID NO 68 is a DNA sequence of *Trichoderma harzianum*.
SEQ ID NO 69 is the polypeptide derived from SEQ ID NO 68 with the signal peptide and mature polypeptide.
SEQ ID NO 70 is a DNA sequence of *Fusarium solani*.
SEQ ID NO 71 is the polypeptide derived from SEQ ID NO 70 with the signal peptide and the mature polypeptide.
SEQ ID NO 72 is the mature polypeptide derived from *Trichoderma harzianum*.
SEQ ID NO 73 is the mature polypeptide derived from *Fusarium solani*.
SEQ ID NO 74 Forward cloning primer MDQM1692-F
SEQ ID NO 75 Reverse cloning primer MDQM1692-R
SEQ ID NO 76 RNAse from *Streptomyces aureofaciens* (public sequence SWISSPROT:P30289)
SEQ ID NO 77 RNAse from *Gibberella fujikuroi* (public sequence SWISSPROT:A7M7A2)
SEQ ID NO 78 YXEYTVXTPXXXXRGXRR motif
SEQ ID NO 79 [WY][YRF]E[AYFWC]D[IV] motif
SEQ ID NO 80 GXXIGGDXFXN motif
SEQ ID NO 81 YPHX[YFA]X[ND]XE motif
SEQ ID NO 82 PGXDRV motif
SEQ ID NO 83 THTGA[SR]G motif Definitions The term "RNase" is an abbreviation of the term ribonuclease, which means a nuclease having RNase activity (EC 3.1.2.7) that catalyzes the degradation of RNA into smaller components. Ribonucleases can be divided into endoribonucleases and exoribonucleases; the present invention relates to e.g. endoribonucleases. For purposes of the present invention, RNase activity is determined according to the procedure described in the Examples. In one aspect, the polypeptides of the present invention have at least 20%, e.g., at least 40%, at least 50%, at least 60%, at least 70%, at least 80%, at least 90%, at least 95%, or at least 100% of the RNase activity of the any of the mature polypeptides shown in SEQ ID NO: 3, 6, 9, 12 or 15.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "biofilm" means a film produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry biofilm producing bacteria can be found among species including *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. On hard surfaces biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, *Staphylococcus aureus* and *Stenotrophomonas* sp.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" means a polynucleotide which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

The term "deep cleaning" means in this context disruption, reduction or removal of organic components such as polysaccharides, proteins, RNA, DNA, soil or other components present in organic matter such as biofilm.

The term "detergent adjunct ingredient" refers to ingredients different from the RNases of this invention. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aids, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, antifoaming agents, dispersants, processing aids, and/or pigments.

The term "detergent composition" refers to compositions that find use in the removal of undesired compounds from items to be cleaned, such as textiles. The terms "detergent compositions" and "cleaning compositions" are used interchangeably in the present application. The detergent composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and include, but are not limited to, detergent compositions such as liquid and/or solid laundry detergents and fine fabric detergents; fabric fresheners; fabric softeners; and textile and laundry pre-spotters/pretreatment. In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach systems or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "expression" includes any step involved in the production of a polypeptide including, but not limited to, transcription, post-transcriptional modification, translation, post-translational modification, and secretion.

The term "expression vector" means a linear or circular DNA molecule that comprises a polynucleotide encoding a polypeptide and is operably linked to control sequences that provide for its expression.

A "His-tag" refers to a polyhistidine tag typically comprising at least 6 histidine residues, that may be added to the N- or C-terminal. His-tags are known in the art for use in e.g. protein purification, but may also be used for improving solubility at low pH values. Similarly, an "HQ-tag", i.e. a histidine-glutamine tag, may also be used for the purpose of purification as is known in the art.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication. The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

By the term "malodor" is meant an odor which is not desired on clean items. The cleaned item should smell fresh and clean without malodors adhered to the item. One example of malodor is compounds with an unpleasant smell which may be produced by microorganisms and trapped within a biofilm or stick to the "glue" of a biofilm. Other examples of unpleasant smells are sweat or body odor adhered to an item which has been in contact with a human or animal. Other examples of malodor are odors from spices which stick to items, for example curry or other exotic spices with a strong smell.

The term "mature polypeptide" means a polypeptide in its final form following translation and any post-translational modifications, such as N-terminal processing, C-terminal truncation, glycosylation, phosphorylation, etc.

In one aspect, the mature polypeptide is amino acids 1 to 144 of SEQ ID NO: 2. Amino acids −29 to −1 of SEQ ID NO: 2 is the signal peptide.

In one aspect, the mature polypeptide is amino acids 1 to 119 of SEQ ID NO: 5. Amino acids −26 to −1 of SEQ ID NO: 5 is the signal peptide.

In one aspect, the mature polypeptide is amino acids 1 to 134 of SEQ ID NO: 8. Amino acids −22 to −1 of SEQ ID NO: 8 is the signal peptide.

In one aspect, the mature polypeptide is amino acids 1 to 158 of SEQ ID NO: 11. Amino acids −24 to −1 of SEQ ID NO: 11 is the signal peptide.

In one aspect, the mature polypeptide is amino acids 1 to 114 of SEQ ID NO: 14. Amino acids −17 to −1 of SEQ ID NO: 14 is the signal peptide.

In one aspect, the mature polypeptide is amino acids 1 to 139 of SEQ ID NO: 36. Amino acids −20 to −1 of SEQ ID NO: 36 is the signal peptide.

In one aspect, the mature polypeptide is amino acids 1 to 136 of SEQ ID NO: 38. Amino acids −20 to −1 of SEQ ID NO: 38 is the signal peptide.

In one aspect, the mature polypeptide is amino acids 1 to 119 of SEQ ID NO: 40. Amino acids −26 to −1 of SEQ ID NO: 40 is the signal peptide.

In one aspect, the mature polypeptide is amino acids 1 to 117 of SEQ ID NO: 42. Amino acids −26 to −1 of SEQ ID NO: 42 is the signal peptide.

In one aspect, the mature polypeptide is amino acids 1 to 108 of SEQ ID NO: 44. Amino acids −29 to −1 of SEQ ID NO: 44 is the signal peptide.

In one aspect, the mature polypeptide is amino acids 1 to 120 of SEQ ID NO: 46. Amino acids −30 to −1 of SEQ ID NO: 46 is the signal peptide.

In one aspect, the mature polypeptide is amino acids 1 to 119 of SEQ ID NO: 48. Amino acids −26 to −1 of SEQ ID NO: 48 is the signal peptide.

In one aspect, the mature polypeptide is amino acids 1 to 117 of SEQ ID NO: 50. Amino acids −27 to −1 of SEQ ID NO: 50 is the signal peptide.

In one aspect, the mature polypeptide is amino acids 1 to 156 of SEQ ID NO: 52. Amino acids −34 to −1 of SEQ ID NO: 52 is the signal peptide.

In one aspect, the mature polypeptide is amino acids 1 to 115 of SEQ ID NO: 54. Amino acids −23 to −1 of SEQ ID NO: 54 is the signal peptide.

In one aspect, the mature polypeptide is amino acids 1 to 108 of SEQ ID NO: 56. Amino acids −27 to −1 of SEQ ID NO: 56 is the signal peptide.

In one aspect, the mature polypeptide is amino acids 1 to 116 of SEQ ID NO: 69. Amino acids −15 to −1 of SEQ ID NO: 69 is the signal peptide.

In one aspect, the mature polypeptide is amino acids 1 to 112 of SEQ ID NO: 71. Amino acids −19 to −1 of SEQ ID NO: 71 is the signal peptide.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

The term "mature polypeptide coding sequence" means a polynucleotide that encodes a mature polypeptide having RNase activity. In one aspect, the mature polypeptide coding sequence is nucleotides 88 to 519 of SEQ ID NO: 1, and nucleotides 1 to 87 of SEQ ID NO: 1 encode a signal peptide.

In another aspect, the mature polypeptide coding sequence is nucleotides 79 to 435 of SEQ ID NO: 4, and nucleotides 1 to 78 of SEQ ID NO: 4 encode a signal peptide.

In another aspect, the mature polypeptide coding sequence is nucleotides 67 to 468 of SEQ ID NO: 7, and nucleotides 1 to 66 of SEQ ID NO: 7 encode a signal peptide.

In another aspect, the mature polypeptide coding sequence is nucleotides 73 to 546 of SEQ ID NO: 10, and nucleotides 1 to 72 of SEQ ID NO: 10 encode a signal peptide.

In another aspect, the mature polypeptide coding sequence is nucleotides 52 to 280 and 348 to 460 of SEQ ID NO: 13, and nucleotides 1 to 51 of SEQ ID NO: 13 encode a signal peptide.

In another aspect, the mature polypeptide coding sequence is nucleotides 61 to 477 of SEQ ID NO: 35, and nucleotides 1 to 60 of SEQ ID NO: 35 encode a signal peptide.

In another aspect, the mature polypeptide coding sequence is nucleotides 61 to 468 of SEQ ID NO: 37, and nucleotides 1 to 60 of SEQ ID NO: 37 encode a signal peptide.

In another aspect, the mature polypeptide coding sequence is nucleotides 79 to 435 of SEQ ID NO: 39, and nucleotides 1 to 78 of SEQ ID NO: 39 encode a signal peptide.

In another aspect, the mature polypeptide coding sequence is nucleotides 79 to 429 of SEQ ID NO: 41, and nucleotides 1 to 78 of SEQ ID NO: 41 encode a signal peptide.

In another aspect, the mature polypeptide coding sequence is nucleotides 88 to 411 of SEQ ID NO: 43, and nucleotides 1 to 87 of SEQ ID NO: 43 encode a signal peptide.

In another aspect, the mature polypeptide coding sequence is nucleotides 91 to 450 of SEQ ID NO: 45, and nucleotides 1 to 90 of SEQ ID NO: 45 encode a signal peptide.

In another aspect, the mature polypeptide coding sequence is nucleotides 79 to 435 of SEQ ID NO: 47, and nucleotides 1 to 78 of SEQ ID NO: 47 encode a signal peptide.

In another aspect, the mature polypeptide coding sequence is nucleotides 82 to 432 of SEQ ID NO: 49, and nucleotides 1 to 81 of SEQ ID NO: 49 encode a signal peptide.

In another aspect, the mature polypeptide coding sequence is nucleotides 103 to 570 of SEQ ID NO: 51, and nucleotides 1 to 102 of SEQ ID NO: 51 encode a signal peptide.

In another aspect, the mature polypeptide coding sequence is nucleotides 70 to 414 of SEQ ID NO: 53, and nucleotides 1 to 69 of SEQ ID NO: 53 encode a signal peptide.

In another aspect, the mature polypeptide coding sequence is nucleotides 82 to 405 of SEQ ID NO: 55, and nucleotides 1 to 81 of SEQ ID NO: 55 encode a signal peptide.

In another aspect, the mature polypeptide coding sequence is nucleotides 46 to 283 and 350 to 459 of SEQ ID NO: 68, and nucleotides 1 to 45 of SEQ ID NO: 69 encode a signal peptide.

In another aspect, the mature polypeptide coding sequence is nucleotides 129 to 354 and 418 to 527 of SEQ ID NO: 70, and nucleotides 1 to 15 and 87 to 128 of SEQ ID NO: 70 encode a signal peptide.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

The term "operably linked" means a configuration in which a control sequence is placed at an appropriate position relative to the coding sequence of a polynucleotide such that the control sequence directs expression of the coding sequence.

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−
Total Number of Gaps in Alignment)

The term "variant" means a polypeptide having RNase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Nomenclature

For purposes of the present invention, the nomenclature [E/Q] or simply [EQ] means that the amino acid at this position may be a glutamic acid (Glu, E) or a glutamine (Gln, Q). Likewise, the nomenclature [V/G/A/I] or [VGAI] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

Polypeptides Having RNase Activity

The present invention relates to polypeptides having RNase activity, i.e. RNases. The RNases of the present invention are useful in cleaning compositions and are effective in deep cleaning of surfaces such as fabrics. The RNases of the present invention are effective in reducing or removing biofilm. Biofilm is an extracellular matrix produced by various microorganisms. The extracellular polymeric matrix is composed of polysaccharides, extracellular RNA, DNA and proteins. The biofilm may be sticky or glueing, which when present on textile may give rise to redeposition or backstaining of soil resulting in a greying of the textile. Another drawback is that biofilms often cause malodor as various malodor-related molecules are trapped within the biofilm structure. The RNases of the invention are therefore useful for prevention, reduction or removal of malodor and for prevention or reduction of redeposition and improving whiteness.

The polypeptides of the invention having RNase activity comprise a domain from the RNase Barnase (Swiss Prot P00648 (SEQ ID NO 34)), PF00545 family) as well as the clusters such as the clades. A clade is a grouping that has a shared phylogeny and includes a common ancestor and all the descendants (living and extinct) of that ancestor (http://evolution.berkeley.edu/evolibrary/article/0_0_0/evo_06).

Thus, in the present context a clade refers to a subgroup of closely related RNases.

A phylogenetic tree was constructed of polypeptide sequences containing a Barnase domain, as defined in PFAM (PF000545, Pfam version 30.0 Finn (2016). *Nucleic Acids Research*, Database Issue 44 D279-D285). The phylogenetic tree was constructed from a multiple alignment of mature polypeptide sequences containing at least one Barnase domain. The sequences were aligned using the MUSCLE algorithm version 3.8.31 (Edgar, 2004. *Nucleic Acids Research* 32(5): 1792-1797), and the trees were constructed using FastTree version 2.1.8 (Price et al., 2010, *PloS one* 5(3)) and visualized using iTOL (Letunic & Bork, 2007. *Bioinformatics* 23(1): 127-128). The polypeptides comprising the Barnase domain can be separated into multiple distinct sub-clusters, or clades, where we denoted the clades listed below. Distinct motifs for each clade are described in Example 10.

In one embodiment of the invention the RNases of the invention belong to a specific subgroup or clade comprising one or more motif(s) EYTV (SEQ ID NO: 28), [YRF]E[AYFWC]D (SEQ ID NO: 29), IGGD (SEQ ID NO: 30), YPH (SEQ ID NO: 31), HTGA (SEQ ID NO: 32) or DRV (SEQ ID NO:33).

In one aspect, the polypeptide of the invention having RNase activity belongs to the EYTV clade and comprises the motif EYTV (SEQ ID NO: 28). In one embodiment of this aspect, the polypeptide comprises the extended motif YXEYTVXTPXXXXRGXRR (SEQ ID NO: 78), wherein each X independently may be any naturally occurring amino acid.

In one aspect, the polypeptide of the invention having RNase activity belongs to the EAD clade and comprises one or more of the motif(s) [YRF]E[AYFWC]D (SEQ ID NO: 29) or IGGD (SEQ ID NO: 30). In one embodiment of this aspect, the polypeptide comprises the extended motif [WY][YRF]E[AYFWC]D[IV] (SEQ ID NO: 79). In another embodiment, the polypeptide comprises the extended motif GXXIGGDXFXN (SEQ ID NO: 80), wherein each X independently may be any naturally occurring amino acid.

In one aspect, the polypeptide of the invention having RNase activity belongs to the YPH clade and comprises one or more of the motif(s) YPH (SEQ ID NO: 31), HTGA (SEQ ID NO: 32) or DRV (SEQ ID NO:33). In one embodiment of this aspect, the polypeptide comprises the extended motif YPHX[YFA]X[ND]XE (SEQ ID NO: 81), wherein each X independently may be any naturally occurring amino acid. In another embodiment, the polypeptide comprises the extended motif PGXDRV (SEQ ID NO: 82), wherein X may be any naturally occurring amino acid. In another embodiment, the polypeptide comprises the extended motif THTGA[SR]G (SEQ ID NO: 83).

One aspect of the invention relates to a polypeptide having RNase activity, selected from the group consisting of:
(a) a polypeptide having at least 80% sequence identity to the polypeptide of SEQ ID NO: 3;
(b) a polypeptide having at least 80% sequence identity to the polypeptide of SEQ ID NO: 6;
(c) a polypeptide having at least 80% sequence identity to the polypeptide of SEQ ID NO: 9;
(d) a polypeptide having at least 80% sequence identity to the polypeptide of SEQ ID NO: 12;
(e) a polypeptide having at least 80% sequence identity to the polypeptide of SEQ ID NO: 15;
(f) a polypeptide having at least 80% sequence identity to the polypeptide of SEQ ID NO: 57;
(g) a polypeptide having at least 80% sequence identity to the polypeptide of SEQ ID NO: 58;
(h) a polypeptide having at least 80% sequence identity to the polypeptide of SEQ ID NO: 59;
(i) a polypeptide having at least 80% sequence identity to the polypeptide of SEQ ID NO: 60;
(j) a polypeptide having at least 80% sequence identity to the polypeptide of SEQ ID NO: 61;
(k) a polypeptide having at least 80% sequence identity to the polypeptide of SEQ ID NO: 62;
(l) a polypeptide having at least 80% sequence identity to the polypeptide of SEQ ID NO: 63;
(m) a polypeptide having at least 80% sequence identity to the polypeptide of SEQ ID NO: 64;
(n) a polypeptide having at least 80% sequence identity to the polypeptide of SEQ ID NO: 65;
(o) a polypeptide having at least 80% sequence identity to the polypeptide of SEQ ID NO: 66;
(p) a polypeptide having at least 80% sequence identity to the polypeptide of SEQ ID NO: 67;
(q) a polypeptide having at least 80% sequence identity to the polypeptide of SEQ ID NO: 72;
(r) a polypeptide having at least 80% sequence identity to the polypeptide of SEQ ID NO: 73;
(s) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 72 and SEQ ID NO: 73, wherein the variant has RNase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(t) a polypeptide comprising the polypeptide of (a), (b), (c), (d), (e), (f), (g), (h), (i), (j), (k), (l), (m), (n), (o), (p), (q), (r) or (s) and an N-terminal and/or C-terminal His-tag and/or HQ-tag;
(u) a polypeptide comprising the polypeptide of (a), (b), (c), (d), (e), (f), (g), (h), (i), (j), (k), (l), (m), (n), (o), (p), (q), (r) or (s) and an N-terminal and/or C-terminal extension of between 1 and 10 amino acids;
(v) a fragment of the polypeptide of (a), (b), (c), (d), (e), (f), (g), (h), (i), (j), (k), (l), (m), (n), (o), (p), (q), (r) or (s) having RNase activity and having at least 90% of the length of the mature polypeptide;
(w) a polypeptide comprising one or more of the motif(s) EYTV (SEQ ID NO: 28), [YRF]E[AYFWC]D (SEQ ID NO: 29), IGGD (SEQ ID NO: 30), YPH (SEQ ID NO: 31), HTGA (SEQ ID NO: 32) or DRV (SEQ ID NO:33); and
(x) a polypeptide comprising one or more of the motifs YXEYTVXTPXXXXRGXRR (SEQ ID NO: 78), [WY][YRF]E[AYFWC]D[IV] (SEQ ID NO: 79), GXXIGGDXFXN (SEQ ID NO: 80), YPHX[YFA]X[ND]XE (SEQ ID NO: 81), PGXDRV (SEQ ID NO: 82) or THTGA[SR]G (SEQ ID NO: 83).

The RNases of the present invention are useful in cleaning compositions and are effective in deep cleaning of surfaces such as fabrics and in reducing or removing RNA soiling from e.g. organic matter. One example of organic matter is biofilm which is an extracellular matrix produced by various microorganisms. As described above, organic matter like biofilm may be sticky or glueing, and may give rise to redeposition or backstaining of soil resulting in greying of a textile. Another drawback of organic matter such as biofilm is malodor caused by various malodor-related molecules that are often associated with organic matter such as biofilm.

One aspect of the invention relates to the use of a polypeptide comprising one or more of the motif(s) EYTV (SEQ ID NO: 28), [YRF]E[AYFWC]D (SEQ ID NO: 29), IGGD (SEQ ID NO: 30), YPH (SEQ ID NO: 31), HTGA (SEQ ID NO: 32) or DRV (SEQ ID NO: 33) and having RNase activity for deep cleaning of an item, wherein the item is a textile. In one embodiment, the polypeptide may comprise one or more of the motifs YXEYTVXTPXXXXRGXRR (SEQ ID NO: 78), [WY][YRF]E[AYFWC]D[IV] (SEQ ID NO: 79), GXXIGGDXFXN (SEQ ID NO: 80), YPHX[YFA]X[ND]XE (SEQ ID NO: 81), PGXDRV (SEQ ID NO: 82) or THTGA[SR]G (SEQ ID NO: 83).

One aspect relates to a laundering method for laundering an item comprising the steps of:
a. exposing an item to a wash liquor comprising a polypeptide selected from the group consisting of SEQ ID NO: 3, SEQ ID NO: 6, SEQ ID NO: 9, SEQ ID NO: 12, SEQ ID NO: 15, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 72 and SEQ ID NO: 73, or a cleaning composition comprising a polypeptide selected from the group consisting of SEQ ID NO: 3, SEQ ID NO: 6, SEQ ID NO: 9, SEQ ID NO: 12, SEQ ID NO: 15, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 72 and SEQ ID NO: 73;
b. completing at least one wash cycle; and
c. optionally rinsing the item,
wherein the item is a textile.

In one embodiment, the present invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the RNase activity of the mature polypeptide of SEQ ID NO: 2.

In a particular embodiment the invention relates to polypeptides having a sequence identity to the mature polypeptide of SEQ ID NO: 5 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 5.

In a particular embodiment the invention relates to polypeptides having a sequence identity to the mature polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the RNase activity of the mature polypeptide of SEQ ID NO: 8.

In a particular embodiment the invention relates to polypeptides having a sequence identity to the mature polypeptide of SEQ ID NO: 11 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the RNase activity of the mature polypeptide of SEQ ID NO: 11.

In a particular embodiment the invention relates to polypeptides having a sequence identity to the mature polypeptide of SEQ ID NO: 14 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the RNase activity of the mature polypeptide of SEQ ID NO: 14.

In a particular embodiment the invention relates to polypeptides having a sequence identity to the mature polypeptide of SEQ ID NO: 36 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 36.

In a particular embodiment the invention relates to polypeptides having a sequence identity to the mature polypeptide of SEQ ID NO: 38 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 38.

In a particular embodiment the invention relates to polypeptides having a sequence identity to the mature polypeptide of SEQ ID NO: 40 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 40.

In a particular embodiment the invention relates to polypeptides having a sequence identity to the mature polypeptide of SEQ ID NO: 42 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 42.

In a particular embodiment the invention relates to polypeptides having a sequence identity to the mature polypeptide of SEQ ID NO: 44 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 44.

In a particular embodiment the invention relates to polypeptides having a sequence identity to the mature polypeptide of SEQ ID NO: 46 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 46.

In a particular embodiment the invention relates to polypeptides having a sequence identity to the mature polypeptide of SEQ ID NO: 48 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 48.

In a particular embodiment the invention relates to polypeptides having a sequence identity to the mature polypeptide of SEQ ID NO: 50 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 50.

In a particular embodiment the invention relates to polypeptides having a sequence identity to the mature polypeptide of SEQ ID NO: 52 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 52.

In a particular embodiment the invention relates to polypeptides having a sequence identity to the mature polypeptide of SEQ ID NO: 54 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 54.

In a particular embodiment the invention relates to polypeptides having a sequence identity to the mature polypeptide of SEQ ID NO: 56 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 56.

In a particular embodiment the invention relates to polypeptides having a sequence identity to the mature polypeptide of SEQ ID NO: 69 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 69.

In a particular embodiment the invention relates to polypeptides having a sequence identity to the mature polypeptide of SEQ ID NO: 71 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the RNase activity of the mature polypeptide of SEQ ID NO: 71.

In one embodiment, a polypeptide of the invention has been isolated.

A preferred polypeptide of the present invention comprises or consists of the amino acid sequence shown in SEQ ID NO: 3 or an allelic variant thereof; or is a fragment thereof having RNase activity. Another preferred polypeptide comprises or consists of the mature polypeptide of SEQ ID NO: 2. In another embodiment, the polypeptide comprises or consists of amino acids 1 to 144 of SEQ ID NO: 2.

In one embodiment, the polypeptide preferably comprises or consists of the amino acid sequence shown in SEQ ID NO: 3; comprises the amino acid sequence shown in SEQ ID NO: 3 and an N-terminal and/or C-terminal His-tag and/or HQ-tag; comprises the amino acid sequence of SEQ ID NO: 3 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 3.

Another preferred polypeptide of the present invention comprises or consists of the amino acid sequence shown in SEQ ID NO: 6 or an allelic variant thereof; or is a fragment thereof having RNase activity. In another embodiment, the polypeptide comprises or consists of the mature polypeptide of SEQ ID NO: 5. In another embodiment, the polypeptide comprises or consists of amino acids 1 to 119 of SEQ ID NO: 5.

In one embodiment, the polypeptide preferably comprises or consists of the amino acid sequence shown in SEQ ID NO: 6; comprises the amino acid sequence shown in SEQ ID NO: 6 and an N-terminal and/or C-terminal His-tag and/or HQ-tag; comprises the amino acid sequence of SEQ ID NO: 6 and an N-terminal and/or C-terminal extension of between 1 and 10 amino acids;

or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 6.

Another preferred polypeptide of the present invention comprises or consists of the amino acid sequence shown in SEQ ID NO: 9 or an allelic variant thereof; or is a fragment thereof having RNase activity. In another embodiment, the polypeptide comprises or consists of the mature polypeptide of SEQ ID NO: 8. In another embodiment, the polypeptide comprises or consists of amino acids 1 to 134 of SEQ ID NO: 8.

In one embodiment, the polypeptide preferably comprises or consists of the amino acid sequence shown in SEQ ID NO: 9; comprises the amino acid sequence shown in SEQ ID NO: 9 and an N-terminal and/or C-terminal His-tag and/or HQ-tag; comprises the amino acid sequence of SEQ ID NO: 9 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 9.

Another preferred polypeptide of the present invention comprises or consists of the amino acid sequence shown in SEQ ID NO: 12 or an allelic variant thereof; or is a fragment thereof having RNase activity. In another embodiment, the polypeptide comprises or consists of the mature polypeptide of SEQ ID NO: 11. In another embodiment, the polypeptide comprises or consists of amino acids 1 to 158 of SEQ ID NO: 11.

In one embodiment, the polypeptide preferably comprises or consists of the amino acid sequence shown in SEQ ID NO: 12; comprises the amino acid sequence shown in SEQ ID NO: 12 and an N-terminal and/or C-terminal His-tag and/or HQ-tag; comprises the amino acid sequence of SEQ ID NO: 12 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 12.

Another preferred polypeptide of the present invention comprises or consists of the amino acid sequence shown in SEQ ID NO: 15 or an allelic variant thereof; or is a fragment thereof having RNase activity. In another embodiment, the polypeptide comprises or consists of the mature polypeptide of SEQ ID NO: 14. In another embodiment, the polypeptide comprises or consists of amino acids 1 to 114 of SEQ ID NO: 14.

In one embodiment, the polypeptide preferably comprises or consists of the amino acid sequence shown in SEQ ID NO: 15; comprises the amino acid sequence shown in SEQ ID NO: 15 and an N-terminal and/or C-terminal His-tag and/or HQ-tag; comprises the amino acid sequence of SEQ ID NO: 15 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 15.

Another preferred polypeptide of the present invention comprises or consists of the amino acid sequence shown in SEQ ID NO: 57 or an allelic variant thereof; or is a fragment thereof having RNase activity. In another embodiment, the polypeptide comprises or consists of the mature polypeptide of SEQ ID NO: 36.

In one embodiment, the polypeptide preferably comprises or consists of the amino acid sequence shown in SEQ ID NO: 57; comprises the amino acid sequence shown in SEQ ID NO: 57 and an N-terminal and/or C-terminal His-tag and/or HQ-tag; comprises the amino acid sequence of SEQ ID NO: 57 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 57.

Another preferred polypeptide of the present invention comprises or consists of the amino acid sequence shown in SEQ ID NO: 58 or an allelic variant thereof; or is a fragment thereof having RNase activity. In another embodiment, the polypeptide comprises or consists of the mature polypeptide of SEQ ID NO: 38.

In one embodiment, the polypeptide preferably comprises or consists of the amino acid sequence shown in SEQ ID NO: 58; comprises the amino acid sequence shown in SEQ ID NO: 58 and an N-terminal and/or C-terminal His-tag and/or HQ-tag; comprises the amino acid sequence of SEQ ID NO: 58 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 58.

Another preferred polypeptide of the present invention comprises or consists of the amino acid sequence shown in SEQ ID NO: 59 or an allelic variant thereof; or is a fragment thereof having RNase activity. In another embodiment, the polypeptide comprises or consists of the mature polypeptide of SEQ ID NO: 40.

In one embodiment, the polypeptide preferably comprises or consists of the amino acid sequence shown in SEQ ID NO: 59; comprises the amino acid sequence shown in SEQ ID NO: 59 and an N-terminal and/or C-terminal His-tag and/or HQ-tag; comprises the amino acid sequence of SEQ ID NO: 59 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 59.

Another preferred polypeptide of the present invention comprises or consists of the amino acid sequence shown in SEQ ID NO: 60 or an allelic variant thereof; or is a fragment thereof having RNase activity. In another embodiment, the polypeptide comprises or consists of the mature polypeptide of SEQ ID NO: 42.

In one embodiment, the polypeptide preferably comprises or consists of the amino acid sequence shown in SEQ ID NO: 60; comprises the amino acid sequence shown in SEQ ID NO: 60 and an N-terminal and/or C-terminal His-tag and/or HQ-tag; comprises the amino acid sequence of SEQ ID NO: 60 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 60.

Another preferred polypeptide of the present invention comprises or consists of the amino acid sequence shown in SEQ ID NO: 61 or an allelic variant thereof; or is a fragment thereof having RNase activity. In another embodiment, the polypeptide comprises or consists of the mature polypeptide of SEQ ID NO: 44.

In one embodiment, the polypeptide preferably comprises or consists of the amino acid sequence shown in SEQ ID NO: 61; comprises the amino acid sequence shown in SEQ ID NO: 61 and an N-terminal and/or C-terminal His-tag and/or HQ-tag; comprises the amino acid sequence of SEQ ID NO: 61 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 61.

Another preferred polypeptide of the present invention comprises or consists of the amino acid sequence shown in SEQ ID NO: 62 or an allelic variant thereof; or is a fragment thereof having RNase activity. In another embodiment, the polypeptide comprises or consists of the mature polypeptide of SEQ ID NO: 46.

In one embodiment, the polypeptide preferably comprises or consists of the amino acid sequence shown in SEQ ID NO: 61; comprises the amino acid sequence shown in SEQ ID NO: 62 and an N-terminal and/or C-terminal His-tag and/or HQ-tag; comprises the amino acid sequence of SEQ ID NO: 62 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 62.

Another preferred polypeptide of the present invention comprises or consists of the amino acid sequence shown in SEQ ID NO: 63 or an allelic variant thereof; or is a fragment thereof having RNase activity. In another embodiment, the polypeptide comprises or consists of the mature polypeptide of SEQ ID NO:48.

In one embodiment, the polypeptide preferably comprises or consists of the amino acid sequence shown in SEQ ID NO: 63; comprises the amino acid sequence shown in SEQ ID NO: 63 and an N-terminal and/or C-terminal His-tag and/or HQ-tag; comprises the amino acid sequence of SEQ ID NO: 63 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 63.

Another preferred polypeptide of the present invention comprises or consists of the amino acid sequence shown in SEQ ID NO: 64 or an allelic variant thereof; or is a fragment thereof having RNase activity. In another embodiment, the polypeptide comprises or consists of the mature polypeptide of SEQ ID NO: 50.

In one embodiment, the polypeptide preferably comprises or consists of the amino acid sequence shown in SEQ ID NO: 64; comprises the amino acid sequence shown in SEQ ID NO: 64 and an N-terminal and/or C-terminal His-tag and/or HQ-tag; comprises the amino acid sequence of SEQ ID NO: 64 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 64.

Another preferred polypeptide of the present invention comprises or consists of the amino acid sequence shown in SEQ ID NO: 65 or an allelic variant thereof; or is a fragment thereof having RNase activity. In another embodiment, the polypeptide comprises or consists of the mature polypeptide of SEQ ID NO: 52.

In one embodiment, the polypeptide preferably comprises or consists of the amino acid sequence shown in SEQ ID NO: 65; comprises the amino acid sequence shown in SEQ ID NO: 65 and an N-terminal and/or C-terminal His-tag and/or HQ-tag; comprises the amino acid sequence of SEQ ID NO: 65 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 65.

Another preferred polypeptide of the present invention comprises or consists of the amino acid sequence shown in SEQ ID NO: 66 or an allelic variant thereof; or is a fragment thereof having RNase activity. In another embodiment, the polypeptide comprises or consists of the mature polypeptide of SEQ ID NO: 54.

In one embodiment, the polypeptide preferably comprises or consists of the amino acid sequence shown in SEQ ID NO: 66; comprises the amino acid sequence shown in SEQ ID NO: 66 and an N-terminal and/or C-terminal His-tag and/or HQ-tag; comprises the amino acid sequence of SEQ ID NO: 66 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 66.

Another preferred polypeptide of the present invention comprises or consists of the amino acid sequence shown in SEQ ID NO: 67 or an allelic variant thereof; or is a fragment thereof having RNase activity. In another embodiment, the polypeptide comprises or consists of the mature polypeptide of SEQ ID NO: 56.

In one embodiment, the polypeptide preferably comprises or consists of the amino acid sequence shown in SEQ ID NO: 67; comprises the amino acid sequence shown in SEQ ID NO: 67 and an N-terminal and/or C-terminal His-tag and/or HQ-tag; comprises the amino acid sequence of SEQ ID NO: 67 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 67.

Another preferred polypeptide of the present invention comprises or consists of the amino acid sequence shown in SEQ ID NO: 72 or an allelic variant thereof; or is a fragment thereof having RNase activity. In another embodiment, the polypeptide comprises or consists of the mature polypeptide of SEQ ID NO: 69.

In one embodiment, the polypeptide preferably comprises or consists of the amino acid sequence shown in SEQ ID NO: 72; comprises the amino acid sequence shown in SEQ ID NO: 72 and an N-terminal and/or C-terminal His-tag and/or HQ-tag; comprises the amino acid sequence of SEQ ID NO: 72 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 72.

Another preferred polypeptide of the present invention comprises or consists of the amino acid sequence shown in SEQ ID NO: 73 or an allelic variant thereof; or is a fragment thereof having RNase activity. In another embodiment, the polypeptide comprises or consists of the mature polypeptide of SEQ ID NO: 71.

In one embodiment, the polypeptide preferably comprises or consists of the amino acid sequence shown in SEQ ID NO: 73; comprises the amino acid sequence shown in SEQ ID NO: 73 and an N-terminal and/or C-terminal His-tag and/or HQ-tag; comprises the amino acid sequence of SEQ ID NO: 73 and an N-terminal and/or C-terminal extension of between 1 and 10 amino acids; or is a fragment thereof having RNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 73.

In one embodiment, the present invention relates to variants of the mature polypeptide shown in SEQ ID NO: 3 comprising a substitution, deletion, and/or insertion at one or more (e.g., several) positions. In some embodiment, the number of amino acid substitutions, deletions and/or insertions introduced into the mature polypeptide of SEQ ID NO: 3 is up to 10, e.g., 1, 2, 3, 4, 5, 6, 7, 8, 9, or 10.

In one embodiment, the present invention relates to variants of the mature polypeptide shown in SEQ ID NO: 6 comprising a substitution, deletion, and/or insertion at one or more (e.g., several) positions. In some embodiment, the number of amino acid substitutions, deletions and/or insertions introduced into the mature polypeptide shown in SEQ ID NO: 6 is up to 10, e.g., 1, 2, 3, 4, 5, 6, 7, 8, 9, or 10.

In one embodiment, the present invention relates to variants of the mature polypeptide shown in SEQ ID NO: 9 comprising a substitution, deletion, and/or insertion at one or more (e.g., several) positions. In some embodiment, the number of amino acid substitutions, deletions and/or insertions introduced into the mature polypeptide shown in SEQ ID NO: 9 is up to 10, e.g., 1, 2, 3, 4, 5, 6, 7, 8, 9, or 10.

In one embodiment, the present invention relates to variants of the mature polypeptide shown in SEQ ID NO: 12 comprising a substitution, deletion, and/or insertion at one or more (e.g., several) positions. In some embodiment, the number of amino acid substitutions, deletions and/or insertions introduced into the mature polypeptide shown in SEQ ID NO: 12 is up to 10, e.g., 1, 2, 3, 4, 5, 6, 7, 8, 9, or 10.

In one embodiment, the present invention relates to variants of the mature polypeptide shown in SEQ ID NO: 15 comprising a substitution, deletion, and/or insertion at one or more (e.g., several) positions. In some embodiment, the number of amino acid substitutions, deletions and/or insertions introduced into the mature polypeptide shown in SEQ ID NO: 15 is up to 10, e.g., 1, 2, 3, 4, 5, 6, 7, 8, 9, or 10.

In one embodiment, the present invention relates to variants of the mature polypeptide shown in SEQ ID NO: 57 comprising a substitution, deletion, and/or insertion at one or more (e.g., several) positions. In some embodiment, the number of amino acid substitutions, deletions and/or insertions introduced into the mature polypeptide shown in SEQ ID NO: 57 is up to 10, e.g., 1, 2, 3, 4, 5, 6, 7, 8, 9, or 10.

In one embodiment, the present invention relates to variants of the mature polypeptide shown in SEQ ID NO: 58 comprising a substitution, deletion, and/or insertion at one or more (e.g., several) positions. In some embodiment, the number of amino acid substitutions, deletions and/or insertions introduced into the mature polypeptide shown in SEQ ID NO: 58 is up to 10, e.g., 1, 2, 3, 4, 5, 6, 7, 8, 9, or 10.

In one embodiment, the present invention relates to variants of the mature polypeptide shown in SEQ ID NO: 59 comprising a substitution, deletion, and/or insertion at one or more (e.g., several) positions. In some embodiment, the number of amino acid substitutions, deletions and/or insertions introduced into the mature polypeptide shown in SEQ ID NO: 59 is up to 10, e.g., 1, 2, 3, 4, 5, 6, 7, 8, 9, or 10.

In one embodiment, the present invention relates to variants of the mature polypeptide shown in SEQ ID NO: 60 comprising a substitution, deletion, and/or insertion at one or more (e.g., several) positions. In some embodiment, the number of amino acid substitutions, deletions and/or insertions introduced into the mature polypeptide shown in SEQ ID NO: 60 is up to 10, e.g., 1, 2, 3, 4, 5, 6, 7, 8, 9, or 10.

In one embodiment, the present invention relates to variants of the mature polypeptide shown in SEQ ID NO: 61 comprising a substitution, deletion, and/or insertion at one or more (e.g., several) positions. In some embodiment, the number of amino acid substitutions, deletions and/or insertions introduced into the mature polypeptide shown in SEQ ID NO: 61 is up to 10, e.g., 1, 2, 3, 4, 5, 6, 7, 8, 9, or 10.

In one embodiment, the present invention relates to variants of the mature polypeptide shown in SEQ ID NO: 62 comprising a substitution, deletion, and/or insertion at one or more (e.g., several) positions. In some embodiment, the number of amino acid substitutions, deletions and/or insertions introduced into the mature polypeptide shown in SEQ ID NO: 62 is up to 10, e.g., 1, 2, 3, 4, 5, 6, 7, 8, 9, or 10.

In one embodiment, the present invention relates to variants of the mature polypeptide shown in SEQ ID NO: 63 comprising a substitution, deletion, and/or insertion at one or more (e.g., several) positions. In some embodiment, the number of amino acid substitutions, deletions and/or insertions introduced into the mature polypeptide shown in SEQ ID NO: 63 is up to 10, e.g., 1, 2, 3, 4, 5, 6, 7, 8, 9, or 10.

In one embodiment, the present invention relates to variants of the mature polypeptide shown in SEQ ID NO: 64 comprising a substitution, deletion, and/or insertion at one or more (e.g., several) positions. In some embodiment, the number of amino acid substitutions, deletions and/or insertions introduced into the mature polypeptide shown in SEQ ID NO: 64 is up to 10, e.g., 1, 2, 3, 4, 5, 6, 7, 8, 9, or 10.

In one embodiment, the present invention relates to variants of the mature polypeptide shown in SEQ ID NO: 65 comprising a substitution, deletion, and/or insertion at one or more (e.g., several) positions. In some embodiment, the number of amino acid substitutions, deletions and/or insertions introduced into the mature polypeptide shown in SEQ ID NO: 65 is up to 10, e.g., 1, 2, 3, 4, 5, 6, 7, 8, 9, or 10.

In one embodiment, the present invention relates to variants of the mature polypeptide shown in SEQ ID NO: 66 comprising a substitution, deletion, and/or insertion at one or more (e.g., several) positions. In some embodiment, the number of amino acid substitutions, deletions and/or insertions introduced into the mature polypeptide shown in SEQ ID NO: 66 is up to 10, e.g., 1, 2, 3, 4, 5, 6, 7, 8, 9, or 10.

In one embodiment, the present invention relates to variants of the mature polypeptide shown in SEQ ID NO: 67 comprising a substitution, deletion, and/or insertion at one or more (e.g., several) positions. In some embodiment, the number of amino acid substitutions, deletions and/or insertions introduced into the mature polypeptide shown in SEQ ID NO: 67 is up to 10, e.g., 1, 2, 3, 4, 5, 6, 7, 8, 9, or 10.

In one embodiment, the present invention relates to variants of the mature polypeptide shown in SEQ ID NO: 72 comprising a substitution, deletion, and/or insertion at one or more (e.g., several) positions. In some embodiment, the number of amino acid substitutions, deletions and/or insertions introduced into the mature polypeptide shown in SEQ ID NO: 72 is up to 10, e.g., 1, 2, 3, 4, 5, 6, 7, 8, 9, or 10.

In one embodiment, the present invention relates to variants of the mature polypeptide shown in SEQ ID NO: 73 comprising a substitution, deletion, and/or insertion at one or more (e.g., several) positions. In some embodiment, the number of amino acid substitutions, deletions and/or insertions introduced into the mature polypeptide shown in SEQ ID NO: 73 is up to 10, e.g., 1, 2, 3, 4, 5, 6, 7, 8, 9, or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a polyhistidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for RNase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. By such alignment to Barnase from *B. amyloliquifaciens* SWISSPROT:P00648 the following active site residues were identified in the mature sequences as follows: SEQ ID:3 His130, Glu101; SEQ ID:6 His110, Glu82; SEQ ID:9 His123, Glu93 and SEQ ID:12 His150, Glu121.

The RNase Barnase, Swiss Prot P00648 (SEQ ID NO 34) from the PF00545 family of ribonucleases catalyzes hydrolysis at diribonucleotide GpN sites. Cleavage occurs in two steps using a general acid-base mechanism: a cyclic intermediate is formed during the first transesterification step, which is then hydrolysed to release the cleaved RNA. The two most important residues involved in catalysis are Glu73 and His102, which are both believed to be essential for enzymatic activity. Glu73 is the general base whilst His102 is the general acid. Barnase has no disulfide bonds, nor does it require divalent cations or non-peptide components to fold.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

Sources of Polypeptides Having RNase Activity

A polypeptide having RNase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect, the polypeptide is a *Paenibacillus* polypeptide. One embodiment of this aspect is e.g. a polypeptide obtained from *Paenibacillus* sp-18057. Another embodiment of this aspect is e.g. a polypeptide obtained from *Paenibacillus* sp-62770. Another embodiment of this aspect is a polypeptide obtained from *Paenibacillus* sp-18006. Another embodiment of this aspect is a polypeptide obtained from *Paenibacillus* sp-62724. Another embodiment of this aspect is a polypeptide obtained from *Paenibacillus tundrae*.

In one aspect, the polypeptide is a *Amycolatopsis* polypeptide, e.g., a polypeptide obtained from *Amycolatopsis azurea*.

In one aspect, the polypeptide is an *Acremonium* polypeptide, e.g., a polypeptide obtained from *Acremonium alcalophilum*.

In one aspect, the polypeptide is a *Stenotrophomonas* polypeptide, e.g., a polypeptide obtained from *Stenotrophomonas rhizophila*.

In one aspect, the polypeptide is an *Erwinia* polypeptide, e.g., a polypeptide obtained from *Erwinia persicina*.

In one aspect, the polypeptide is a *Saccharothrix* polypeptide, e.g., a polypeptide obtained from *Saccharothrix* sp-62935.

In one aspect, the polypeptide is a *Saccharopolyspora* polypeptide, e.g., a polypeptide obtained from *Saccharopolyspora endophytica*.

In one aspect, the polypeptide is a *Amycolatopsis* polypeptide, e.g., a polypeptide obtained from *Amycolatopsis circi*.

In one aspect, the polypeptide is an *Alkalimonas* polypeptide, e.g., a polypeptide obtained from *Alkalimonas* sp-62516.

In one aspect, the polypeptide is a *Nonomuraea* polypeptide, e.g., a polypeptide obtained from *Nonomuraea dietziae*.

In one aspect, the polypeptide is a *Trichoderma* polypeptide, e.g., a polypeptide obtained from *Trichoderma harzianum*.

In one aspect, the polypeptide is a *Fusarium* polypeptide, e.g., a polypeptide obtained from *Fusarium solani*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In one embodiment, the polynucleotide encoding the polypeptide of the present invention has been isolated.

In one embodiment, the present invention relates to a polynucleotide encoding a polypeptide having RNase activity wherein the polynucleotide has a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 7 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 10 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 13 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 35 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 37 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 39 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 41 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 43 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 45 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 47 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 49 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 51 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 53 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 55 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 68 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having RNase activity wherein the polynucleotide has a sequence identity to the mature polypeptide coding sequence of SEQ ID NO: 70 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, PCR: *A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Paenibacillus, Amycolatopsis, Stenotrophomonas, Erwinia, Saccharothrix, Saccharopolyspora, Amycolatopsis, Alkalimonas, Nonomuraea* or a related organism and thus, for example, may be an allelic or species variant of the polypeptide encoding region of the polynucleotide. The polynucleotides may also be cloned e.g. from a strain of *Acremonium, Trichoderma* or *Fusarium*.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, Molecular Microbiology 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus nigeralpha*-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* crylIIA gene (WO 94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus nigeralpha-glucosidase Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains one or more elements that permit integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (*Endomycetales*), basidiosporogenous yeast, and yeast belonging to the *Fungi Imperfecti* (*Blastomycetes*). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium solani, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Paenibacillus* cell. In one embodiment, the *Paenibacillus* cell is a *Paenibacillus* sp-18057 cell, a *Paenibacillus* sp-62770 cell, a *Paenibacillus* sp-62724 cell or a *Paenibacillus tundrae* cell. In one aspect, the cell is an *Amycolatopsis* cell, for example a *Amycolatopsis* azurea cell. In one aspect, the cell is a *Stenotrophomonas* cell, for example a *Stenotrophomonas rhizophila* cell. In one aspect, the cell is an *Erwinia* cell, for example an *Erwinia persicina* cell. In one aspect, the cell is a *Saccharothrix* cell, for example a *Saccharothrix* sp-62935 cell. In one aspect, the cell is a *Saccharopolyspora* cell, for example a *Saccharopolyspora endophytica* cell. In one aspect, the cell is an *Alkalimonas* cell, for example an *Alkalimonas* sp-62516 cell. In one aspect, the cell is a *Nonomuraea* cell, for example a *Nonomuraea dietziae* cell.

The host cell may also e.g. be an *Acremonium* cell, for example an *Acremonium alcalophilum* cell, a *Trichoderma* cell, for example a *Trichoderma harzianum* cell, or a *Fusarium* cell, for example a *Fusarium solani* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides having RNase activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In one embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The invention relates to compositions comprising an RNase of the present invention in combination with one or more additional components. The choice of additional components is within the skill of the artisan and includes conventional ingredients, including the exemplary non-limiting components set forth below.

One embodiment of the invention relates to a composition comprising:
a) at least 0.001 ppm, such as at least 0.01 ppm or at least 0.1 ppm, of at least one polypeptide having RNase activity, wherein the RNase is selected from the group consisting of: SEQ ID NO 3, SEQ ID NO 6, SEQ ID NO 9, SEQ ID NO 12, SEQ ID NO 15, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 72 and SEQ ID NO: 73, and polypeptides having at least 80% sequence identity hereto;
b) at least one adjunct ingredient.

One embodiment of the invention relates to a cleaning composition comprising:
a) at least 0.001 ppm, such as at least 0.01 ppm or at least 0.1 ppm, of at least one polypeptide having RNase activity, wherein the RNase is selected from the group consisting of: SEQ ID NO 3, SEQ ID NO 6, SEQ ID NO 9, SEQ ID NO 12, SEQ ID NO 15, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 72 and SEQ ID NO: 73, and polypeptides having at least 80% sequence identity hereto;
b) at least one cleaning composition component, preferably selected from surfactants, builders, bleach components, polymers, dispersing agents and additional enzymes.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN® and TWEEN®, and combinations thereof.

When included therein the detergent will usually contain from about 0.1% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.1% to about 10% by weight of a zwitterionic surfactant. Non-limiting examples of zwitterionic surfactants include betaines such as alkyldimethylbetaines, sulfobetaines, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis (methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn (O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds, such as iron or cobalt complexes.

In some embodiments, where a source of a peracid is included, an organic bleach catalyst or bleach booster may be used having one of the following formulae:

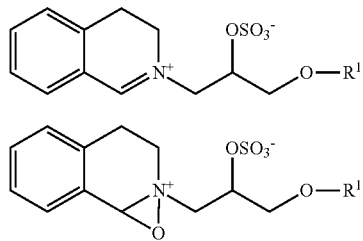

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate;

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C. I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The detergent additive as well as the detergent composition may comprise one or more additional enzymes such as at least one lipase, cutinase, amylase, carbohydrase, cellulase, pectinase, mannanase, arabinase, galactanase, xylanase, oxidase, e.g., laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes NS) Carezyme Premium™ (Novozymes NS), Celluclean™ (Novozymes NS), Celluclean Classic™ (Novozymes NS), Cellusoft™ (Novozymes NS), Whitezyme™ (Novozymes NS), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes NS).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes NS).

Lipases and Cutinases

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes NS), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases

Suitable amylases include alpha-amylases and/or a glucoamylases and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K

E187P+I203Y+R458N+T459S+D460T+G476K wherein the variants optionally further comprise a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I wherein the variants optionally further comprise a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes NS), and Rapidase™, Purastar™/Effectenz™, Powerase, Preferenz S1000, Preferenz S100 and Preferenz S110 (from Genencor International Inc./DuPont).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from Bacillus such as Bacillus lentus, B. alkalophilus, B. subtilis, B. amyloliquefaciens, Bacillus pumilus and Bacillus gibsonii described in; U.S. Pat. No. 7,262,042 and WO09/021867, and subtilisin lentus, subtilisin Novo, subtilisin Carlsberg, Bacillus licheniformis, subtilisin BPN', subtilisin 309, subtilisin 147 and subtilisin 168 described in WO89/06279 and protease PD138 described in (WO93/18140). Other useful proteases may be those described in WO 92/175177, WO 01/016285, WO 02/026024 and WO 02/016547. Examples of trypsin-like proteases are trypsin (e.g. of porcine or bovine origin) and the Fusarium protease described in WO 89/06270, WO 94/25583 and WO 05/040372, and the chymotrypsin proteases derived from Cellumonas described in WO 05/052161 and WO 05/052146.

A further preferred protease is the alkaline protease from Bacillus lentus DSM 5483, as described for example in WO 95/23221, and variants thereof which are described in WO 92/21760, WO 95/23221, EP 1921147 and EP 1921148.

Examples of metalloproteases are the neutral metalloprotease as described in WO07/044993 (Genencor Int.) such as those derived from Bacillus amyloliquefaciens.

Examples of useful proteases are the variants described in: WO 92/19729, WO 96/034946, WO 98/20115, WO 98/20116, WO 99/011768, WO 01/44452, WO 03/006602, WO 04/03186, WO 04/041979, WO 07/006305, WO 11/036263, WO 11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the Bacillus lentus protease shown in SEQ ID NO 1 of WO 2016/001449. More preferred the subtilase variants may comprise one of more of the following mutations: S3T, V41, S9R, S9E, A15T, S24G, S24R, K27R, N42R, S55P, G59E, G59D, N60D, N60E, V66A, N74D, N85S, N85R, G96S, G96A, S97G, S97D, S97A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211 D, N212D, N2125, M2165, A226V, K229L, Q230H, Q239R, N246K, N255W, N255D, N255E, L256E, L256D T268A, R269H. The protease variants are preferably variants of the Bacillus lentus protease (Savinase®) shown in SEQ ID NO 1 of WO 2016/001449, the Bacillus amyloliquefaciens protease (BPN') shown in SEQ ID NO 2 of WO2016/001449. The protease variants preferably have at least 80% sequence identity to SEQ ID NO 1 or SEQ ID NO 2 of WO 2016/001449.

A protease variant comprising a substitution at one or more positions corresponding to positions 171, 173, 175, 179, or 180 of SEQ ID NO: 1 of WO2004/067737, wherein said protease variant has a sequence identity of at least 75% but less than 100% to SEQ ID NO: 1 of WO 2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes NS), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (Bacillus alkalophilus subtilisin) from Kao.

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from Coprinopsis, e.g., from C. cinerea (EP 179,486), and variants thereof as those described in WO 93/24618, WO 95/10602, and WO 98/15257.

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as Caldariomyces, e.g., C. fumago, Alternaria, Curvularia, e.g., C. verruculosa and C. inaequalis, Drechslera, Ulocladium and Botrytis.

Haloperoxidases have also been isolated from bacteria such as Pseudomonas, e.g., P. pyrrocinia and Streptomyces, e.g., S. aureofaciens.

A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinerea*, as disclosed in WO 97/08325; or from *Myceliophthora thermophila*, as disclosed in WO 95/33836.

Dispersants

The detergent compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, CI-C 6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Granular Detergent Formulations

The composition(s) of the invention may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component.

The multi-enzyme co-granule may comprise an RNase of the invention and (a) one or more enzymes selected from lipases, hemicellulases, proteases, amylases, cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

Uses

T+he polypeptides of the invention having RNase activity may be used for deep cleaning of an item, such as a textile. In one embodiment of the invention relates to the use of an RNase according to the invention for prevention, reduction or removal of malodor. One embodiment of the invention relates to the use of an RNase of the invention for prevention or reduction of anti-redeposition and/or for improvement of whiteness of a textile subjected to multiple washes. When the biofilm components, e.g. RNA, of the extracellular biofilm matrix are removed or reduced the stickiness caused by biofilm is also reduced. The RNases of the invention therefore reduce the greyness of textiles when applied in the compositions of the invention to a cleaning process such as laundry.

One aspect of the invention relates to the use of a polypeptide having RNase activity, selected from the group consisting of SEQ ID NO: 3, SEQ ID NO: 6, SEQ ID NO: 9, SEQ ID NO: 12, SEQ ID NO: 15, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 72 and SEQ ID NO: 73, and polypeptides having at least 80% sequence identity hereto:

(i) for preventing, reducing or removing stickiness of an item;
(ii) for pretreating stains on an item;
(iii) for preventing, reducing or removing redeposition of soil during a wash cycle;
(iv) for preventing, reducing or removing adherence of soil to an item;
(v) for maintaining or improving whiteness of an item; and/or
(vi) for preventing, reducing or removal malodor from an item;
wherein the item is a textile.

EXAMPLES

Assay

Mini Launder-O-Meter (MiniLOM) Model Wash System

MiniLOM is a modified mini wash system of the Launder-O-Meter (LOM), which is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker. Wash performance is assessed in laundry wash experiment using a Mini wash assay, which is a test method where soiled textile is continuously is lifted up and down into the test solution and subsequently rinsed. The wash experiment is conducted under the experimental conditions specified below:

| Detergent | Model A |
| --- | --- |
| | Model detergent A wash liquor (100%) was prepared by dissolving 3.33 g/l of model detergent A containing 12% LAS, 11% AEO Biosoft N25-7 (NI), 5% AEOS (SLES), 6% MPG (mono propylene glycol), 3% ethanol, 3% TEA (triethanolamine), 2.75% cocoa soap, 2.75% soya soap, 2% glycerol, 2% sodium hydroxide, 2% sodium citrate, 1% sodium formiate, 0.2% DTMPA and 0.2% PCA (Propenoic acid = acrylic maleic copolymer) (all percentages are w/w (weight/weight)) in water with hardness 15 dH. |
| Detergent dose | 3.33 g/l |
| pH | Example: "as is" in the current detergent solution and is not adjusted. |
| Water hardness | 15° dH, adjusted by adding CaCl$_2$*2H$_2$O, MgCl$_2$*6H$_2$O and NaHCO$_3$ (4:1:7.5) to milli-Q water. |
| Enzymes | RNases shown in SEQ ID NO 3, 6, 9, 12 and 15 |
| Enzyme conc. | 0.2 and 1 ppm |

Delta Remission Value (ΔRem):

The terms "Delta remission" or "Delta remission value" are defined herein as the result of a reflectance or remission measurement at a certain wavelength which typically is 460 nm. The swatch is measured with one swatch of similar colour as background, preferably a swatch from a repetition wash. A swatch representing each swatch type is measured before the wash. The Delta remission is the remission value of the washed swatch minus the remission value of the unwashed swatch.

Assay I: Testing of RNase Activity

RNase activity was determined by fluorescence using a fluorescence-quenched oligonucleotide probe. This probe emits a signal after nuclease degradation according to the manual from the supplier (RNase alert kit, Integrated DNA Technology, Coralville, Iowa, USA). Briefly, RNase was diluted in water hardness 15° dH to obtain a concentration of 2 ppm, and 5 μl of the substrate was added to 95 μl of the RNase sample. A kinetic curve was measured for 10 min at 22° C. using a Clariostar microplate reader (excitation 490 nm, emission at 520 nm).

TABLE 1

Enzyme activity at 2 ppm (RFU after 10 min).

| RNases | RNase activity in water hardness 15° dH (RFU) | RNase activity in Model A 3.3 g/l (RFU) |
| --- | --- | --- |
| SEQ ID NO 3 Paenibacillus sp-18057 | 4288 | 2833 |
| SEQ ID NO 6 Paenibacillus sp-62770 | 4266 | 1318 |
| SEQ ID NO 9 Amycolatopsis azurea | 3700 | 1362 |
| SEQ ID NO 12 Environmental sample community E | 3883 | 2069 |
| SEQ ID NO 15 Acremonium alcalophilum | 3967 | 2228 |

Example 1: Cloning and Expression of Bacterial RNase Polypeptides of the Invention The RNases were derived from bacterial strains isolated from environmental samples by standard microbiological isolation techniques or from mixed bacterial communities. Isolated pure strains were identified and taxonomy was assigned based on DNA sequencing of the 16S ribosomal genes (Table 2). The strain Amycolatopsis azurea (DSM43854) was purchased from Deutsche Sammlung von Mikroorganismen and Zellkulturen (DSMZ, Braunschweig, Germany)

TABLE 2

| Strain or community | Source Country | Mature protein SEQ ID: |
| --- | --- | --- |
| Paenibacillus sp-18057 | New Zealand | 3 |
| Paenibacillus sp-62770 | New Zealand | 6 |
| Amycolatopsis azurea (DSM43854) | Japan | 9 |
| Environmental sample community E | Denmark | 12 |
| Stenotrophomonas rhizophila | Denmark | 57 |
| Erwinia persicina | Denmark | 58 |
| Paenibacillus tundrae | Sweden | 59 |
| Saccharothrix sp-62935 | United Kingdom | 60 |
| Saccharopolyspora endophytica | India | 61 |

TABLE 2-continued

| Strain or community | Source Country | Mature protein SEQ ID: |
|---|---|---|
| Amycolatopsis circi | Spain | 62 |
| Paenibacillus sp-62770 | USA | 63 |
| Paenibacillus sp-18006 | Japan | 64 |
| Paenibacillus sp-62724 | Denmark | 65 |
| Alkalimonas sp-62516 | China | 66 |
| Nonomuraea dietziae | United Kingdom | 67 |

Chromosomal DNA was isolated from either pure cultures of the individual strains or from mixed cultured communities in the case of Environmental sample community E with the DNeasy Blood & Tissue Kit from Qiagen (Hilden, Germany) and subjected to full genome sequencing using Illumina technology. Genome sequencing, the subsequent assembly of reads and the gene discovery (i.e. annotation of gene functions) are known to persons skilled in the art and such services can be purchased commercially.

The genome sequences were analyzed for putative RNases from the PFAM database family PF00545 (R. D. Finn et al. *Nucleic Acids Research* (2014), 42:D222-D230). This analysis identified fifteen genes encoding putative RNases which were subsequently cloned and recombinantly expressed in *Bacillus subtilis*.

Analysis of the genome region around the RNase gene in the genomes of all strains except the Environmental sample community E indicated that the RNase enzyme was naturally co-expressed with a small protein inhibitor in an operon with a single promotor driving expression of both genes, the inhibitor gene being downstream of the RNase gene. It is known from literature that co-expression of inhibitors can benefit the expression of potentially toxic enzymes (Hartley R W, *J Mol Biol.* 1988 Aug. 20; 202(4): 913-5), and hence the inhibitor was included in the recombinant expression cassettes for expression of these RNases that are naturally co-expressed together with an inhibitor. The RNase from the Environmental sample community E does not have a downstream inhibitor gene and is thus expressed recombinantly without co-expression of an inhibitor.

The genes encoding the RNase and any downstream inhibitor were amplified as a single amplicon by PCR and fused with regulatory elements, affinity purification tag and homology regions for recombination into the pel locus of the *B. subtilis* genome.

The linear integration construct was a SOE-PCR fusion product (Horton, R. M., Hunt, H. D., Ho, S. N., Pullen, J. K. and Pease, L. R. (1989) Engineering hybrid genes without the use of restriction enzymes, gene splicing by overlap extension, *Gene* 77: 61-68) made by fusion of the gene between two *Bacillus subtilis* chromosomal regions along with strong promoters and a chloramphenicol resistance marker. The SOE PCR method is also described in patent application WO 2003/095658.

The genes were expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* crylIiA promoter including stabilizing sequence.

The genes were fused with DNA encoding a *Bacillus clausii* secretion signal (encoding the following amino acid sequence: MKKPLGKIVASTALLISVAFSSSIASA (SEQ ID NO 24)) replacing the native secretion signal. Furthermore, the expression construct resulted in the addition of an amino-terminal poly histidine tail consisting of the amino acid sequence HHHHHHPR (SEQ ID NO 25) to the mature RNases.

The SOE-PCR products were transformed into *Bacillus subtilis* and integrated in the chromosome by homologous recombination into the pectate lyase locus. Subsequently a recombinant *Bacillus subtilis* clone containing the integrated expression construct was grown in liquid culture. The culture broth was centrifuged (20000×g, 20 min) and the supernatant was carefully decanted from the precipitate and used for purification of the enzyme or alternatively sterile filtered supernatant was used directly for assays.

Example 2: Purification of Recombinant Enzymes by Nickel Affinity Chromatography The pH of the cleared supernatant was adjusted to pH 8, filtrated through a 0.2 µM filter, and the supernatant applied to a 5 ml HisTrap™ excel column. Prior to loading, the column had been equilibrated in 5 column volumes (CV) of 50 mM Tris/HCl pH 8. To remove unbound material, the column was washed with 8 CV of 50 mM Tris/HCl pH 8, and elution of the target was obtained with 50 mM HEPES pH 7+10 mM imidazole. The eluted protein was desalted on a HiPrep™ 26/10 desalting column, equilibrated using 3 CV of 50 mM HEPES pH 7+100 mM NaCl. This buffer was also used for elution of the target, and the flow rate was 10 ml/min. Relevant fractions were selected and pooled based on the chromatogram and SDS-PAGE analysis.

Example 3: Cloning and Expression of RNase from *Acremonium alcalophilum* and *Trichoderma harzianum*

Strains

*Escherichia coli* One Shot® TOP10 strain purchased from Thermo Fisher Scientific (Life Technologies Europe BV, Nrum, Denmark) was used to propagate expression vector encompassing ribonuclease coding sequences.

*Aspergillus oryzae* MT3568 strain was used for heterologous expression of the ribonuclease polypeptides. The *A. oryzae* MT3568 strain is an amdS (acetamidase) disrupted gene derivative of *A. oryzae* JaL355 strain (described in WO 2002/40694) in which pyrG auxotrophy was restored by disrupting the *A. oryzae* acetamidase (amdS) gene with the pyrG gene.

*Acremonium alcalophilum* CBS114.92 was purchased from CBS-KNAW (Fungal Biodiversity Centre, Utrecht, The Netherlands). According to Central Bureau vor Schnimmelkulture, *Acremonium* alcalohilum CBS114.92 was isolated by A. Yoneda in 1984 from the sludge of pig feces compost near Tsukui Lake, Japan.

*Trichoderma harzianum* CBS223.93, originally named A00611, was deposited at the Centraalbureau voor Schimmelcultures, Ultrecht, The Netherlands under the code: CBS223.93. The strain was acquired from Swiss Ferment NG in 1968.

Media and Solutions

Horikoshi Agar Medium was Composed of:

1% (w/v) dextrose, 1% soluble starch, 0.5% (w/v) peptone, 0.5% (w/v) yeast extract, 0.02% (w/v) $MgSO_4.7H_2O$, 0.1% (w/v) $K_2HPO_4$, and 15 g (w/v) of Bacto-agar. 1% (w/v) $Na_2CO_3$ was added separately after sterilization.

PDA plates were composed of 39 g Potato Dextrose Agar (Sigma-Aldrich, Munich, Germany) and deionized water to 1000 ml. The medium was sterilized by autoclaving at 15 psi for 15 minutes (Bacteriological Analytical Manual, 8th Edition, Revision A, 1998).

LB-Bouillon was Composed of:

25 g of LB Bouillon (ref. L3152) (Sigma Aldrich, Darmstadt, Germany) and deionized water to 1000 ml. The medium was sterilized by autoclaving at 15 psi for 15 minutes (Bacteriological Analytical Manual, 8th Edition, Revision A, 1998).

Ampicillin LB-Agar Plates were Composed of:

37 g LB agar (ref. L3027) (Sigma Aldrich, Darmstadt, Germany), 5 g soluble starch, 0.01M $K_2PO_4$, 0.04% glucose, and deionized water to 1000 ml. The medium was sterilized by autoclaving at 15 psi for 15 minutes (Bacteriological Analytical Manual, 8th Edition, Revision A, 1998). The medium was cooled to 50° C. and 50 mM ampicillin was added.

COVE-N-Agar Plates were Composed of:

218 g of sorbitol, 25 g of agar powder, 50 mL of COVE salt solution, and deionized water to 1 liter. The medium was sterilized by autoclaving at 15 psi for 15 minutes (Bacteriological Analytical Manual, 8th Edition, Revision A, 1998). The medium was cooled to 50° C. and 10 mM acetamide, and Triton X-100 (50 µL/500 mL) were added. COVE salt solution was composed of: 26 g of $MgSO_4.7H_2O$, 26 g of KCL, 76 g of $KH_2PO_4$, 50 mL of COVE trace metal solution, and deionized water to 1 liter. Solution was sterile filtered.

COVE Trace Metal Solution was Composed of:

0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionized water to 1 liter. Solution was sterile filtered.

DAP4C-1 Medium was Composed of:

0.5 g yeast extract, 10 g maltose, 20 g dextrose, 11 g $MgSO_4.7H_2O$, 1 g $KH_2PO_4$, 2 g $C_6H_8O_7.H_2O$, 5.2 g $K3PO_4.H_2O$, 1 mL Dowfax 63N10 (antifoaming agent), 2.5 g calcium carbonate, supplemented with 0.5 mL KU6 trace metal solution, and deionized water to 1000 mL. The medium was sterilized by autoclaving at 15 psi for 15 minutes (Bacteriological Analytical Manual, 8th Edition, Revision A, 1998). Before use, 3.5 mL of sterile 50% $(NH_4)2HPO_4$ and 5 mL of sterile 20% lactic acid were added per 150 ml of DAP4C-1 medium.

YP 2% Glucose Medium was Composed of:

10 g yeast extract, 20 g Bacto peptone, 20 g dextrose, and deionized water to 1000 ml. The medium was sterilized by autoclaving at 15 psi for 15 minutes (Bacteriological Analytical Manual, 8th Edition, Revision A, 1998).

KU6 Trace Metal Solution was Composed of:

6.8 g $ZnCl_2$, 2.5 g $CuSO_4.5H_2O$, 0.13 g $NiCl_2$, 13.9 g $FeSO_4.7H_2O$, 8.45 g $MnSO_4.H_2O$, 3 g $C_6H_8O_7.H_2O$, and deionized water to 1000 mL. Solution was sterile filtered.

Sequences Amplification and Cloning

RNase from *Acremonium alcalophilum* shown in SEQ ID NO 14 (mature polypeptide shown in SEQ ID NO 15):

The *Acremonium alcalophilum* strain JCM 7366 (ATCC 90507) was sequenced by JGI (https://genome.jgi.doe.gov/Acral2/Acral2.home.html) and the genome was assembled and annotated. 9521 gene models were identified in this genome assembly. The ribonuclease encoding polypeptide with SEQ ID NO 14, comprising a predicted extracellular secretion signal (1-17) and a predicted PFAM00545 domain (47-127) was identified among those sequences. For the preparation of *A. alcalophilum* genomic DNA the *A. alcalophilum* CBS114.92 strain was propagated on Horikoshi agar, pH9 for 7 days at 30° C.

RNase from *Trichoderma harzianum* shown in SEQ ID NO 69 (mature polypeptide shown in SEQ ID NO 72):

The *Trichoderma harzianum* strain A00611 was sequenced using Illumina sequencing paired-ends technology, the genome de novo assembly was produced using IDBA-UD v1.0.9 method (Peng, Y., et al. (2012) Bioinformatics) and the genome annotation generated with GeneMark v2.3c (Ter-Hovhannisyan, V., et al. (2008) Genome Res.). The ribonuclease encoding the polypeptide with SEQ ID NO 69, comprising a predicted extracellular secretion signal (1-15) and a predicted PFAM00545 domain (45-127), was identified within this assembly. For the preparation of *T. harzianum* genomic DNA the strain A00611 was inoculated onto a PDA plate and incubated for 8 days at 26° C. in the dark. Several mycelia-PDA plugs were inoculated into 500 ml shake flasks containing 100 ml of YP 2% glucose medium. The shake flasks were incubated for 5 days at 26° C. with shaking at 100 rpm for production of biomass.

Mycelia from *Acremonium alcalophilum*, harvested directly from agar and mycelia from *Trichoderma harzianum* harvested from shake flask were used for gDNA isolation according to the FastDNA® SPIN kit for Soil protocol (www.mpbio.com). The genomic DNA purified was eluted in 100 µl 10 mM TRIS buffer, 0.1 mM EDTA, pH 7.5 and stored at 4° C. until use. PCR amplifications of DNA encoding the RNase polypeptides (SEQ ID NO 14 for *A. alcalophilum*) and SEQ ID NO 69 for *Trichoderma harzianum* were carried out using Phusion High-Fidelity DNA polymerase (New England Biolabs, BioNordika Denmark NS, Herlev, Denmark) in a 25 µL volume reaction. The PCR reaction mix consisted of 5 µL Phusion reaction buffer HF (5×); 0.5 µL of PCR nucleotide Mix (10 mM); 2 µL of the following forward and reverse oligonucleotides (2.5 µM) (Alca166F/R for SEQ ID NO 13 amplification and MDQM1692F/R for SEQ ID NO 68 amplification (*T. harzianum* ribonuclease gene sequence):

```
Alca166-F
                                         (SEQ ID NO 26)
ACACAACTGGGGATCCACCATGCACTTGTCCGCCGTCTTC Alca166-R
                                         (SEQ ID NO 27)
CCCTCTAGATCTCGAGCCCAGCTTTCCCGAGTCTCTT MDQM1692-F
                                         (SEQ ID NO 74)
ACACAACTGGGGATCCACCATGAAGTTCCTCGGTCTCCTCTCC MDQM1692-R
                                         (SEQ ID NO 75)
AGATCTCGAGAAGCTTACTAAGAAGTACCGGCGCAAGCAA;
```

0.25 µL genomic DNA template (from *A. alcalophilum* or *T. harzianum*), 0.5 µL Phusion High-Fidelity DNA Polymerase cat. reference M0530 (2000 U/mL) (New England Biolabs, BioNordika Denmark NS, Herlev, Denmark); and PCR grade water up to 25 µL.

PCR reactions were incubated on a thermocycler T100 (Biorad, Hercules, Calif., USA) using the following program: initial denaturation of 2 min. at 98° C. followed by 35 cycles of 10 sec. at 98° C., 0.5 min. at 72° C. and ending up by a final elongation of 10 min at 72° C. Five µl of the PCR reactions were analyzed by 1% agarose gel electrophoresis using TAE buffer where DNA bands of approximately 500 base pair were observed. The remaining PCR reactions were purified using an ILLUSTRA™ GFX™ PCR DNA and Gel Band Purification Kit reference 28-9034 (GE Healthcare, UK) according to the manufacturer's instructions.

Cloning of the DNA sequences encoding the ribonucleases SEQ ID NO 15 for *A. alcalophilum* and SEQ ID NO 72 for *T. harzianum*. was made using InFusion HD Plus EcoDry Cloning system kit (Takara, Kusatsu, Japan) in expression vector pDAu109 (WO2005/042735) previously digested with BamHI and HindIII restriction enzymes and following the manufacturer's instructions. A 2.5 µL volume of the five-time diluted ligation mixtures was used to transform 25 µL of *E. coli* TOP10 (see strain description above) chemically competent cells (Life Technologies, Carlsbad, Calif., USA). Two colonies were selected from LB agar plates containing 50 µg of ampicillin per mL and cultivated overnight in 3 mL of LB medium supplemented with 100 µg of ampicillin per mL. Plasmid DNA was purified using a Qiagen Spin Miniprep kit (Cat. 27106) (QIAGEN GmbH, Hilden, Germany) according to the manufacturer's instructions. Ribonuclease sequences cloned by InFusion® were scrutinized for errors by Sanger DNA sequencing.

Protoplasts of *Aspergillus oryzae* MT3568 strain were prepared according to WO 95/002043. 100 µL of *A. oryzae* protoplasts were mixed with 1-3 µg of plasmids encoding ribonuclease polypeptide SEQ ID NO 15 and SEQ ID NO 72 and 270 µL of 60% PEG 4000 (Applichem, Darmstadt, Germany) (polyethylene glycol, molecular weight 4000), 10 mM $CaCl_2$), and 10 mM Tris-HCl pH 7.5 and gently mixed. The mixtures were incubated at 37° C. for 30 minutes and the protoplasts were spread onto COVE plates containing 10 mM acetamide. After incubation for 4-7 days at 37° C., spores of four colonies were inoculated into DAP4C-1 medium in 96-well X50 microtiter plate PS from Thermo Fisher Scientific (Life Technologies Europe BV, Nrum, Denmark) and covered with semi-permeable tape. After 4 days of static incubation at 30° C., the culture broths were analyzed by sodium dodecyl sulfate polyacrylamide gel electrophoresis in order to identify colonies producing the highest amount of ribonuclease polypeptides. Spores of the best transformants were spread onto COVE plates containing 0.01% TRITON® X-100 and 10 mM acetamide in order to isolate single colonies. The spreading was repeated twice in total on COVE plates containing 10 mM acetamide. The selected strains expressing the *Acremonium alcalophilum* SEQ ID NO: 15 and the *Trichoderma harzianum* SEQ ID NO: 72 were inoculated in 250 mL shake flasks with baffle containing 150 mL of DAP4C-1 supplemented with lactic acid and di-ammonium phosphate for 4 days at a temperature of 30° C. under 150 rpm agitation. Culture broths were harvested by filtration using a 0.2 µm filter device.

Example 4: Purification of the RNase from *Acremonium alcalophilum*

The *A. alcalophilum* RNase was purified by ion exchange chromatography by loading the filtered broth onto a Capto™ S column (ref. 17-5441-03) (GE Healthcare, Piscataway, N.J., USA) previously equilibrated in 50 mM acetate pH4.5 buffer. The column was washed with 3 CV 50 mM acetate pH4.5 buffer. Elution of bound proteins was carried out with a linear gradient 100% of 50 mM acetate with 1M NaCl pH4.5 over 5CV. Fractions of 10 mL were collected during the chromatography and an elution flow of 10 mL/min was observed during the chromatography. All fractions were analyzed by sodium dodecyl sulfate polyacrylamide gel electrophoresis and fractions containing the RNase were pooled. Quantification of the RNase was made using the A280/E280 method (Stoscheck, CM. Quantitation of Protein. Methods in Enzymology 182: 50-69. 1990).

Example 5: Cloning, Expression and Fermentation of an RNase from *Fusarium solani*

An RNase encoding gene belonging to the PFAM protein family PF00545 (R. D. Finn, et al., Nucleic Acids Research (2016), D44:D279-D285) was cloned from a strain of *Fusarium solani* that was isolated from an environmental sample collected in Denmark.

Chromosomal DNA was isolated from a pure culture of the *Fusarium solani* strain, and a sample of the DNA was sent to Exiqon NS, Vedbaek, Denmark, for whole genome sequencing. The genome sequence was subsequently assembled with the SPAdes Genome Assembler, v3.5.0, and annotated with the GeneMark v2.3c gene prediction software.

The set of peptide sequences predicted from the annotated genome were searched for similarity to the PF00545 domain, and the peptide with SEQ ID NO: 73 was found. The corresponding DNA sequence (SEQ ID NO: 70) was PCR amplified from genomic DNA isolated from *Fusarium solani* with gene-specific primers that also append a Kozak translation initiation sequence "TCACC" immediately 5' of the start codon, and cloned into the *Aspergillus* expression vector pMStr57 (WO 2004/032648) that had been digested with BamHI and XhoI.

The cloned RNase encoding gene was sequenced and confirmed to be identical to the corresponding gene found in the genome sequence, and transformed into the *Aspergillus oryzae* strain MT3568 (WO 2011/057140) by the methods described in Christensen et al., 1988, *Biotechnology* 6, 1419-1422 and WO 2004/032648. Transformants were selected during regeneration from protoplasts based on the ability, conferred by a selectable marker in the expression vector, to utilize acetamide as a nitrogen source, and were subsequently re-isolated twice under selection.

Production of the recombinant RNase was evaluated by culturing transformants in 96-well deep-well microtiter plates for 4 days at 30° C. in 0.25 ml of YPG medium (WO 05/066338) and DAP-4C-1 medium (WO 2012/103350) and monitoring recombinant expression by SDS-PAGE. For larger-scale production of the recombinant RNase, a single *Aspergillus* transformant was selected based on recombinant yield and was cultured in 500 ml baffled flasks containing 150 ml of DAP-4C-1 medium. The cultures were shaken on a rotary table at 150 RPM at a temperature of 30° C. for 4 days. The culture broth was subsequently separated from cellular material by passage through a 0.22 um filtration unit.

Example 6: Chromatographic Purification of the Recombinant RNases from *Fusarium solani* and *Trichoderma harzianum*

The pH of the filtered sample was adjusted to around pH 7.5 and 1.8M ammonium sulfate was added. The sample was applied to a 5 ml HiTrap™ Phenyl (HS) column on an Akta Explorer. Prior to loading, the column had been equilibrated in 5 column volumes (CV) of 50 mM HEPES+1.8M AMS pH 7. In order to remove unbound material, the column was washed with 5 CV of 50 mM HEPES+1.8M AMS pH 7. The target protein was eluted from the column into a 10 ml loop using 50 mM HEPES+20% isopropanol pH 7. From the loop, the sample was loaded onto a desalting column (HiPrep™ 26/10 Desalting), which had been equilibrated with 3CV of 50 mM HEPES+100 mM NaCl pH 7.0. The target protein was eluted with 50 mM HEPES+100 mM NaCl pH 7.0 and relevant fractions were selected and pooled based on the chromatogram. The flow rate was 5 ml/min.

Protein concentration in the final sample was estimated by measuring absorption at 280 nm.

Example 7: Performance of RNases in Model Detergent

Washing Experiment A

Five rinsed swatches with *Brevundimonas* sp. were mixed with five sterile Cotton WFK10A swatches in a 50 mL test tube and added 10 mL of detergent wash solution comprising the following detergent composition in the mentioned concentrations: model detergent A (EU, 3.3 g/L), was added together with 0.7 g/L soil (Pigmentschmutz, 09V, wfk, Krefeld, Germany) and RNases shown in SEQ ID NO 3, 6, 9, 12 and 15 (0.2 and 1 ppm) having activity in the synthetic oligonucleotide substrate assay (Assay I). Test tubes were placed in a Stuart rotator (Mini LOM) for 1 hour at 22° C. Swatches were rinsed twice with tap water and dried on filter paper over night. As a control, washes with the mentioned detergent and without addition of RNase was made in parallel. Remission (Rem) values at 460 nm were measured using a Color Eye (Macbeth Color Eye 7000 reflectance spectrophotometer). The measurements were made without UV in the incident light.

The so-called EU conditions referred to above, i.e. 3.3 g/L detergent and water with a hardness of 15° dH (Ca:Mg:NaHCO$_3$ 4:1:1.5), were used. The delta Rem values are shown in Table 3.

TABLE 3

Wash results of RNases

| RNases | Concentration | ΔRem (460 nm) |
|---|---|---|
| SEQ ID NO 3 | 1 | 4.8 |
| *Paenibacillus* sp-18057 | 0.2 | 3.7 |
| SEQ ID NO 6 | 1 | 2.0 |
| *Paenibacillus* sp-62770 | 0.2 | 2.1 |
| SEQ ID NO 9 | 1 | 5.4 |
| *Amycolatopsis azurea* | 0.2 | 2.6 |
| SEQ ID NO 12 | 1 | 4.9 |
| Environmental sample community E | 0.2 | 4.1 |
| SEQ ID NO 15 | 1 | 1.5 |
| *Acremonium alcalophilum* | 0.2 | 1.1 |

The present example shows the anti-greying effect of RNase in cotton swatches pre-grown with bacteria (donors). The observed effect is due to the deep cleaning effect of RNase, so that a reduction of soil adhesion to bacterial extracellular polymeric substances (EPS) is obtained. Importantly, the present example shows that RNase prevents transfer of soil between different textile items in a wash and thus allows dirty laundry to be washed with less dirty laundry. This ensures that the whiteness of the textiles is improved.

Washing Experiment B

Five rinsed swatches with *Staphylococcus xylosus* were added to a 50 mL test tube and 10 mL of detergent wash solution comprising the following detergent composition in the mentioned concentration was added: model detergent A (EU, 3.3 g/L) was added together with 0.7 g/L soil (Pigmentschmutz, 09V, wfk, Krefeld, Germany) and RNases shown in SEQ ID NO 3 or SEQ ID NO 64 (5 ppm) having activity in the synthetic oligonucleotide substrate assay (Assay I). Test tubes were placed in a Stuart rotator (Mini LOM) for 1 hour at 30° C. Swatches were rinsed twice with tap water and dried on filter paper over night. As control, washes with the mentioned detergent and without addition of RNase were made in parallel. Remission (Rem) values at 460 nm were measured using a Color Eye (Macbeth Color Eye 7000 reflectance spectrophotometer). The measurements were made without UV in the incident light.

EU conditions of 3.3 g/L detergent and water with a hardness of 15° dH (Ca:Mg:NaHCO$_3$ 4:1:1.5) were used. The delta Rem values are shown in Table 4.

TABLE 4

Wash results for RNases

| RNases | Concentration (ppm) | ΔRem (460 nm) |
|---|---|---|
| SEQ ID NO 3 | 5 | 4.7 |
| *Paenibacillus* sp-18057 | | |
| SEQ ID NO 64 | 5 | 4.4 |
| *Paenibacillus* sp-18006 | | |

The results of wash experiment A and B shows the anti-greying effect of RNase in cotton swatches pre-grown with bacteria (donors). The observed effect is due to the deep cleaning effect of RNase, a reduction of soil adhesion to bacterial extracellular polymeric substances (EPS) is obtained. Importantly, the present example shows that RNase will prevent transfer of soil between different textile items in a wash and thus enable that dirty laundry can be washed with less dirty laundry. This ensures that the whiteness of the textile is improved.

Example 8: Reduction of Nucleic Acids from Real Items Extract by RNases

In a real consumer laundry study twelve socks from twelve different pairs (one sock per pair) were used (Warwick Equest). Six groups of 2 socks from 2 different pairs were formed and tested for RNase effect. From each sock a sampling of eight 2 cm diameter swatches were randomly cut, four from the sole part and four from the heel. For each part of the socks one swatch was added to a 50 ml test tube. For every group 4 test tubes with 4 swatches each were obtained, in total 24 tubes and 96 swatches. To the test tubes 10 mL of detergent wash solution was added comprising the following detergent composition: one tube with model detergent A (EU, 3.3 g/L) and no enzyme (control) and three tubes with model detergent A (EU, 3.3 g/L) and RNases shown in SEQ ID NO 64 or SEQ ID NO 72 (1 ppm) having activity in the synthetic oligonucleotide substrate assay (Assay 1). EU conditions of 3.3 g/L detergent and water with a hardness of 15° dH (Ca:Mg:NaHCO$_3$ 4:1:1.5) were used. Test tubes were placed in a Stuart rotator (Mini LOM) for 1 hour at 30° C. Next, the swatches were rinsed in water hardness 15° dH. To remove the water excess, the swatches were transferred to a Sartorius Vivaspin® 20 and spun for 5 min at 4000 RCF.

For extraction, the centrifuged swatches were transferred to a 50 mL DNAse-RNase free tubes (Sarstedt) and 4 ml RNase-free buffer (0.1% v/v DEPC, 10 mM EDTA, 0.9% NaCl pH 4.5) was added. The tubes were placed in a Stuart rotator (Mini LOM) for 1 hour at room temperature. A sample of 100 µl extract for each tube was added to 100 µl Quant-IT™ RiboGreen® (Thermofisher) reagent as recommended by the supplier protocol. Endpoint fluorescence was measured at 22° C. in a Clariostar microplate reader (excitation 500 nm, emission at 525 nm).

The results are presented below as a percentage fluorescence signal reduction between the control and the RNase samples.

TABLE 5

| RNases | Concentration (ppm) | % RFU reduction |
|---|---|---|
| No RNase (Control) | — | — |
| SEQ ID NO 64 Paenibacillus sp-18006 | 1 | 7 |
| SEQ ID NO 72 Trichoderma harzianum | 1 | 39 |

The results of this experiment show that RNases can reduce the amount of nucleic acids present in real consumer laundry items.

Example 9: RNase Activity

RNase was diluted in water hardness 15° dH or model detergent B (EU, 3.3 g/L) to obtain a concentration of 0.1 ppm and 1 ppm, respectively, and 5 µl of the substrate was added to 95 µl of the RNase sample. Model detergent B wash liquor (100%) was prepared by dissolving 3.33 g/l of model detergent B containing 7.2% LAS, 6.6% AEO Biosoft N25-7 (NI), 4.2% AEOS (SLES), 6% MPG (mono propylene glycol), 3% ethanol, 3% TEA (triethanolamine), 2.75% cocoa soap, 2.75% soya soap, 2% glycerol, 1.2% sodium hydroxide, 2% sodium citrate, 1% sodium formiate, 0.2% DTMPA and 0.2% PCA (Propenoic acid). All percentages are w/w (weight/weight).

A kinetic curve was measured for 10 min at 22° C. using a Spectramax microplate reader, Molecular Devices (excitation 490 nm, emission at 520 nm). Tables 6a and 6b below show RNase activity measured in water or in model detergent B.

TABLE 6a

Enzyme activity in water (RFU after 10 min)

| RNase SEQ ID NO | RNase activity in water, hardness 15° dH at 0.1 ppm (RFU) |
|---|---|
| 67 | 724 |
| 59 | 658 |
| 58 | 666 |
| 57 | 623 |
| 64 | 684 |
| 3 | 590 |
| 15 | 635 |
| 63 | 667 |
| 6 | 639 |
| 65 | 626 |
| 9 | 633 |
| 66 | 564 |
| 62 | 523 |
| 61 | 263 |
| 73 | 387 |
| 60 | 144 |
| 72 | 146 |

TABLE 6b

Enzyme activity in model detergent B (RFU after 10 min)

| RNase SEQ ID NO | RNase activity in Model B 3.3 g/l at 1 ppm (RFU) |
|---|---|
| 67 | 308 |
| 3 | 622 |
| 15 | 688 |
| 63 | 106 |
| 9 | 344 |
| 73 | 617 |
| 60 | 667 |
| 72 | 602 |

Example 10: Construction of Clades and Phylogenetic Trees

The ribonuclease domain includes the polypeptides of the invention having RNase activity and comprises the Barnase domain as well as the clusters such as the clades.

A phylogenetic tree was constructed with polypeptide sequences containing a Barnase domain, as defined in PFAM (PF000545, Pfam version 31.0 Finn (2016) *Nucleic Acids Research*, Database Issue 44:D279-D285). The phylogenetic tree was constructed from a multiple alignment of mature polypeptide sequences containing at least one Barnase domain. The sequences were aligned using the MUSCLE algorithm version 3.8.31 (Edgar, 2004. *Nucleic Acids Research* 32(5): 1792-1797), and the trees were constructed using FastTree version 2.1.8 (Price et al., 2010, *PloS one* 5(3)) and visualized using iTOL (Letunic & Bork, 2007. *Bioinformatics* 23(1): 127-128).

The polypeptides in Barnase can be separated into multiple distinct sub-clusters, or clades, where we denoted the clades listed below. Distinct motifs for each clade are described in detail below.

Generation of EYTV Clade

The EYTV clade comprises Barnase polypeptides of bacterial origin, having RNase activity and comprising the motif example EYTV (SEQ ID NO: 28), corresponding to positions 93 to 96 of SEQ ID NO 9 *A. azurea*, where E (corresponding to position 93 of SEQ ID NO 9) is fully conserved in the clade.

In one embodiment, a polypeptide of this clade may comprise the extended motif YXEYTVXTPXXXXRGXRR (SEQ ID NO: 78), wherein each X may independently be any naturally occurring amino acid.

The structure of the reference enzyme RNase Sa3 from *Streptomyces aureofaciens* (SEQ ID: 76) consists of a hydrophobic core including a central five-stranded twisted antiparallel beta-sheet, and the motif EYTV corresponds to part of the second N-terminal beta strand (residues 99-102 of SEQ ID:76) of the central beta sheet. (*J. Biol. Chem.* 2002; 277:47325-30). Amino acid changes that destroy hydrogen bonding between the beta strands in the beta-sheet decrease the overall enzyme stability. The Glu (E) residue of the EYTV motif acts as the general base and is believed to be essential for catalysis.

Generation of EAD Clade

The EAD clade comprises Barnase polypeptides of bacterial origin, having RNase activity and comprising the motif example [YRF]E[AYFWC]D (SEQ ID NO: 29), corresponding to positions 100 to 103 of SEQ ID NO 3

*Paenibacillus* sp-18057 where E (corresponding to position 101 of SEQ ID NO 3) is fully conserved in the EAD clade.

In one embodiment, a polypeptide of this clade may comprise the extended motif [WY][YRF]E[AYFWC]D[IV] (SEQ ID NO: 79).

The polypeptides of this clade may also comprise the motif IGGD (SEQ ID NO: 30), corresponding to positions 79 to 82 of SEQ ID NO 3.

In one embodiment, a polypeptide of this clade with the motif IGGD may comprise the extended motif GXXIGGDXFXN (SEQ ID NO: 80), wherein each X may independently be any naturally occurring amino acid.

The structure of the reference enzyme Barnase from *B. amyloliquifaciens* (SEQ ID: 34) consists of a hydrophobic core including a central five-stranded twisted antiparallel beta-sheet, and the motif IGGD corresponds to part of the first N-terminal beta strand (residues 98-101 of SEQ ID:34) and the EAD motif to part the second beta strand (residues 120-122 of SEQ ID:34) of the central beta sheet. (*Nature* 1982 May 13; 297:162-164). Amino acid changes that destroy hydrogen bonding between the beta strands in the beta-sheet decrease the overall enzyme stability. (*J Mol Biol.* 1992 Jun. 5; 225(3):585-9). The Glu (E) residue of the EAD motif acts as the general base and is believed to be essential for catalysis.

Generation of YPH clade

The YPH clade comprises Barnase polypeptides of fungal origin, having RNase activity and comprising the motif example YPH (SEQ ID NO: 31), corresponding to positions 45 to 47 of SEQ ID NO 15 *Acromonium alcalophilum* where all three amino acids are fully conserved in the clade.

In one embodiment, a polypeptide of this clade with the motif YPH may comprise the extended motif YPHX[YFA]X[ND]XE (SEQ ID NO: 81), where each X may independently be any naturally occurring amino acid.

The polypeptides of this clade may also comprise the motif DRV (SEQ ID NO:33), corresponding to positions 82 to 84 of SEQ ID NO 15 where R (corresponding to position 83 of SEQ ID NO 9) is fully conserved in the clade.

In one embodiment, a polypeptide of this clade with the DRV motif may comprise the extended motif PGXDRV (SEQ ID NO: 82), where X may be any naturally occurring amino acid.

The polypeptides of this clade may also comprise the motif HTGA (SEQ ID NO: 32), corresponding to positions 99 to 102 of SEQ ID NO 15.

In one embodiment, a polypeptide of this clade with the motif HTGA may comprise the extended motif THTGA[SR]G (SEQ ID NO: 83).

An alignment of some of the polypeptides of the invention (SEQ ID NO 3, 6, 9, 12 and 15) is shown in FIG. 1.

The structure of the reference enzyme RNase F1 from *Gibberella fujikuroi* (SEQ ID: 77) consists of a hydrophobic core including a central five-stranded twisted antiparallel beta-sheet. The motif YPH corresponds to part of the first N-terminal beta strand (residues 63-65 of SEQ ID:77), and the DRV motif to part of the third beta strand (residues 100-102 of SEQ ID:77) of the central beta sheet (*J Mol Biol.* 1993; 230(3):979-96). The HTGA motif corresponds to a turn region in the RNase F1 structure (residues 116-119 of SEQ ID:77) and the histidine residue of the HTGA motif is believed to be essential for catalytic activity of the enzyme. Amino acid changes that destroy hydrogen bonding between the beta strands in the beta-sheet decrease the overall enzyme stability. (*J Mol Biol.* 1992 Jun. 5; 225(3):585-9).

The invention claimed is:

1. A recombinant host cell comprising a polynucleotide encoding a polypeptide of the clade EYTV, EAD or YPH having RNase activity, operably linked to one or more control sequences that direct the production of the polypeptide, wherein the polypeptide is selected from the group consisting of:

(a) a polypeptide having at least 95% sequence identity to the polypeptide of SEQ ID NO: 57;

(b) a polypeptide comprising the polypeptide of (a) and an N-terminal and/or C-terminal His-tag and/or HQ-tag;

(c) a polypeptide comprising the polypeptide of (a) and an N-terminal and/or C-terminal extension of between 1 and 10 amino acids; and (d) a fragment of the polypeptide of SEQ ID NO: 57 having RNase activity and at least 90% of the length of SEQ ID NO: 57.

2. The recombinant host cell of claim 1, which comprises multiple copies of the polynucleotide.

3. The recombinant host cell of claim 1, which is selected from the group consisting of *Bacillus, Campylobacter, Clostridium, E. coli, Enterococcus, Flavobacterium, Fusobacterium, Geobacillus, Helicobacter, Ilyobacter, Lactobacillus, Lactococcus, Neisseria, Oceanobacillus, Pseudomonas, Salmonella, Staphylococcus, Streptococcus, Streptomyces*, and *Ureaplasma* cells.

4. The recombinant host cell of claim 1, which is selected from the group consisting of *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis* cells.

5. The recombinant host cell of claim 1, which is selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, and *Trichoderma* cells.

6. The recombinant host cell of claim 1, which is selected from the group consisting of *Aspergillus awamori, Aspergillus foetidus, Aspergillus fumigatus, Aspergillus japonicus, Aspergillus nidulans, Aspergillus niger, Aspergillus* otyzae, *Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium* imps, *Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium solani, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium* purpurogenum, *Phanerochaete chrysosporium, Phlebia radiata, Pleurotus* etyngii, *Thielavia terrestris, Trametes villosa, Trametes versicolor, Trichoderma harzianum, Trichoderma koningii, Trichoderma longibrachiatum, Trichoderma reesei*, and *Trichoderma viride* cells.

7. A method of producing a polypeptide having RNase activity, comprising cultivating the host cell of claim 1 under conditions conducive for production of the polypeptide.

8. A method of producing a polypeptide having RNase activity, comprising cultivating the host cell of claim 2 under conditions conducive for production of the polypeptide.

9. The recombinant host cell of claim 1, wherein the polypeptide has at least 97% sequence identity to the polypeptide of SEQ ID NO: 57.

10. The recombinant host cell of claim 1, wherein the polypeptide comprises the amino acid sequence of SEQ ID NO: 57.

11. The recombinant host cell of claim 1, wherein the polypeptide is a fragment of the polypeptide of SEQ ID NO: 57 having RNase activity and at least 90% of the length of SEQ ID NO: 57.

12. A method of producing a polypeptide having RNase activity, comprising cultivating the host cell of claim 3 under conditions conducive for production of the polypeptide.

13. A method of producing a polypeptide having RNase activity, comprising cultivating the host cell of claim 4 under conditions conducive for production of the polypeptide.

14. A method of producing a polypeptide having RNase activity, comprising cultivating the host cell of claim 5 under conditions conducive for production of the polypeptide.

15. A method of producing a polypeptide having RNase activity, comprising cultivating the host cell of claim 6 under conditions conducive for production of the polypeptide.

16. A method of producing a polypeptide having RNase activity, comprising cultivating the host cell of claim 9 under conditions conducive for production of the polypeptide.

17. A method of producing a polypeptide having RNase activity, comprising cultivating the host cell of claim 10 under conditions conducive for production of the polypeptide.

18. A method of producing a polypeptide having RNase activity, comprising cultivating the host cell of claim 11 under conditions conducive for production of the polypeptide.

* * * * *

SEQUENCE LISTING

```
<160> NUMBER OF SEQ ID NOS: 83

<210> SEQ ID NO 1
<211> LENGTH: 522
<212> TYPE: DNA
<213> ORGANISM: Paenibacillus sp.
<220> FEATURE:
<221> NAME/KEY: CDS
<222> LOCATION: (1)..(519)
<220> FEATURE:
<221> NAME/KEY: sig_peptide
<222> LOCATION: (1)..(87)
<220> FEATURE:
<221> NAME/KEY: mat_peptide
<222> LOCATION: (88)..(519)

<400> SEQUENCE: 1 atg agc gaa cga atc agg aaa gca tgg agg cgc ttc gcg gtt ccg acg      48
Met Ser Glu Arg Ile Arg Lys Ala Trp Arg Arg Phe Ala Val Pro Thr
            -25                 -20                 -15 tta gcc gcg atc gtg gcg gcg att acg atg ctg ctg gca ggc tgc ggg      96
Leu Ala Ala Ile Val Ala Ala Ile Thr Met Leu Leu Ala Gly Cys Gly
        -10                  -5                  -1   1 cag atc ggc gtc gat tcg ccg caa gga atc gcg tct cat tcg gcg gag     144
Gln Ile Gly Val Asp Ser Pro Gln Gly Ile Ala Ser His Ser Ala Glu
      5                  10                  15 gct ccc ggg acg caa gac gtt tcc cgg caa gct ccg ctc acc ggt ttt     192
Ala Pro Gly Thr Gln Asp Val Ser Arg Gln Ala Pro Leu Thr Gly Phe
 20                  25                  30                  35 aag gaa gtc gcc gat tac atc cga agt tac gga gcg ctt ccg gac aat     240
Lys Glu Val Ala Asp Tyr Ile Arg Ser Tyr Gly Ala Leu Pro Asp Asn
```

```
                40                  45                  50
ttc ata acg aag aag gaa gcg gaa cgg ctg gga tgg gta ccc tcc gag      288
Phe Ile Thr Lys Lys Glu Ala Glu Arg Leu Gly Trp Val Pro Ser Glu
            55                  60                  65 ggc aac ctg ggc aag gtg gcg ccg ggc aag agc atc gga ggc gac cga      336
Gly Asn Leu Gly Lys Val Ala Pro Gly Lys Ser Ile Gly Gly Asp Arg
        70                  75                  80 ttc ggc aat cgg gag ggg ctg ctg ccc aag gag aaa aac cgg atc tgg      384
Phe Gly Asn Arg Glu Gly Leu Leu Pro Lys Glu Lys Asn Arg Ile Trp
    85                  90                  95 tac gag gcg gac atc aac tat gaa ggc gga acg agg ggc gcg gat cgg      432
Tyr Glu Ala Asp Ile Asn Tyr Glu Gly Gly Thr Arg Gly Ala Asp Arg
100                 105                 110                 115 atc gta ttc tcg aat gac gga ttg atc tat atg acg acc gac cat tac      480
Ile Val Phe Ser Asn Asp Gly Leu Ile Tyr Met Thr Thr Asp His Tyr
                120                 125                 130 cgg tcg ttc acc gat att acg gaa gga ggt ccg gac cct tga              522
Arg Ser Phe Thr Asp Ile Thr Glu Gly Gly Pro Asp Pro
            135                 140

<210> SEQ ID NO 2
<211> LENGTH: 173
<212> TYPE: PRT
<213> ORGANISM: Paenibacillus sp.

<400> SEQUENCE: 2

Met Ser Glu Arg Ile Arg Lys Ala Trp Arg Arg Phe Ala Val Pro Thr
            -25                 -20                 -15

Leu Ala Ala Ile Val Ala Ala Ile Thr Met Leu Leu Ala Gly Cys Gly
        -10                  -5                  -1   1

Gln Ile Gly Val Asp Ser Pro Gln Gly Ile Ala Ser His Ser Ala Glu
    5                   10                  15

Ala Pro Gly Thr Gln Asp Val Ser Arg Gln Ala Pro Leu Thr Gly Phe
20                  25                  30                  35

Lys Glu Val Ala Asp Tyr Ile Arg Ser Tyr Gly Ala Leu Pro Asp Asn
                40                  45                  50

Phe Ile Thr Lys Lys Glu Ala Glu Arg Leu Gly Trp Val Pro Ser Glu
            55                  60                  65

Gly Asn Leu Gly Lys Val Ala Pro Gly Lys Ser Ile Gly Gly Asp Arg
        70                  75                  80

Phe Gly Asn Arg Glu Gly Leu Leu Pro Lys Glu Lys Asn Arg Ile Trp
    85                  90                  95

Tyr Glu Ala Asp Ile Asn Tyr Glu Gly Gly Thr Arg Gly Ala Asp Arg
100                 105                 110                 115

Ile Val Phe Ser Asn Asp Gly Leu Ile Tyr Met Thr Thr Asp His Tyr
                120                 125                 130

Arg Ser Phe Thr Asp Ile Thr Glu Gly Gly Pro Asp Pro
            135                 140

<210> SEQ ID NO 3
<211> LENGTH: 144
<212> TYPE: PRT
<213> ORGANISM: Paenibacillus sp.

<400> SEQUENCE: 3

Gly Cys Gly Gln Ile Gly Val Asp Ser Pro Gln Gly Ile Ala Ser His
1                   5                   10                  15

Ser Ala Glu Ala Pro Gly Thr Gln Asp Val Ser Arg Gln Ala Pro Leu
```

```
                20                  25                  30
Thr Gly Phe Lys Glu Val Ala Asp Tyr Ile Arg Ser Tyr Gly Ala Leu
             35                  40                  45
Pro Asp Asn Phe Ile Thr Lys Lys Glu Ala Glu Arg Leu Gly Trp Val
 50                  55                  60
Pro Ser Glu Gly Asn Leu Gly Lys Val Ala Pro Gly Lys Ser Ile Gly
 65                  70                  75                  80
Gly Asp Arg Phe Gly Asn Arg Glu Gly Leu Leu Pro Lys Glu Lys Asn
                 85                  90                  95
Arg Ile Trp Tyr Glu Ala Asp Ile Asn Tyr Glu Gly Gly Thr Arg Gly
             100                 105                 110
Ala Asp Arg Ile Val Phe Ser Asn Asp Gly Leu Ile Tyr Met Thr Thr
             115                 120                 125
Asp His Tyr Arg Ser Phe Thr Asp Ile Thr Glu Gly Gly Pro Asp Pro
             130                 135                 140

<210> SEQ ID NO 4
<211> LENGTH: 438
<212> TYPE: DNA
<213> ORGANISM: Paenibacillus sp.
<220> FEATURE:
<221> NAME/KEY: CDS
<222> LOCATION: (1)..(435)
<220> FEATURE:
<221> NAME/KEY: sig_peptide
<222> LOCATION: (1)..(78)
<220> FEATURE:
<221> NAME/KEY: mat_peptide
<222> LOCATION: (79)..(435)

<400> SEQUENCE: 4 gtg tat att aaa aaa tgg cta ggt gct gta ctc att att ctt gcg acg      48
Val Tyr Ile Lys Lys Trp Leu Gly Ala Val Leu Ile Ile Leu Ala Thr
    -25                 -20                 -15 atg ctg gtc gca ggt tgt tca ctt gaa tcg cta act gta gat gat tcg      96
Met Leu Val Ala Gly Cys Ser Leu Glu Ser Leu Thr Val Asp Asp Ser
-10                  -5                  -1  1               5 acc cag act cag gct gtc ttg aac caa ttt gac gaa gtg gcc aat tat     144
Thr Gln Thr Gln Ala Val Leu Asn Gln Phe Asp Glu Val Ala Asn Tyr
             10                  15                  20 ctt gcc gag cat cag gag ctt ccg gat aat tat att acc aag aag gag     192
Leu Ala Glu His Gln Glu Leu Pro Asp Asn Tyr Ile Thr Lys Lys Glu
         25                  30                  35 gcc aga gct tta ggc tgg gaa cca agt gaa gga aat ctg caa gat gtg     240
Ala Arg Ala Leu Gly Trp Glu Pro Ser Glu Gly Asn Leu Gln Asp Val
 40                  45                  50 gcc cca ggc aaa agt atc ggc ggt gat att ttt cag aat cgg gaa ggc     288
Ala Pro Gly Lys Ser Ile Gly Gly Asp Ile Phe Gln Asn Arg Glu Gly
 55                  60                  65                  70 ctg tta ccc aag aaa aag gga aga acg tgg tac gag gca gat atc aat     336
Leu Leu Pro Lys Lys Lys Gly Arg Thr Trp Tyr Glu Ala Asp Ile Asn
             75                  80                  85 tat tcg ggt gga acc cgg ggg agt gac cga atc ctc tat tcc agt gat     384
Tyr Ser Gly Gly Thr Arg Gly Ser Asp Arg Ile Leu Tyr Ser Ser Asp
             90                  95                 100 ggc tta ata tac aag aca acc gat cat tat cgc acg ttt gaa caa atc     432
Gly Leu Ile Tyr Lys Thr Thr Asp His Tyr Arg Thr Phe Glu Gln Ile
         105                 110                 115 aaa tga                                                              438
Lys
```

<210> SEQ ID NO 5
<211> LENGTH: 145
<212> TYPE: PRT
<213> ORGANISM: Paenibacillus sp.

<400> SEQUENCE: 5

Val Tyr Ile Lys Lys Trp Leu Gly Ala Val Leu Ile Ile Leu Ala Thr
    -25                 -20                 -15
Met Leu Val Ala Gly Cys Ser Leu Glu Ser Leu Thr Val Asp Asp Ser
-10                  -5                  -1   1                   5
Thr Gln Thr Gln Ala Val Leu Asn Gln Phe Asp Glu Val Ala Asn Tyr
                10                  15                  20
Leu Ala Glu His Gln Glu Leu Pro Asp Asn Tyr Ile Thr Lys Lys Glu
            25                  30                  35
Ala Arg Ala Leu Gly Trp Glu Pro Ser Glu Gly Asn Leu Gln Asp Val
        40                  45                  50
Ala Pro Gly Lys Ser Ile Gly Gly Asp Ile Phe Gln Asn Arg Glu Gly
55                  60                  65                  70
Leu Leu Pro Lys Lys Lys Gly Arg Thr Trp Tyr Glu Ala Asp Ile Asn
                75                  80                  85
Tyr Ser Gly Gly Thr Arg Gly Ser Asp Arg Ile Leu Tyr Ser Ser Asp
            90                  95                  100
Gly Leu Ile Tyr Lys Thr Thr Asp His Tyr Arg Thr Phe Glu Gln Ile
        105                 110                 115
Lys

<210> SEQ ID NO 6
<211> LENGTH: 119
<212> TYPE: PRT
<213> ORGANISM: Paenibacillus sp.

<400> SEQUENCE: 6

Leu Thr Val Asp Asp Ser Thr Gln Thr Gln Ala Val Leu Asn Gln Phe
1               5                   10                  15
Asp Glu Val Ala Asn Tyr Leu Ala Glu His Gln Glu Leu Pro Asp Asn
            20                  25                  30
Tyr Ile Thr Lys Lys Glu Ala Arg Ala Leu Gly Trp Glu Pro Ser Glu
        35                  40                  45
Gly Asn Leu Gln Asp Val Ala Pro Gly Lys Ser Ile Gly Gly Asp Ile
    50                  55                  60
Phe Gln Asn Arg Glu Gly Leu Leu Pro Lys Lys Lys Gly Arg Thr Trp
65                  70                  75                  80
Tyr Glu Ala Asp Ile Asn Tyr Ser Gly Gly Thr Arg Gly Ser Asp Arg
                85                  90                  95
Ile Leu Tyr Ser Ser Asp Gly Leu Ile Tyr Lys Thr Thr Asp His Tyr
            100                 105                 110
Arg Thr Phe Glu Gln Ile Lys
        115

<210> SEQ ID NO 7
<211> LENGTH: 471
<212> TYPE: DNA
<213> ORGANISM: Amycolatopsis azurea
<220> FEATURE:
<221> NAME/KEY: CDS
<222> LOCATION: (1)..(468)
<220> FEATURE:
<221> NAME/KEY: sig_peptide

```
<222> LOCATION: (1)..(66)
<220> FEATURE:
<221> NAME/KEY: mat_peptide
<222> LOCATION: (67)..(468)

<400> SEQUENCE: 7 atg ttc aac cgt agg cgg atc acc gcc gcc ctg atc ggc ctg atc gtg    48
Met Phe Asn Arg Arg Arg Ile Thr Ala Ala Leu Ile Gly Leu Ile Val
        -20                 -15                 -10 ctg gtg ctc gca ggc tgg ttc gtc aag gac ggc atc agc ggt gac gac    96
Leu Val Leu Ala Gly Trp Phe Val Lys Asp Gly Ile Ser Gly Asp Asp
    -5                  -1  1                   5                  10 acg aag agc tcc tcg gct ccg gcg agt tcg tca gcc cag ccc aaa ccg   144
Thr Lys Ser Ser Ser Ala Pro Ala Ser Ser Ser Ala Gln Pro Lys Pro
                15                  20                  25 tcg ggc gcg gcc aag ggc aag gtc gcg ggc gag gag tcc ggt ctc ccg   192
Ser Gly Ala Ala Lys Gly Lys Val Ala Gly Glu Glu Ser Gly Leu Pro
            30                  35                  40 gtc aaa ccg ctc acg ggg ttg ccg tcg cag gcc tcc gac acc tgg aag   240
Val Lys Pro Leu Thr Gly Leu Pro Ser Gln Ala Ser Asp Thr Trp Lys
        45                  50                  55 ctc atc acc gcg ggc ggg ccg tac ccg tat ccg cgc aat gac gac gtc   288
Leu Ile Thr Ala Gly Gly Pro Tyr Pro Tyr Pro Arg Asn Asp Asp Val
    60                  65                  70 acc ttc cag aac cgg gag aag gtc ctg ccc gcc aag gat tcc ggc tac   336
Thr Phe Gln Asn Arg Glu Lys Val Leu Pro Ala Lys Asp Ser Gly Tyr
75                  80                  85                  90 tac cgg gag tac acg gtc aag acg ccg ggc agc ccg gat cgc ggg gcg   384
Tyr Arg Glu Tyr Thr Val Lys Thr Pro Gly Ser Pro Asp Arg Gly Ala
                95                  100                 105 agg cgg ctg gtg acc ggc acc ggc aag gag ctg tac tac acc gaa gac   432
Arg Arg Leu Val Thr Gly Thr Gly Lys Glu Leu Tyr Tyr Thr Glu Asp
            110                 115                 120 cac tac aag tcc ttc gtc gta gtg gac ccc agc cga tga                471
His Tyr Lys Ser Phe Val Val Val Asp Pro Ser Arg
        125                 130

<210> SEQ ID NO 8
<211> LENGTH: 156
<212> TYPE: PRT
<213> ORGANISM: Amycolatopsis azurea

<400> SEQUENCE: 8

Met Phe Asn Arg Arg Arg Ile Thr Ala Ala Leu Ile Gly Leu Ile Val
        -20                 -15                 -10

Leu Val Leu Ala Gly Trp Phe Val Lys Asp Gly Ile Ser Gly Asp Asp
    -5                  -1  1                   5                  10

Thr Lys Ser Ser Ser Ala Pro Ala Ser Ser Ser Ala Gln Pro Lys Pro
                15                  20                  25

Ser Gly Ala Ala Lys Gly Lys Val Ala Gly Glu Glu Ser Gly Leu Pro
            30                  35                  40

Val Lys Pro Leu Thr Gly Leu Pro Ser Gln Ala Ser Asp Thr Trp Lys
        45                  50                  55

Leu Ile Thr Ala Gly Gly Pro Tyr Pro Tyr Pro Arg Asn Asp Asp Val
    60                  65                  70

Thr Phe Gln Asn Arg Glu Lys Val Leu Pro Ala Lys Asp Ser Gly Tyr
75                  80                  85                  90

Tyr Arg Glu Tyr Thr Val Lys Thr Pro Gly Ser Pro Asp Arg Gly Ala
                95                  100                 105
```

-continued

```
Arg Arg Leu Val Thr Gly Thr Gly Lys Glu Leu Tyr Tyr Thr Glu Asp
            110                 115                 120

His Tyr Lys Ser Phe Val Val Asp Pro Ser Arg
            125                 130

<210> SEQ ID NO 9
<211> LENGTH: 134
<212> TYPE: PRT
<213> ORGANISM: Amycolatopsis azurea

<400> SEQUENCE: 9

Phe Val Lys Asp Gly Ile Ser Gly Asp Thr Lys Ser Ser Ala
1               5                   10                  15

Pro Ala Ser Ser Ala Gln Pro Lys Pro Ser Gly Ala Ala Lys Gly
                20                  25                  30

Lys Val Ala Gly Glu Glu Ser Gly Leu Pro Val Lys Pro Leu Thr Gly
            35                  40                  45

Leu Pro Ser Gln Ala Ser Asp Thr Trp Lys Leu Ile Thr Ala Gly Gly
        50                  55                  60

Pro Tyr Pro Tyr Pro Arg Asn Asp Val Thr Phe Gln Asn Arg Glu
65              70                  75                  80

Lys Val Leu Pro Ala Lys Asp Ser Gly Tyr Tyr Arg Glu Tyr Thr Val
                85                  90                  95

Lys Thr Pro Gly Ser Pro Asp Arg Gly Ala Arg Arg Leu Val Thr Gly
            100                 105                 110

Thr Gly Lys Glu Leu Tyr Tyr Thr Glu Asp His Tyr Lys Ser Phe Val
        115                 120                 125

Val Val Asp Pro Ser Arg
        130

<210> SEQ ID NO 10
<211> LENGTH: 549
<212> TYPE: DNA
<213> ORGANISM: Unknown
<220> FEATURE:
<223> OTHER INFORMATION: Xanthan alkaline community E
<220> FEATURE:
<221> NAME/KEY: CDS
<222> LOCATION: (1)..(546)
<220> FEATURE:
<221> NAME/KEY: sig_peptide
<222> LOCATION: (1)..(72)
<220> FEATURE:
<221> NAME/KEY: mat_peptide
<222> LOCATION: (73)..(546)

<400> SEQUENCE: 10 atg atg aag agc ctg ctt aga aaa agc ttc ggg ctg att ctg att ttt      48
Met Met Lys Ser Leu Leu Arg Lys Ser Phe Gly Leu Ile Leu Ile Phe
            -20                 -15                 -10 gcc gtc ttt ttc acc ttt tca gga tgc agt att ctg gat atc aat tat      96
Ala Val Phe Phe Thr Phe Ser Gly Cys Ser Ile Leu Asp Ile Asn Tyr
        -5                  -1  1                   5 gac gga cca gaa atg ccg aaa ctg gag gaa cct tca gaa ggc gaa atc     144
Asp Gly Pro Glu Met Pro Lys Leu Glu Glu Pro Ser Glu Gly Glu Ile
            10                  15                  20 ccg aat gat gaa atc ccg gat att gag att cct gaa gat gaa ata cct     192
Pro Asn Asp Glu Ile Pro Asp Ile Glu Ile Pro Glu Asp Glu Ile Pro
25                  30                  35                  40 gag ggt gaa tct tta atc att gaa gac ggg caa tat acg aga aag gat     240
Glu Gly Glu Ser Leu Ile Ile Glu Asp Gly Gln Tyr Thr Arg Lys Asp
                45                  50                  55
```

```
gaa gtt gcg gaa tac atc cat atc ttt gga agg ctt cca gag aac tac      288
Glu Val Ala Glu Tyr Ile His Ile Phe Gly Arg Leu Pro Glu Asn Tyr
            60                  65                  70 atc acg aaa aat gaa gcc atg gat ctt ggc tgg gat gca agc agc gga      336
Ile Thr Lys Asn Glu Ala Met Asp Leu Gly Trp Asp Ala Ser Ser Gly
        75                  80                  85 aat ctc tgg gac gtc acg gat gag atg agc atc ggt gga gac aga ttc      384
Asn Leu Trp Asp Val Thr Asp Glu Met Ser Ile Gly Gly Asp Arg Phe
    90                  95                 100 gga aac cgg gaa ggt ctt tta cct gaa gct tca ggc cgc aaa tgg tat      432
Gly Asn Arg Glu Gly Leu Leu Pro Glu Ala Ser Gly Arg Lys Trp Tyr
105                 110                 115                 120 gaa gca gat atc gat tat gag ggc gga aga cgt aat gca aag aga atc      480
Glu Ala Asp Ile Asp Tyr Glu Gly Gly Arg Arg Asn Ala Lys Arg Ile
                125                 130                 135 gta ttt tca gat gat ggg ctg atc tat tat aca gac gat cat tac gca      528
Val Phe Ser Asp Asp Gly Leu Ile Tyr Tyr Thr Asp Asp His Tyr Ala
            140                 145                 150 tcc ttt gaa aag ctg tac tga                                          549
Ser Phe Glu Lys Leu Tyr
        155
```

<210> SEQ ID NO 11
<211> LENGTH: 182
<212> TYPE: PRT
<213> ORGANISM: Unknown
<220> FEATURE:
<223> OTHER INFORMATION: Synthetic Construct

<400> SEQUENCE: 11

```
Met Met Lys Ser Leu Leu Arg Lys Ser Phe Gly Leu Ile Leu Ile Phe
            -20                 -15                 -10

Ala Val Phe Phe Thr Phe Ser Gly Cys Ser Ile Leu Asp Ile Asn Tyr
        -5                  -1  1                   5

Asp Gly Pro Glu Met Pro Lys Leu Glu Glu Pro Ser Glu Gly Glu Ile
    10                  15                  20

Pro Asn Asp Glu Ile Pro Asp Ile Glu Ile Pro Glu Asp Glu Ile Pro
25                  30                  35                  40

Glu Gly Glu Ser Leu Ile Ile Glu Asp Gly Gln Tyr Thr Arg Lys Asp
                45                  50                  55

Glu Val Ala Glu Tyr Ile His Ile Phe Gly Arg Leu Pro Glu Asn Tyr
            60                  65                  70

Ile Thr Lys Asn Glu Ala Met Asp Leu Gly Trp Asp Ala Ser Ser Gly
        75                  80                  85

Asn Leu Trp Asp Val Thr Asp Glu Met Ser Ile Gly Gly Asp Arg Phe
    90                  95                 100

Gly Asn Arg Glu Gly Leu Leu Pro Glu Ala Ser Gly Arg Lys Trp Tyr
105                 110                 115                 120

Glu Ala Asp Ile Asp Tyr Glu Gly Gly Arg Arg Asn Ala Lys Arg Ile
                125                 130                 135

Val Phe Ser Asp Asp Gly Leu Ile Tyr Tyr Thr Asp Asp His Tyr Ala
            140                 145                 150

Ser Phe Glu Lys Leu Tyr
        155
```

<210> SEQ ID NO 12
<211> LENGTH: 158
<212> TYPE: PRT

<213> ORGANISM: Unknown
<220> FEATURE:
<223> OTHER INFORMATION: Xanthan alkaline community E

<400> SEQUENCE: 12

```
Cys Ser Ile Leu Asp Ile Asn Tyr Asp Gly Pro Glu Met Pro Lys Leu
1               5                   10                  15

Glu Glu Pro Ser Glu Gly Ile Pro Asn Asp Glu Ile Pro Asp Ile
            20                  25                  30

Glu Ile Pro Glu Asp Glu Ile Pro Glu Gly Glu Ser Leu Ile Ile Glu
            35                  40                  45

Asp Gly Gln Tyr Thr Arg Lys Asp Glu Val Ala Glu Tyr Ile His Ile
        50                  55                  60

Phe Gly Arg Leu Pro Glu Asn Tyr Ile Thr Lys Asn Glu Ala Met Asp
65              70                  75                  80

Leu Gly Trp Asp Ala Ser Ser Gly Asn Leu Trp Asp Val Thr Asp Glu
                85                  90                  95

Met Ser Ile Gly Gly Asp Arg Phe Gly Asn Arg Glu Gly Leu Leu Pro
            100                 105                 110

Glu Ala Ser Gly Arg Lys Trp Tyr Glu Ala Asp Ile Asp Tyr Glu Gly
            115                 120                 125

Gly Arg Arg Asn Ala Lys Arg Ile Val Phe Ser Asp Asp Gly Leu Ile
        130                 135                 140

Tyr Tyr Thr Asp Asp His Tyr Ala Ser Phe Glu Lys Leu Tyr
145                 150                 155
```

<210> SEQ ID NO 13
<211> LENGTH: 463
<212> TYPE: DNA
<213> ORGANISM: Acremonium alcalophilum
<220> FEATURE:
<221> NAME/KEY: CDS
<222> LOCATION: (1)..(280)
<220> FEATURE:
<221> NAME/KEY: sig_peptide
<222> LOCATION: (1)..(51)
<220> FEATURE:
<221> NAME/KEY: mat_peptide
<222> LOCATION: (52)..(460)
<220> FEATURE:
<221> NAME/KEY: CDS
<222> LOCATION: (348)..(460)

<400> SEQUENCE: 13

```
atg cac ttg tcc gcc gtc ttc gtc tcc ctg ctg gcc gtc gtc gcc cag    48
Met His Leu Ser Ala Val Phe Val Ser Leu Leu Ala Val Val Ala Gln
        -15                 -10                 -5 gcc gcc ccc tcc ggc cag ctc gag aag cgc gcc act acc tgc ggc agc    96
Ala Ala Pro Ser Gly Gln Leu Glu Lys Arg Ala Thr Thr Cys Gly Ser
-1  1               5                   10                  15 acc tac tac tcg acg tcc cag gtc agt gcc gcg gct agt gct gcc tgc   144
Thr Tyr Tyr Ser Thr Ser Gln Val Ser Ala Ala Ala Ser Ala Ala Cys
                20                  25                  30 aac cac gtc cgg gcc ggt acc agg gcc ggt agc tcc acg tac cct cac   192
Asn His Val Arg Ala Gly Thr Arg Ala Gly Ser Ser Thr Tyr Pro His
            35                  40                  45 gcc tac aac aac tac gag ggc ttc aac ttc ccc atc agc ggc ccc tat   240
Ala Tyr Asn Asn Tyr Glu Gly Phe Asn Phe Pro Ile Ser Gly Pro Tyr
        50                  55                  60 cag ctc ttc cct ctc cgc acc agc ggc gtg tac act ggt g gtaggtggct  290
Gln Leu Phe Pro Leu Arg Thr Ser Gly Val Tyr Thr Gly
65                  70                  75
```

```
ttggcagagg cctttactag aagatgcgta gcgctgacga gaatcaaaaa cgcacag           347 gt  gcc cct ggc cct gac cgt gtc atc atc aac agg aac acc tgc gcc         394
    Gly Ala Pro Gly Pro Asp Arg Val Ile Ile Asn Arg Asn Thr Cys Ala
            80                  85                  90 atc gct ggt cag att acc cac act ggc gcg ccg ggc aac gcc ttt gtc         442
Ile Ala Gly Gln Ile Thr His Thr Gly Ala Pro Gly Asn Ala Phe Val
        95                  100                 105 ggc tgc agc ggc acc tac taa                                             463
Gly Cys Ser Gly Thr Tyr
        110
```

<210> SEQ ID NO 14
<211> LENGTH: 131
<212> TYPE: PRT
<213> ORGANISM: Acremonium alcalophilum

<400> SEQUENCE: 14

```
Met His Leu Ser Ala Val Phe Val Ser Leu Leu Ala Val Val Ala Gln
        -15                 -10                 -5

Ala Ala Pro Ser Gly Gln Leu Glu Lys Arg Ala Thr Thr Cys Gly Ser
-1  1               5                   10                  15

Thr Tyr Tyr Ser Thr Ser Gln Val Ser Ala Ala Ser Ala Ala Cys
                20                  25                  30

Asn His Val Arg Ala Gly Thr Arg Ala Gly Ser Ser Thr Tyr Pro His
            35                  40                  45

Ala Tyr Asn Asn Tyr Glu Gly Phe Asn Phe Pro Ile Ser Gly Pro Tyr
        50                  55                  60

Gln Leu Phe Pro Leu Arg Thr Ser Gly Val Tyr Thr Gly Gly Ala Pro
    65                  70                  75

Gly Pro Asp Arg Val Ile Ile Asn Arg Asn Thr Cys Ala Ile Ala Gly
80                  85                  90                  95

Gln Ile Thr His Thr Gly Ala Pro Gly Asn Ala Phe Val Gly Cys Ser
            100                 105                 110

Gly Thr Tyr
```

<210> SEQ ID NO 15
<211> LENGTH: 114
<212> TYPE: PRT
<213> ORGANISM: Acremonium alcalophilum

<400> SEQUENCE: 15

```
Ala Pro Ser Gly Gln Leu Glu Lys Arg Ala Thr Thr Cys Gly Ser Thr
1               5                   10                  15

Tyr Tyr Ser Thr Ser Gln Val Ser Ala Ala Ser Ala Ala Cys Asn
            20                  25                  30

His Val Arg Ala Gly Thr Arg Ala Gly Ser Ser Thr Tyr Pro His Ala
        35                  40                  45

Tyr Asn Asn Tyr Glu Gly Phe Asn Phe Pro Ile Ser Gly Pro Tyr Gln
    50                  55                  60

Leu Phe Pro Leu Arg Thr Ser Gly Val Tyr Thr Gly Gly Ala Pro Gly
65                  70                  75                  80

Pro Asp Arg Val Ile Ile Asn Arg Asn Thr Cys Ala Ile Ala Gly Gln
            85                  90                  95

Ile Thr His Thr Gly Ala Pro Gly Asn Ala Phe Val Gly Cys Ser Gly
        100                 105                 110

Thr Tyr
```

<210> SEQ ID NO 16
<211> LENGTH: 1549
<212> TYPE: DNA
<213> ORGANISM: Unknown
<220> FEATURE:
<223> OTHER INFORMATION: Xanthan alkaline community E
<220> FEATURE:
<221> NAME/KEY: CDS
<222> LOCATION: (501)..(1046)
<220> FEATURE:
<221> NAME/KEY: sig_peptide
<222> LOCATION: (501)..(572)
<220> FEATURE:
<221> NAME/KEY: mat_peptide
<222> LOCATION: (573)..(1046)

<400> SEQUENCE: 16

```
tgatgttaag atcgatcagg tccttcacaa cgggcagtgg tccctgtgaa gtccgttttt      60
cctgaggaag agcgccctgg tcaagtatgc tgcttgtgat gaaaagaatt ttgtctacca     120
tggtaagacc tccttgaagt gaacttagtt taattatgac attatattgc ctaaaactca     180
atgaacggat atggaacagg gttacagtaa gatgaacttt atatgatacg ctgtcaaaag     240
ggccatgatt taggtataat tcaggtaagg ggtgatatta tggacaatga gattgatcca     300
aggatcatgg ataatataac aaaagtctgc atctgcaaag ccatccccag aagcaaaata     360
aaggatgcca tcaggaaagg cgcggacagt gtggtcaaag tcaatgaagt caccggttca     420
ggccagggtg agtgtcgcgg aaggcgttgc gggctgaaaa taagggggct tattgacgga     480
tataagaacg gagagtgggc atg atg aag agc ctg ctt aga aaa agc ttc ggg     533
                        Met Met Lys Ser Leu Leu Arg Lys Ser Phe Gly
                                -20                         -15 ctg att ctg att ttt gcc gtc ttt ttc acc ttt tca gga tgc agt att     581
Leu Ile Leu Ile Phe Ala Val Phe Phe Thr Phe Ser Gly Cys Ser Ile
        -10                  -5                  -1  1 ctg gat atc aat tat gac gga cca gaa atg ccg aaa ctg gag gaa cct     629
Leu Asp Ile Asn Tyr Asp Gly Pro Glu Met Pro Lys Leu Glu Glu Pro
    5                  10                  15 tca gaa ggc gaa atc ccg aat gat gaa atc ccg gat att gag att cct     677
Ser Glu Gly Glu Ile Pro Asn Asp Glu Ile Pro Asp Ile Glu Ile Pro
20                  25                  30                  35 gaa gat gaa ata cct gag ggt gaa tct tta atc att gaa gac ggg caa     725
Glu Asp Glu Ile Pro Glu Gly Glu Ser Leu Ile Ile Glu Asp Gly Gln
                40                  45                  50 tat acg aga aag gat gaa gtt gcg gaa tac atc cat atc ttt gga agg     773
Tyr Thr Arg Lys Asp Glu Val Ala Glu Tyr Ile His Ile Phe Gly Arg
            55                  60                  65 ctt cca gag aac tac atc acg aaa aat gaa gcc atg gat ctt ggc tgg     821
Leu Pro Glu Asn Tyr Ile Thr Lys Asn Glu Ala Met Asp Leu Gly Trp
        70                  75                  80 gat gca agc agc gga aat ctc tgg gac gtc acg gat gag atg agc atc     869
Asp Ala Ser Ser Gly Asn Leu Trp Asp Val Thr Asp Glu Met Ser Ile
    85                  90                  95 ggt gga gac aga ttc gga aac cgg gaa ggt ctt tta cct gaa gct tca     917
Gly Gly Asp Arg Phe Gly Asn Arg Glu Gly Leu Leu Pro Glu Ala Ser
100                 105                 110                 115 ggc cgc aaa tgg tat gaa gca gat atc gat tat gag ggc gga aga cgt     965
Gly Arg Lys Trp Tyr Glu Ala Asp Ile Asp Tyr Glu Gly Gly Arg Arg
                120                 125                 130 aat gca aag aga atc gta ttt tca gat gat ggg ctg atc tat tat aca    1013
Asn Ala Lys Arg Ile Val Phe Ser Asp Asp Gly Leu Ile Tyr Tyr Thr
            135                 140                 145
```

-continued

```
gac gat cat tac gca tcc ttt gaa aag ctg tac tgattggagg agatagaatg    1066
Asp Asp His Tyr Ala Ser Phe Glu Lys Leu Tyr
        150                 155 aatagagtca tactcaatgg aaagagaatg atcacgcgtg aagttaccca tgcctacctc    1126
aaaagaaaat tcttcttccc ggacgactac ggcagaaatc tggatgcgct ctgggacctg    1186
ctcagtacta aagggaaaga cacagagatt gttctcgtcc atgccaatct catcacagag    1246
catcttgggc agtatggaca ttcactttg agggtctttg atgatcttaa cgaagaatcc     1306
aggcatgtga aggtcaccta tatgaactga cggttatgaa aagcgctca gcaaaggttc     1366 aggctggaaa atttatgggc tttggattct ttgcatagga tgagcatatg caaaataggt    1426
tataatagag agaaagggtt ggcgcttcga atgaagaaag agctgccaaa aaggagataa    1486
atatggaata taaatacctg aaaataagag aaatcataga gatgtttgaa gaagaggata    1546
ttt                                                                  1549
```

<210> SEQ ID NO 17
<211> LENGTH: 182
<212> TYPE: PRT
<213> ORGANISM: Unknown
<220> FEATURE:
<223> OTHER INFORMATION: Synthetic Construct

<400> SEQUENCE: 17

```
Met Met Lys Ser Leu Leu Arg Lys Ser Phe Gly Leu Ile Leu Ile Phe
                -20                 -15                 -10

Ala Val Phe Phe Thr Phe Ser Gly Cys Ser Ile Leu Asp Ile Asn Tyr
         -5                  -1  1                   5

Asp Gly Pro Glu Met Pro Lys Leu Glu Glu Pro Ser Glu Gly Glu Ile
     10                  15                  20

Pro Asn Asp Glu Ile Pro Asp Ile Glu Ile Pro Glu Asp Glu Ile Pro
25                  30                  35                  40

Glu Gly Glu Ser Leu Ile Ile Glu Asp Gly Gln Tyr Thr Arg Lys Asp
                 45                  50                  55

Glu Val Ala Glu Tyr Ile His Ile Phe Gly Arg Leu Pro Glu Asn Tyr
             60                  65                  70

Ile Thr Lys Asn Glu Ala Met Asp Leu Gly Trp Asp Ala Ser Ser Gly
         75                  80                  85

Asn Leu Trp Asp Val Thr Asp Glu Met Ser Ile Gly Gly Asp Arg Phe
     90                  95                 100

Gly Asn Arg Glu Gly Leu Leu Pro Glu Ala Ser Gly Arg Lys Trp Tyr
105                 110                 115                 120

Glu Ala Asp Ile Asp Tyr Glu Gly Gly Arg Arg Asn Ala Lys Arg Ile
                125                 130                 135

Val Phe Ser Asp Asp Gly Leu Ile Tyr Tyr Thr Asp His Tyr Ala
            140                 145                 150

Ser Phe Glu Lys Leu Tyr
        155
```

<210> SEQ ID NO 18
<211> LENGTH: 1438
<212> TYPE: DNA
<213> ORGANISM: Paenibacillus sp.
<220> FEATURE:
<221> NAME/KEY: CDS
<222> LOCATION: (501)..(935)
<220> FEATURE:
<221> NAME/KEY: sig_peptide
<222> LOCATION: (501)..(578)
<220> FEATURE:
<221> NAME/KEY: mat_peptide
<222> LOCATION: (579)..(935)
<220> FEATURE:
<221> NAME/KEY: misc_feature
<222> LOCATION: (955)..(1227)
<223> OTHER INFORMATION: Inhibitor

<400> SEQUENCE: 18

```
attaattgct ccgttgtagt ctctgcaggc aaaaccactt taatcgaatg tacccctatt      60
cgggcacatg cattgccttt cattcgtaca tacgtttctg atgagggatc atcaccaacc     120
aaaatagtcg ctagacaagg tgtaattcct ttctccttca acccggcaac cttcgcagtc     180
atctcttact tcataaagtc cgctaccgtt tgtcaattca acattagctt ctctgtactc     240
atgctcatca tcgcccttc caaataaaaa gaggcaagga aataaaactt ccttacctcg      300
gcccaggcgt acggcttgat tagacatcat atgctccctc acggttcacc gtgttcgcca     360
gttacatatg accatattac cttgatagta cttcattttg aaatgtacat caatcctttt     420
aactttagct atacttggaa ctgtgttcag attggtatat actttttga gttaagaaga      480 ttaaaaggag attataagca gtg tat att aaa aaa tgg cta ggt gct gta ctc    533
                      Val Tyr Ile Lys Lys Trp Leu Gly Ala Val Leu
                              -25                 -20 att att ctt gcg acg atg ctg gtc gca ggt tgt tca ctt gaa tcg cta      581
Ile Ile Leu Ala Thr Met Leu Val Ala Gly Cys Ser Leu Glu Ser Leu
-15                 -10                  -5                 -1  1 act gta gat gat tcg acc cag act cag gct gtc ttg aac caa ttt gac      629
Thr Val Asp Asp Ser Thr Gln Thr Gln Ala Val Leu Asn Gln Phe Asp
            5                  10                  15 gaa gtg gcc aat tat ctt gcc gag cat cag gag ctt ccg gat aat tat      677
Glu Val Ala Asn Tyr Leu Ala Glu His Gln Glu Leu Pro Asp Asn Tyr
        20                  25                  30 att acc aag aag gag gcc aga gct tta ggc tgg gaa cca agt gaa gga      725
Ile Thr Lys Lys Glu Ala Arg Ala Leu Gly Trp Glu Pro Ser Glu Gly
    35                  40                  45 aat ctg caa gat gtg gcc cca ggc aaa agt atc ggc ggt gat att ttt      773
Asn Leu Gln Asp Val Ala Pro Gly Lys Ser Ile Gly Gly Asp Ile Phe
50                  55                  60                  65 cag aat cgg gaa ggc ctg tta ccc aag aaa aag gga aga acg tgg tac      821
Gln Asn Arg Glu Gly Leu Leu Pro Lys Lys Lys Gly Arg Thr Trp Tyr
                70                  75                  80 gag gca gat atc aat tat tcg ggt gga acc cgg ggg agt gac cga atc      869
Glu Ala Asp Ile Asn Tyr Ser Gly Gly Thr Arg Gly Ser Asp Arg Ile
            85                  90                  95 ctc tat tcc agt gat ggc tta ata tac aag aca acc gat cat tat cgc      917
Leu Tyr Ser Ser Asp Gly Leu Ile Tyr Lys Thr Thr Asp His Tyr Arg
        100                 105                 110 acg ttt gaa caa atc aaa tgaccaaagg taggatggta tgaagacagt             965
Thr Phe Glu Gln Ile Lys
    115 aatcattgat ggaaatgata ttcatggaaa agaagagctg catgatattc ttcaggcgaa    1025 gctggggtta gatgactctt acgggcggaa tctcgatgcg ttatgggatg tcattacagg    1085 cttcatttca ataccactaa ccattcaatg ggtgaatttt gaggcagca gggctgtgct     1145 tggagaatac gctgatcagc tattggagtt aatgcgtgaa gcagaagaag agctggatca    1205 atttcaattg gatctgaaaa tgtaaaaacg aacgggcagt ccgctgagga ctgctttttt    1265 taatgtgcaa catgttccat gagacttccg ttaaggagtt aaggaatcca caggaggtga    1325
```

```
gggtcattcc caggaagtta ttgtacttca tttatgttct gtcactggtt agtctgacaa    1385
catcttgtgc aagcacgtcc acgaatgcag atgctgataa cggtctaagc gaa           1438
```

<210> SEQ ID NO 19
<211> LENGTH: 145
<212> TYPE: PRT
<213> ORGANISM: Paenibacillus sp.

<400> SEQUENCE: 19

```
Val Tyr Ile Lys Lys Trp Leu Gly Ala Val Leu Ile Ile Leu Ala Thr
    -25                 -20                 -15

Met Leu Val Ala Gly Cys Ser Leu Glu Ser Leu Thr Val Asp Asp Ser
-10                  -5                  -1   1                   5

Thr Gln Thr Gln Ala Val Leu Asn Gln Phe Asp Glu Val Ala Asn Tyr
                10                  15                  20

Leu Ala Glu His Gln Glu Leu Pro Asp Asn Tyr Ile Thr Lys Lys Glu
            25                  30                  35

Ala Arg Ala Leu Gly Trp Glu Pro Ser Glu Gly Asn Leu Gln Asp Val
40                  45                  50

Ala Pro Gly Lys Ser Ile Gly Gly Asp Ile Phe Gln Asn Arg Glu Gly
55                  60                  65                  70

Leu Leu Pro Lys Lys Lys Gly Arg Thr Trp Tyr Glu Ala Asp Ile Asn
                75                  80                  85

Tyr Ser Gly Gly Thr Arg Gly Ser Asp Arg Ile Leu Tyr Ser Ser Asp
            90                  95                  100

Gly Leu Ile Tyr Lys Thr Thr Asp His Tyr Arg Thr Phe Glu Gln Ile
        105                 110                 115

Lys
```

<210> SEQ ID NO 20
<211> LENGTH: 1522
<212> TYPE: DNA
<213> ORGANISM: Paenibacillus sp.
<220> FEATURE:
<221> NAME/KEY: CDS
<222> LOCATION: (501)..(1019)
<220> FEATURE:
<221> NAME/KEY: sig_peptide
<222> LOCATION: (501)..(587)
<220> FEATURE:
<221> NAME/KEY: mat_peptide
<222> LOCATION: (588)..(1019)
<220> FEATURE:
<221> NAME/KEY: misc_feature
<222> LOCATION: (1022)..(1315)
<223> OTHER INFORMATION: Inhibitor

<400> SEQUENCE: 20

```
tgtccggagg acaacagcag cgggtggcca tcgcgcgtgc catggcggtc gacccgcagg     60
tgctgttgtt cgatgagccg acctcggcgc tggaccccga attggtcggg gaggtgctga    120
aggtgatgaa gcagctggcc gctgaaggga tgacgatggc catcgtgacg cacgaaatga    180
aatttgccgc ggatgtggcc gatcacgttc ttctcatgga cgacgggcag atcatcgagc    240
aaggatctcc tcaagaggtg cttcatcatc cgaagactcc gcgagccgta caatttctca    300
atcgtctgca cggaaagtcg gaggaatgac gacgaacacc ccctaacggc caggtcctga    360
tcgaagacga ttcgatcggg gcctggccgt tgttctgcga ttgatctctc tttccccga    420 agaaagttat gtctatgata agaacaggga tccggtcgga ttcctgaaaa tagctcgaga    480
ggcatagaca aggagataag atg agc gaa cga atc agg aaa gca tgg agg cgc    533
```

```
                Met Ser Glu Arg Ile Arg Lys Ala Trp Arg Arg
                         -25                 -20
ttc gcg gtt ccg acg tta gcc gcg atc gtg gcg gcg att acg atg ctg   581
Phe Ala Val Pro Thr Leu Ala Ala Ile Val Ala Ala Ile Thr Met Leu
        -15                 -10                  -5 ctg gca ggc tgc ggg cag atc ggc gtc gat tcg ccg caa gga atc gcg   629
Leu Ala Gly Cys Gly Gln Ile Gly Val Asp Ser Pro Gln Gly Ile Ala
 -1   1                   5                      10 tct cat tcg gcg gag gct ccc ggg acg caa gac gtt tcc cgg caa gct   677
Ser His Ser Ala Glu Ala Pro Gly Thr Gln Asp Val Ser Arg Gln Ala
 15                  20                  25                  30 ccg ctc acc ggt ttt aag gaa gtc gcc gat tac atc cga agt tac gga   725
Pro Leu Thr Gly Phe Lys Glu Val Ala Asp Tyr Ile Arg Ser Tyr Gly
                 35                  40                  45 gcg ctt ccg gac aat ttc ata acg aag aag gaa gcg gaa cgg ctg gga   773
Ala Leu Pro Asp Asn Phe Ile Thr Lys Lys Glu Ala Glu Arg Leu Gly
             50                  55                  60 tgg gta ccc tcc gag ggc aac ctg ggc aag gtg gcg ccg ggc aag agc   821
Trp Val Pro Ser Glu Gly Asn Leu Gly Lys Val Ala Pro Gly Lys Ser
         65                  70                  75 atc gga ggc gac cga ttc ggc aat cgg gag ggg ctg ctg ccc aag gag   869
Ile Gly Gly Asp Arg Phe Gly Asn Arg Glu Gly Leu Leu Pro Lys Glu
     80                  85                  90 aaa aac cgg atc tgg tac gag gcg gac atc aac tat gaa ggc gga acg   917
Lys Asn Arg Ile Trp Tyr Glu Ala Asp Ile Asn Tyr Glu Gly Gly Thr
 95                 100                 105                 110 agg ggc gcg gat cgg atc gta ttc tcg aat gac gga ttg atc tat atg   965
Arg Gly Ala Asp Arg Ile Val Phe Ser Asn Asp Gly Leu Ile Tyr Met
                115                 120                 125 acg acc gac cat tac cgg tcg ttc acc gat att acg gaa gga ggt ccg  1013
Thr Thr Asp His Tyr Arg Ser Phe Thr Asp Ile Thr Glu Gly Gly Pro
            130                 135                 140 gac cct tgatgagcac aacgatcgaa ctgagacagt cggaagcgga tcgtcatgaa   1069
Asp Pro gacttgcacg aatggttgaa gcgggagctg gagctgcccg agacctacgg tcgcaacctt   1129
gatgcgctat gggattgcgt aaccgggtac ctgttgcgtc ctgtcgagat ccggtgggtg   1189
gccgactccg acgaaaggga gcgctattcc gccattctgg acgtattccg ggaagccgcg   1249
gaggagtacg acgacgttcg cttcgtgtat gtccaagagg gggcggagcc cggaggtact   1309
cgaacttgat gaatctgtac ggagccgatc atcatctgct ggtgctgagc gatgcgatcg   1369
aggccgacga gcatcggcat tctttcgttc aggtgacggt agcgctggag ggtgcgttcg   1429
agattcagat cggggggcag agcctggaga cggctggaat cgttgtcgat tccaacgtgc   1489
ggcatcgtct ggacggcgcg gggcgaccgc tcc                               1522

<210> SEQ ID NO 21
<211> LENGTH: 173
<212> TYPE: PRT
<213> ORGANISM: Paenibacillus sp.

<400> SEQUENCE: 21

Met Ser Glu Arg Ile Arg Lys Ala Trp Arg Arg Phe Ala Val Pro Thr
             -25                 -20                 -15

Leu Ala Ala Ile Val Ala Ala Ile Thr Met Leu Leu Ala Gly Cys Gly
         -10                  -5                  -1   1

Gln Ile Gly Val Asp Ser Pro Gln Gly Ile Ala Ser His Ser Ala Glu
              5                  10                  15
```

```
Ala Pro Gly Thr Gln Asp Val Ser Arg Gln Ala Pro Leu Thr Gly Phe
 20                  25                  30                  35

Lys Glu Val Ala Asp Tyr Ile Arg Ser Tyr Gly Ala Leu Pro Asp Asn
                 40                  45                  50

Phe Ile Thr Lys Lys Glu Ala Glu Arg Leu Gly Trp Val Pro Ser Glu
             55                  60                  65

Gly Asn Leu Gly Lys Val Ala Pro Gly Lys Ser Ile Gly Gly Asp Arg
         70                  75                  80

Phe Gly Asn Arg Glu Gly Leu Leu Pro Lys Glu Lys Asn Arg Ile Trp
 85                  90                  95

Tyr Glu Ala Asp Ile Asn Tyr Glu Gly Gly Thr Arg Gly Ala Asp Arg
100                 105                 110                 115

Ile Val Phe Ser Asn Asp Gly Leu Ile Tyr Met Thr Thr Asp His Tyr
                120                 125                 130

Arg Ser Phe Thr Asp Ile Thr Glu Gly Gly Pro Asp Pro
                135                 140
```

<210> SEQ ID NO 22
<211> LENGTH: 1471
<212> TYPE: DNA
<213> ORGANISM: Amycolatopsis azurea
<220> FEATURE:
<221> NAME/KEY: CDS
<222> LOCATION: (501)..(968)
<220> FEATURE:
<221> NAME/KEY: sig_peptide
<222> LOCATION: (501)..(566)
<220> FEATURE:
<221> NAME/KEY: mat_peptide
<222> LOCATION: (567)..(968)
<220> FEATURE:
<221> NAME/KEY: misc_feature
<222> LOCATION: (968)..(1321)
<223> OTHER INFORMATION: Inhibitor

<400> SEQUENCE: 22

```
ccgtcgtcga gggtgcccgc gccgtcgcag cccaggatca tcgggaactg ctcgggtttg      60
atgccgaccc cgcgcagcgt ccacaggtcg tgcatgttga ggctggctgc cttgacgttg     120
acccgcaccc agccttcggg cacctcgggc tcgggtcgct cgccgatcac gagcgagtcc     180
agcggctttt cggcgttggg ttcggaagcg taaacggcga acatgccagc aacctacccc     240
ggcccttccg gcgggaccac tggcccacga gcgtaggctt accgggtgtt caacgggctt     300
gctgactggt gggacggcgt cgagctgtgg ctcgcgcagg cccgtttccc gtgcagttc      360 gtactggtca tggtggttgt ggtgccgctg tgcctggtcg cggcctggtt gctcgacgcg     420
ctcttcggga aggtcgcccg ggtcttcggc gcggcccgcg atgcgaacga ctccgaccgg     480
tcctcctaag ctggcgaacc atg ttc aac cgt agg cgg atc acc gcc gcc ctg     533
                     Met Phe Asn Arg Arg Arg Ile Thr Ala Ala Leu
                                      -20                 -15 atc ggc ctg atc gtg ctg gtg ctc gca ggc tgg ttc gtc aag gac ggc       581
Ile Gly Leu Ile Val Leu Val Leu Ala Gly Trp Phe Val Lys Asp Gly
    -10                 -5                 -1   1                5 atc agc ggt gac gac acg aag agc tcc tcg gct ccg gcg agt tcg tca       629
Ile Ser Gly Asp Asp Thr Lys Ser Ser Ser Ala Pro Ala Ser Ser Ser
                10                  15                  20 gcc cag ccc aaa ccg tcg ggc gcg gcc aag ggc aag gtc gcg ggc gag       677
Ala Gln Pro Lys Pro Ser Gly Ala Ala Lys Gly Lys Val Ala Gly Glu
            25                  30                  35 gag tcc ggt ctc ccg gtc aaa ccg ctc acg ggg ttg ccg tcg cag gcc       725
Glu Ser Gly Leu Pro Val Lys Pro Leu Thr Gly Leu Pro Ser Gln Ala
```

```
                40                  45                  50
tcc gac acc tgg aag ctc atc acc gcg ggc ggg ccg tac ccg tat ccg    773
Ser Asp Thr Trp Lys Leu Ile Thr Ala Gly Gly Pro Tyr Pro Tyr Pro
 55                  60                  65 cgc aat gac gac gtc acc ttc cag aac cgg gag aag gtc ctg ccc gcc    821
Arg Asn Asp Asp Val Thr Phe Gln Asn Arg Glu Lys Val Leu Pro Ala
 70                  75                  80                  85 aag gat tcc ggc tac tac cgg gag tac acg gtc aag acg ccg ggc agc    869
Lys Asp Ser Gly Tyr Tyr Arg Glu Tyr Thr Val Lys Thr Pro Gly Ser
                 90                  95                 100 ccg gat cgc ggg gcg agg cgg ctg gtg acc ggc acc ggc aag gag ctg    917
Pro Asp Arg Gly Ala Arg Arg Leu Val Thr Gly Thr Gly Lys Glu Leu
            105                 110                 115 tac tac acc gaa gac cac tac aag tcc ttc gtc gta gtg gac ccc agc    965
Tyr Tyr Thr Glu Asp His Tyr Lys Ser Phe Val Val Val Asp Pro Ser
        120                 125                 130 cga tgagcgcggg caaggacgcg gcggacaagg cgttcgcccg gggcgcgtat         1018
Arg ccgcacctga tcgacggcac gcggacggtc gacaaggcct ccgcgctcga cgcgatcgcc   1078
gaagccctgt ccttccccga ctacttcggg aagaacctcg acgcgctcta cgactgcctc   1138
accgacctgt cctggctccc ggcggggag cacgtgctga tctggtccgg ttcctcggtg   1198
ctcaaggacc gcgacccgaa ggcctacctg gctgtccgga gcgtgctttc ggacgcgcag   1258
cgggcgctgg gtccgtccgg ggatcggacg gactcccggc gcctcaccgt cgtcctgcct   1318
gattaggccg tgtcctagtc ctcggggacc cagttcggct tgcgcttctg cgcgaaagcc   1378
gtgatgccct cctggccctc ttcgctcgcg aagaacccgg cggacagctt gttcatagcc   1438
tcgaagcctt cgccgggtgt cgcagggcgg ggc                               1471

<210> SEQ ID NO 23
<211> LENGTH: 156
<212> TYPE: PRT
<213> ORGANISM: Amycolatopsis azurea

<400> SEQUENCE: 23

Met Phe Asn Arg Arg Ile Thr Ala Ala Leu Ile Gly Leu Ile Val
        -20                 -15                 -10

Leu Val Leu Ala Gly Trp Phe Val Lys Asp Gly Ile Ser Gly Asp Asp
 -5                  -1  1                   5                  10

Thr Lys Ser Ser Ser Ala Pro Ala Ser Ser Ala Gln Pro Lys Pro
                 15                  20                  25

Ser Gly Ala Ala Lys Gly Lys Val Ala Gly Glu Glu Ser Gly Leu Pro
             30                  35                  40

Val Lys Pro Leu Thr Gly Leu Pro Ser Gln Ala Ser Asp Thr Trp Lys
         45                  50                  55

Leu Ile Thr Ala Gly Gly Pro Tyr Pro Tyr Pro Arg Asn Asp Asp Val
 60                  65                  70

Thr Phe Gln Asn Arg Glu Lys Val Leu Pro Ala Lys Asp Ser Gly Tyr
 75                  80                  85                  90

Tyr Arg Glu Tyr Thr Val Lys Thr Pro Gly Ser Pro Asp Arg Gly Ala
                 95                 100                 105

Arg Arg Leu Val Thr Gly Thr Gly Lys Glu Leu Tyr Tyr Thr Glu Asp
            110                 115                 120

His Tyr Lys Ser Phe Val Val Val Asp Pro Ser Arg
        125                 130
```

<210> SEQ ID NO 24
<211> LENGTH: 27
<212> TYPE: PRT
<213> ORGANISM: Artificial sequence
<220> FEATURE:
<223> OTHER INFORMATION: Bacillus clausii

<400> SEQUENCE: 24

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 25
<211> LENGTH: 8
<212> TYPE: PRT
<213> ORGANISM: Artificial sequence
<220> FEATURE:
<223> OTHER INFORMATION: poly histidine tail

<400> SEQUENCE: 25

His His His His His His Pro Arg
1               5

<210> SEQ ID NO 26
<211> LENGTH: 40
<212> TYPE: DNA
<213> ORGANISM: Artificial sequence
<220> FEATURE:
<223> OTHER INFORMATION: Primer

<400> SEQUENCE: 26
acacaactgg ggatccacca tgcacttgtc cgccgtcttc                          40

<210> SEQ ID NO 27
<211> LENGTH: 37
<212> TYPE: DNA
<213> ORGANISM: Artificial sequence
<220> FEATURE:
<223> OTHER INFORMATION: Primer

<400> SEQUENCE: 27
ccctctagat ctcgagccca gctttcccga gtctctt                             37

<210> SEQ ID NO 28
<211> LENGTH: 4
<212> TYPE: PRT
<213> ORGANISM: Artificial sequence
<220> FEATURE:
<223> OTHER INFORMATION: Motif

<400> SEQUENCE: 28

Glu Tyr Thr Val
1

<210> SEQ ID NO 29
<211> LENGTH: 4
<212> TYPE: PRT
<213> ORGANISM: Artificial sequence
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X=Y(Tyr), R (Arg) or F (Phe)
<220> FEATURE:
<221> NAME/KEY: MISC_FEATURE

```
<222> LOCATION: (3)..(3)
<223> OTHER INFORMATION: X=A (Ala), Y(Tyr), F (Phe), W (Trp) or C (Cys)

<400> SEQUENCE: 29

Xaa Glu Xaa Asp
1

<210> SEQ ID NO 30
<211> LENGTH: 4
<212> TYPE: PRT
<213> ORGANISM: Artificial sequence
<220> FEATURE:
<223> OTHER INFORMATION: Motif

<400> SEQUENCE: 30

Ile Gly Gly Asp
1

<210> SEQ ID NO 31
<211> LENGTH: 4
<212> TYPE: PRT
<213> ORGANISM: Artificial sequence
<220> FEATURE:
<223> OTHER INFORMATION: Motif
<220> FEATURE:
<221> NAME/KEY: MISC_FEATURE
<222> LOCATION: (4)..(4)
<223> OTHER INFORMATION: X= any natural amino acid

<400> SEQUENCE: 31

Tyr Pro His Xaa
1

<210> SEQ ID NO 32
<211> LENGTH: 4
<212> TYPE: PRT
<213> ORGANISM: Artificial sequence
<220> FEATURE:
<223> OTHER INFORMATION: Motif

<400> SEQUENCE: 32

His Thr Gly Ala
1

<210> SEQ ID NO 33
<211> LENGTH: 4
<212> TYPE: PRT
<213> ORGANISM: Artificial sequence
<220> FEATURE:
<223> OTHER INFORMATION: Motif
<220> FEATURE:
<221> NAME/KEY: MISC_FEATURE
<222> LOCATION: (4)..(4)
<223> OTHER INFORMATION: X= any natural amino acid

<400> SEQUENCE: 33

Asp Arg Val Xaa
1

<210> SEQ ID NO 34
<211> LENGTH: 157
<212> TYPE: PRT
<213> ORGANISM: Bacillus amyloliquefaciens

<400> SEQUENCE: 34

Met Met Lys Met Glu Gly Ile Ala Leu Lys Lys Arg Leu Ser Trp Ile
1               5                   10                  15
```

```
Ser Val Cys Leu Leu Val Leu Val Ser Ala Ala Gly Met Leu Phe Ser
         20                  25                  30

Thr Ala Ala Lys Thr Glu Thr Ser Ser His Lys Ala His Thr Glu Ala
             35                  40                  45

Gln Val Ile Asn Thr Phe Asp Gly Val Ala Asp Tyr Leu Gln Thr Tyr
 50                  55                  60

His Lys Leu Pro Asp Asn Tyr Ile Thr Lys Ser Glu Ala Gln Ala Leu
 65                  70                  75                  80

Gly Trp Val Ala Ser Lys Gly Asn Leu Ala Asp Val Ala Pro Gly Lys
                 85                  90                  95

Ser Ile Gly Gly Asp Ile Phe Ser Asn Arg Glu Gly Lys Leu Pro Gly
            100                 105                 110

Lys Ser Gly Arg Thr Trp Arg Glu Ala Asp Ile Asn Tyr Thr Ser Gly
            115                 120                 125

Phe Arg Asn Ser Asp Arg Ile Leu Tyr Ser Ser Asp Trp Leu Ile Tyr
130                 135                 140

Lys Thr Thr Asp His Tyr Gln Thr Phe Thr Lys Ile Arg
145                 150                 155

<210> SEQ ID NO 35
<211> LENGTH: 890
<212> TYPE: DNA
<213> ORGANISM: Stenotrophomonas rhizophila
<220> FEATURE:
<221> NAME/KEY: CDS
<222> LOCATION: (1)..(477)
<220> FEATURE:
<221> NAME/KEY: sig_peptide
<222> LOCATION: (1)..(60)
<220> FEATURE:
<221> NAME/KEY: mat_peptide
<222> LOCATION: (61)..(477)
<220> FEATURE:
<221> NAME/KEY: misc_feature
<222> LOCATION: (477)..(887)
<223> OTHER INFORMATION: Inhibitor

<400> SEQUENCE: 35 atg cgc aaa cct cta ctt ctg ctc gtt gcc atc gtc ctg ctg gtg ggc      48
Met Arg Lys Pro Leu Leu Leu Leu Val Ala Ile Val Leu Leu Val Gly
-20                 -15                 -10                  -5 ggt ctt ttc gcc atc aag gaa gcc cag cgc gcg ccc gcg ccg cag ttc      96
Gly Leu Phe Ala Ile Lys Glu Ala Gln Arg Ala Pro Ala Pro Gln Phe
             -1   1               5                  10 gcg ccg tcg ctg acc cag ccg ggt gcc gac ccg gcg ccg atc gac aac     144
Ala Pro Ser Leu Thr Gln Pro Gly Ala Asp Pro Ala Pro Ile Asp Asn
         15                  20                  25 gcc ccg acc cat ccc ggt gcc acc gca aca cgc acc cat gac gcc ctg     192
Ala Pro Thr His Pro Gly Ala Thr Ala Thr Arg Thr His Asp Ala Leu
     30                  35                  40 ccc gcg ttc ctg cct gcc gaa gcg cgc cag acg ctc atc ctg atc cag     240
Pro Ala Phe Leu Pro Ala Glu Ala Arg Gln Thr Leu Ile Leu Ile Gln
 45                  50                  55                  60 cgt ggc ggc ccc tac ccg cac cgc cag gac ggc ggc gtt ttc agc aac     288
Arg Gly Gly Pro Tyr Pro His Arg Gln Asp Gly Gly Val Phe Ser Asn
                 65                  70                  75 cgc gaa cag cgc ctg ccg gat cga ccg cgt ggc tat tac cgc gag tac     336
Arg Glu Gln Arg Leu Pro Asp Arg Pro Arg Gly Tyr Tyr Arg Glu Tyr
             80                  85                  90 acc gtg gac acg ccg gga gcc ggc aac cgc ggc gca cgc cgc atc gtg     384
Thr Val Asp Thr Pro Gly Ala Gly Asn Arg Gly Ala Arg Arg Ile Val
         95                 100                 105
```

```
acc ggc ggc act ccg ccg acc ggt tgg ttc tac acc gac gac cat tac      432
Thr Gly Gly Thr Pro Pro Thr Gly Trp Phe Tyr Thr Asp Asp His Tyr
    110                 115                 120 gaa acc ttc cgc agt ttc gag gtc cca cct gcc ggg agc tgg caa          477
Glu Thr Phe Arg Ser Phe Glu Val Pro Pro Ala Gly Ser Trp Gln
125                 130                 135 tgaaccacga tggattcgaa ctgggtctgg acgacatcaa caatgccggc gtgtactcgg    537
tcaccaatga agacattgga ccgctgtcgg ccgcgatgcg cgatgccggg ctgcgcgtga    597
ccacgattga tctgcacgga tgcaatgaca agcgcacgct gatcgcgcgc gttgccgcgc    657
agctggattt cccgcagacg tttggtggca actgggacgc gttgctggac tgcttgagcg    717
acctgtcctg gatgcaggcc aacggctatg cgttgttctt cagtgatgcc gacgggttgc    777
aggaaaacgc ggagaaggac ttcgagacct tcctggatgt gctggccgac gccagcacct    837
cgtggagcaa ggacgacgtt ccgttctggg cgttcgtcgc gttgaacgag tag           890
```

```
<210> SEQ ID NO 36
<211> LENGTH: 159
<212> TYPE: PRT
<213> ORGANISM: Stenotrophomonas rhizophila

<400> SEQUENCE: 36

Met Arg Lys Pro Leu Leu Leu Val Ala Ile Val Leu Leu Val Gly
-20             -15                 -10             -5

Gly Leu Phe Ala Ile Lys Glu Ala Gln Arg Ala Pro Ala Pro Gln Phe
        -1  1             5                   10

Ala Pro Ser Leu Thr Gln Pro Gly Ala Asp Pro Ala Pro Ile Asp Asn
            15                  20                  25

Ala Pro Thr His Pro Gly Ala Thr Ala Thr Arg Thr His Asp Ala Leu
    30                  35                  40

Pro Ala Phe Leu Pro Ala Glu Ala Arg Gln Thr Leu Ile Leu Ile Gln
45                  50                  55                  60

Arg Gly Gly Pro Tyr Pro His Arg Gln Asp Gly Val Phe Ser Asn
                65                  70                  75

Arg Glu Gln Arg Leu Pro Asp Arg Pro Arg Gly Tyr Tyr Arg Glu Tyr
            80                  85                  90

Thr Val Asp Thr Pro Gly Ala Gly Asn Arg Gly Ala Arg Arg Ile Val
                95                  100                 105

Thr Gly Gly Thr Pro Pro Thr Gly Trp Phe Tyr Thr Asp Asp His Tyr
    110                 115                 120

Glu Thr Phe Arg Ser Phe Glu Val Pro Pro Ala Gly Ser Trp Gln
125                 130                 135
```

```
<210> SEQ ID NO 37
<211> LENGTH: 757
<212> TYPE: DNA
<213> ORGANISM: Erwinia persicina
<220> FEATURE:
<221> NAME/KEY: CDS
<222> LOCATION: (1)..(468)
<220> FEATURE:
<221> NAME/KEY: sig_peptide
<222> LOCATION: (1)..(60)
<220> FEATURE:
<221> NAME/KEY: mat_peptide
<222> LOCATION: (61)..(468)
<220> FEATURE:
<221> NAME/KEY: misc_feature
<222> LOCATION: (473)..(754)
<223> OTHER INFORMATION: Inhibitor
```

```
<400> SEQUENCE: 37 atg aac aaa aaa tta ata att gcc gcc ctc ctg gcg ctg gtc gcc agc        48
Met Asn Lys Lys Leu Ile Ile Ala Ala Leu Leu Ala Leu Val Ala Ser
-20             -15                 -10                 -5 tat gcc ggg ctg cgc gaa cat ggg cag tcg gag aag ccc gcc gtc cgg        96
Tyr Ala Gly Leu Arg Glu His Gly Gln Ser Glu Lys Pro Ala Val Arg
        -1  1               5                   10 cct tca gcg tcg gtt tct gcg cca cag cac gat agc aat gac atc gac        144
Pro Ser Ala Ser Val Ser Ala Pro Gln His Asp Ser Asn Asp Ile Asp
        15                  20                  25 gtg ctg acg caa cag cag cgt gtg gcc gac tat ctg cgt cag cat cag        192
Val Leu Thr Gln Gln Gln Arg Val Ala Asp Tyr Leu Arg Gln His Gln
    30                  35                  40 caa ctt cct ggt tac tac atc cgt aaa ggc gaa gcg cgt cag cag ggc        240
Gln Leu Pro Gly Tyr Tyr Ile Arg Lys Gly Glu Ala Arg Gln Gln Gly
45                  50                  55                  60 tgg gat ccg tcg aaa ggc aat ctg tgt cag gtg ctg ccg ggg cgg gcg        288
Trp Asp Pro Ser Lys Gly Asn Leu Cys Gln Val Leu Pro Gly Arg Ala
                65                  70                  75 atc ggc ggc gat cgc ttc agc aat cgg gaa ggg ggg ctg cca cag aaa        336
Ile Gly Gly Asp Arg Phe Ser Asn Arg Glu Gly Gly Leu Pro Gln Lys
                80                  85                  90 aac ggg cgt cgc tgg ttc gag gcg gac gtt aac tac gcc tgc ggg cga        384
Asn Gly Arg Arg Trp Phe Glu Ala Asp Val Asn Tyr Ala Cys Gly Arg
            95                  100                 105 cgc ggt acg gat cgc ctc ctc tac tcc agc gac ggt ctg att tac ctg        432
Arg Gly Thr Asp Arg Leu Leu Tyr Ser Ser Asp Gly Leu Ile Tyr Leu
        110                 115                 120 acc cgc gat cac tat cgt cac ttt caa cag gtg aac tgagatgcaa            478
Thr Arg Asp His Tyr Arg His Phe Gln Gln Val Asn
125                 130                 135 atggtgacgt tgatttaca acatatcggc agtgccggtg agttttaccg acagttcgcg        538
cgcaagtttg acctgtgtta tttcggtgac aatctggatg cgctgtggga tatgttaacg        598
gcaggcattc cattaccggt gcgtattaca ctgcgccacc tcgacgctca tccgcagcag        658
acagcgctgc tgcggatcct gcaggtgatg caggaggccg aagaggaaac cggtggtgcc        718
ttcagcgttc gcgtcagcac cccggcctgc ggggattaa                              757

<210> SEQ ID NO 38
<211> LENGTH: 156
<212> TYPE: PRT
<213> ORGANISM: Erwinia persicina

<400> SEQUENCE: 38

Met Asn Lys Lys Leu Ile Ile Ala Ala Leu Leu Ala Leu Val Ala Ser
-20             -15                 -10                 -5

Tyr Ala Gly Leu Arg Glu His Gly Gln Ser Glu Lys Pro Ala Val Arg
        -1  1               5                   10

Pro Ser Ala Ser Val Ser Ala Pro Gln His Asp Ser Asn Asp Ile Asp
        15                  20                  25

Val Leu Thr Gln Gln Gln Arg Val Ala Asp Tyr Leu Arg Gln His Gln
    30                  35                  40

Gln Leu Pro Gly Tyr Tyr Ile Arg Lys Gly Glu Ala Arg Gln Gln Gly
45                  50                  55                  60

Trp Asp Pro Ser Lys Gly Asn Leu Cys Gln Val Leu Pro Gly Arg Ala
                65                  70                  75
```

```
Ile Gly Gly Asp Arg Phe Ser Asn Arg Glu Gly Leu Pro Gln Lys
            80                  85                  90

Asn Gly Arg Arg Trp Phe Glu Ala Asp Val Asn Tyr Ala Cys Gly Arg
        95                  100                 105

Arg Gly Thr Asp Arg Leu Leu Tyr Ser Ser Asp Gly Leu Ile Tyr Leu
        110                 115                 120

Thr Arg Asp His Tyr Arg His Phe Gln Gln Val Asn
125                 130                 135

<210> SEQ ID NO 39
<211> LENGTH: 729
<212> TYPE: DNA
<213> ORGANISM: Paenibacillus tundrae
<220> FEATURE:
<221> NAME/KEY: CDS
<222> LOCATION: (1)..(435)
<220> FEATURE:
<221> NAME/KEY: sig_peptide
<222> LOCATION: (1)..(78)
<220> FEATURE:
<221> NAME/KEY: mat_peptide
<222> LOCATION: (79)..(435)
<220> FEATURE:
<221> NAME/KEY: misc_feature
<222> LOCATION: (454)..(726)
<223> OTHER INFORMATION: Inhibitor

<400> SEQUENCE: 39
```

| | | |
|---|---|---|
| atg gtt gta aaa aag tgg tta ggt ggt tta ctt ttt att ctg gcg acc | 48 | |
| Met Val Val Lys Lys Trp Leu Gly Gly Leu Leu Phe Ile Leu Ala Thr | | |
|   -25               -20                 -15 | | |

```
atc ctg ttt aca ggc tgc tca ctc gaa acg gtt tca tta aat ggc tca    96
Ile Leu Phe Thr Gly Cys Ser Leu Glu Thr Val Ser Leu Asn Gly Ser
-10              -5               -1   1                5 tct caa gag aaa gca act cta acg caa ttt gat gaa gta gcc aag tat   144
Ser Gln Glu Lys Ala Thr Leu Thr Gln Phe Asp Glu Val Ala Lys Tyr
             10                  15                  20 att tcg gag cat aat gaa ctc ccg gaa aat tat ata acc aag aaa gaa   192
Ile Ser Glu His Asn Glu Leu Pro Glu Asn Tyr Ile Thr Lys Lys Glu
         25                  30                  35 gct aga gaa tta gga tgg gag cct agt aaa ggt aat ttg gaa aaa gta   240
Ala Arg Glu Leu Gly Trp Glu Pro Ser Lys Gly Asn Leu Glu Lys Val
     40                  45                  50 gct ccg ggc aaa agc att ggc ggt gac gta ttt caa aat aga gaa ggg   288
Ala Pro Gly Lys Ser Ile Gly Gly Asp Val Phe Gln Asn Arg Glu Gly
55                  60                  65                  70 ctg ttg ccc aag aaa aaa gga agg act tgg tac gaa gca gat att aac   336
Leu Leu Pro Lys Lys Lys Gly Arg Thr Trp Tyr Glu Ala Asp Ile Asn
             75                  80                  85 tat tcg gga gga acg cgg ggc agt gat cgg att tta tac tcc aat gat   384
Tyr Ser Gly Gly Thr Arg Gly Ser Asp Arg Ile Leu Tyr Ser Asn Asp
         90                  95                  100 gga tta atc tat aaa aca acc gat cat tat cgt acg ttc gag caa atc   432
Gly Leu Ile Tyr Lys Thr Thr Asp His Tyr Arg Thr Phe Glu Gln Ile
         105                 110                 115 gaa tagagaaagg gtgatcatat gaagacagta gtcatcaatg gaaaggacat         485
Glu tcatggaaaa gaagagttac atgatgtcct tcagaccagt cttgagttag gtcaaacgta  545
tgggcggaat ttggacgcat tatgggattg cctaactgga tttcttccta tgccacttac  605
cattcagtgg attgattttg aggcaagtcg gaagtctctt ggagagtacg cagatcagtt  665
gttggatctg atgcatgaag ctgaagaaga gctggaagga tttacattgg acttaaaaaa  725
```

```
ttaa                                                                    729

<210> SEQ ID NO 40
<211> LENGTH: 145
<212> TYPE: PRT
<213> ORGANISM: Paenibacillus tundrae

<400> SEQUENCE: 40

Met Val Val Lys Lys Trp Leu Gly Gly Leu Leu Phe Ile Leu Ala Thr
    -25                 -20                 -15

Ile Leu Phe Thr Gly Cys Ser Leu Glu Thr Val Ser Leu Asn Gly Ser
-10              -5                  -1  1                   5

Ser Gln Glu Lys Ala Thr Leu Thr Gln Phe Asp Glu Val Ala Lys Tyr
                10                  15                  20

Ile Ser Glu His Asn Glu Leu Pro Glu Asn Tyr Ile Thr Lys Lys Glu
            25                  30                  35

Ala Arg Glu Leu Gly Trp Glu Pro Ser Lys Gly Asn Leu Glu Lys Val
 40                  45                  50

Ala Pro Gly Lys Ser Ile Gly Gly Asp Val Phe Gln Asn Arg Glu Gly
 55                  60                  65                  70

Leu Leu Pro Lys Lys Lys Gly Arg Thr Trp Tyr Glu Ala Asp Ile Asn
                 75                  80                  85

Tyr Ser Gly Gly Thr Arg Gly Ser Asp Arg Ile Leu Tyr Ser Asn Asp
             90                  95                 100

Gly Leu Ile Tyr Lys Thr Thr Asp His Tyr Arg Thr Phe Glu Gln Ile
            105                 110                 115

Glu

<210> SEQ ID NO 41
<211> LENGTH: 698
<212> TYPE: DNA
<213> ORGANISM: Saccharothrix sp.
<220> FEATURE:
<221> NAME/KEY: CDS
<222> LOCATION: (1)..(429)
<220> FEATURE:
<221> NAME/KEY: sig_peptide
<222> LOCATION: (1)..(78)
<220> FEATURE:
<221> NAME/KEY: mat_peptide
<222> LOCATION: (79)..(429)
<220> FEATURE:
<221> NAME/KEY: misc_feature
<222> LOCATION: (429)..(695)
<223> OTHER INFORMATION: Inhibitor

<400> SEQUENCE: 41 gtg act ccc gcc cgg cgg ctc tcc gtc gca ctg ctc ggc ctg atc gcg    48
Val Thr Pro Ala Arg Arg Leu Ser Val Ala Leu Leu Gly Leu Ile Ala
    -25                 -20                 -15 ctg gtc gtg gtc ggc tac ttc gtc aag gac ctc acc ggc acg tct tcg    96
Leu Val Val Val Gly Tyr Phe Val Lys Asp Leu Thr Gly Thr Ser Ser
-10              -5                  -1  1                   5 gac ccc gcc ccg ccg tcc gcc tcc gcc acg gtg ccc ggc gcg gac tcg   144
Asp Pro Ala Pro Pro Ser Ala Ser Ala Thr Val Pro Gly Ala Asp Ser
                10                  15                  20 ggg ctg ccg gtc gag ccg ctg tcg agc ctg ccc gcg cag gtc aag acc   192
Gly Leu Pro Val Glu Pro Leu Ser Ser Leu Pro Ala Gln Val Lys Thr
             25                  30                  35 acg tgg gag ctg atc ggc cgc ggc ggg ccg ttc cct cac ccg cgc aac   240
Thr Trp Glu Leu Ile Gly Arg Gly Gly Pro Phe Pro His Pro Arg Asn
```

```
gac ggc gtg acg ttc cag aac cgc gag aag ctg ctg ccc gcc aaa ccc     288
Asp Gly Val Thr Phe Gln Asn Arg Glu Lys Leu Leu Pro Ala Lys Pro
 55              60                  65                  70 tcc gac tac tac cgg gag tac acc gtg ccg aca ccg ggc agc gac gac     336
Ser Asp Tyr Tyr Arg Glu Tyr Thr Val Pro Thr Pro Gly Ser Asp Asp
                 75                  80                  85 cgc ggc gcg cgc cgg ctc gtg acc ggg tcg tcc gac gag gtg tac tac     384
Arg Gly Ala Arg Arg Leu Val Thr Gly Ser Ser Asp Glu Val Tyr Tyr
             90                  95                 100 acg gcc gac cac tac gag tcg ttc gtc gtc gtg gac gtg acc gga         429
Thr Ala Asp His Tyr Glu Ser Phe Val Val Val Asp Val Thr Gly
             105                 110                 115 tgacctaccg gcacgtggtg cgccggggcg cgcactcgaa gaaggacgcc atcggggcca   489
tcgcggacgc gttgagcttc cccgagtggt tcgggcacaa cctggacgcg ctgtacgact   549
gcctgaccga cctgtcgtgg ctgcccgagg gcgagcacgt gctggagtgg aaggcggcg    609
acgccgacgt gcaggccgtg ctggccgacg cggcagcacg caccaccgaa ctgggcgacc   669
gcgtgctgac cgtggtctac acggactag                                     698
```

<210> SEQ ID NO 42
<211> LENGTH: 143
<212> TYPE: PRT
<213> ORGANISM: Saccharothrix sp.

<400> SEQUENCE: 42

```
Val Thr Pro Ala Arg Arg Leu Ser Val Ala Leu Leu Gly Leu Ile Ala
    -25                 -20                 -15

Leu Val Val Val Gly Tyr Phe Val Lys Asp Leu Thr Gly Thr Ser Ser
-10                  -5                  -1   1               5

Asp Pro Ala Pro Pro Ser Ala Ser Ala Thr Val Pro Gly Ala Asp Ser
                10                  15                  20

Gly Leu Pro Val Glu Pro Leu Ser Ser Leu Pro Ala Gln Val Lys Thr
            25                  30                  35

Thr Trp Glu Leu Ile Gly Arg Gly Gly Pro Phe Pro His Pro Arg Asn
 40                  45                  50

Asp Gly Val Thr Phe Gln Asn Arg Glu Lys Leu Leu Pro Ala Lys Pro
 55                  60                  65                  70

Ser Asp Tyr Tyr Arg Glu Tyr Thr Val Pro Thr Pro Gly Ser Asp Asp
                 75                  80                  85

Arg Gly Ala Arg Arg Leu Val Thr Gly Ser Ser Asp Glu Val Tyr Tyr
             90                  95                 100

Thr Ala Asp His Tyr Glu Ser Phe Val Val Val Asp Val Thr Gly
             105                 110                 115
```

<210> SEQ ID NO 43
<211> LENGTH: 827
<212> TYPE: DNA
<213> ORGANISM: Saccharopolyspora endophytica
<220> FEATURE:
<221> NAME/KEY: CDS
<222> LOCATION: (1)..(411)
<220> FEATURE:
<221> NAME/KEY: sig_peptide
<222> LOCATION: (1)..(87)
<220> FEATURE:
<221> NAME/KEY: mat_peptide
<222> LOCATION: (88)..(411)
<220> FEATURE:
<221> NAME/KEY: misc_feature
<222> LOCATION: (420)..(824)
<223> OTHER INFORMATION: Inhibitor

<400> SEQUENCE: 43

| | | | | | | | | | | | | | | | | |
|---|---|---|---|---|---|---|---|---|---|---|---|---|---|---|---|---|
| gtg | agc | tcg | cgc | aag | cgc | att | tcg | tcg | gcg | ttg | gtc | ggg | ctt | gtc | gcc | 48 |
| Val | Ser | Ser | Arg | Lys | Arg | Ile | Ser | Ser | Ala | Leu | Val | Gly | Leu | Val | Ala | |
| | | | | -25 | | | | -20 | | | | | -15 | | | |
| ctg | gtc | gtg | ctg | ggg | tgg | ttc | ggc | aag | gac | gtc | gtc | gcc | gac | tcg | ccg | 96 |
| Leu | Val | Val | Leu | Gly | Trp | Phe | Gly | Lys | Asp | Val | Val | Ala | Asp | Ser | Pro | |
| | | | -10 | | | | -5 | | | | -1 | 1 | | | | |
| agc | acc | gag | gtg | ccg | ggt | gcc | agc | cag | tcc | gga | ctg | cag | gtc | cag | cag | 144 |
| Ser | Thr | Glu | Val | Pro | Gly | Ala | Ser | Gln | Ser | Gly | Leu | Gln | Val | Gln | Gln | |
| | 5 | | | | | 10 | | | | | 15 | | | | | |
| ctc | tcg | aag | ctg | ccg | ccc | gaa | acg | ggc | aag | acc | tac | cag | ctc | atc | gtc | 192 |
| Leu | Ser | Lys | Leu | Pro | Pro | Glu | Thr | Gly | Lys | Thr | Tyr | Gln | Leu | Ile | Val | |
| 20 | | | | | 25 | | | | | 30 | | | | | 35 | |
| aag | ggc | ggg | ccg | ttc | ccg | tac | ccg | ggc | aag | gac | ggc | tcg | gtg | ttc | ggc | 240 |
| Lys | Gly | Gly | Pro | Phe | Pro | Tyr | Pro | Gly | Lys | Asp | Gly | Ser | Val | Phe | Gly | |
| | | | | 40 | | | | | 45 | | | | | 50 | | |
| aac | cgc | gaa | ggc | gag | ctg | ccc | gag | cag | aag | tcc | ggt | tac | tac | cac | gag | 288 |
| Asn | Arg | Glu | Gly | Glu | Leu | Pro | Glu | Gln | Lys | Ser | Gly | Tyr | Tyr | His | Glu | |
| | | | 55 | | | | | 60 | | | | | 65 | | | |
| tac | acc | gtg | ccg | acc | ccg | ggc | tcg | aag | gat | cgc | ggc | gcg | cgc | cga | ctg | 336 |
| Tyr | Thr | Val | Pro | Thr | Pro | Gly | Ser | Lys | Asp | Arg | Gly | Ala | Arg | Arg | Leu | |
| | | 70 | | | | | 75 | | | | | 80 | | | | |
| gtc | acg | ggt | ggg | cag | gac | gag | gtg | tac | tac | acc | ggt | gat | cac | tac | gag | 384 |
| Val | Thr | Gly | Gly | Gln | Asp | Glu | Val | Tyr | Tyr | Thr | Gly | Asp | His | Tyr | Glu | |
| | 85 | | | | | 90 | | | | | 95 | | | | | |
| tcg | ttc | gtg | gtt | gtg | gat | acg | gcg | ggt | tgagtgccat gttcggagcg | | | | | | | 431 |
| Ser | Phe | Val | Val | Val | Asp | Thr | Ala | Gly | | | | | | | | |
| 100 | | | | 105 | | | | | | | | | | | | |

```
aaactggcca gcaggttgcg gaaggagcag ccggtgagtg atcagccggg cgccgacatc      491
acggctcgcg aagccgtcgt cacagccgag gaacgaggcg cgaccgccca cgtcctcgac      551
ggcgtcgacc tgaccagcaa gcgcaccact ctcgacggca tcgccgccgt cctcgacttc      611
cccgagtggg ccgggcggaa cctggactcc ctctacgact gcctgaccga cctgtcctgg      671
ctgccggaag gcgagcacgt cctgatctgg tccgggttcc aggacctcgc cgaccacgac      731
cccaaggcgt tcaacggcat caactcggtc ctgcgcgacg cggcggaacg ccccatgtgc      791
gggcgccgct tcaccgcggt gctgacccga tcctga                              827
```

<210> SEQ ID NO 44
<211> LENGTH: 137
<212> TYPE: PRT
<213> ORGANISM: Saccharopolyspora endophytica

<400> SEQUENCE: 44

Val Ser Ser Arg Lys Arg Ile Ser Ser Ala Leu Val Gly Leu Val Ala
                -25                 -20                 -15

Leu Val Val Leu Gly Trp Phe Gly Lys Asp Val Val Ala Asp Ser Pro
        -10                 -5                  -1  1

Ser Thr Glu Val Pro Gly Ala Ser Gln Ser Gly Leu Gln Val Gln Gln
    5                   10                  15

Leu Ser Lys Leu Pro Pro Glu Thr Gly Lys Thr Tyr Gln Leu Ile Val
20                  25                  30                  35

Lys Gly Gly Pro Phe Pro Tyr Pro Gly Lys Asp Gly Ser Val Phe Gly
                40                  45                  50

Asn Arg Glu Gly Glu Leu Pro Glu Gln Lys Ser Gly Tyr Tyr His Glu

```
                      55                  60                  65
Tyr Thr Val Pro Thr Pro Gly Ser Lys Asp Arg Gly Ala Arg Arg Leu
                 70                  75                  80

Val Thr Gly Gly Gln Asp Glu Val Tyr Tyr Thr Gly Asp His Tyr Glu
             85                  90                  95

Ser Phe Val Val Val Asp Thr Ala Gly
100                 105

<210> SEQ ID NO 45
<211> LENGTH: 803
<212> TYPE: DNA
<213> ORGANISM: Amycolatopsis circi
<220> FEATURE:
<221> NAME/KEY: CDS
<222> LOCATION: (1)..(450)
<220> FEATURE:
<221> NAME/KEY: sig_peptide
<222> LOCATION: (1)..(90)
<220> FEATURE:
<221> NAME/KEY: mat_peptide
<222> LOCATION: (91)..(450)
<220> FEATURE:
<221> NAME/KEY: misc_feature
<222> LOCATION: (450)..(800)
<223> OTHER INFORMATION: Inhibitor

<400> SEQUENCE: 45 atg gtc aac cgt agg cgg atc acc gct gcg ctc gtc ggt ctc ctc gtg     48
Met Val Asn Arg Arg Arg Ile Thr Ala Ala Leu Val Gly Leu Leu Val
-30                 -25                 -20                 -15 ctg gtg ctc ggc ggg tgg ctc gtc aag gaa acc gcc ggc tcc tcg gat     96
Leu Val Leu Gly Gly Trp Leu Val Lys Glu Thr Ala Gly Ser Ser Asp
                -10                 -5                  -1   1 tcg ccg gcg ccc tcg tcc tcg tcg ggt gct ccc gcc gcc gct tcc ggg    144
Ser Pro Ala Pro Ser Ser Ser Ser Gly Ala Pro Ala Ala Ala Ser Gly
            5                   10                  15 aag gtg ccg gga gcc gat tcc aag ctg ccg gtc aaa ccc ttg tcg tcg    192
Lys Val Pro Gly Ala Asp Ser Lys Leu Pro Val Lys Pro Leu Ser Ser
        20                  25                  30 ctg cct tcg cag gcg aag gac acg tgg agc ctg atc cac aag ggc ggg    240
Leu Pro Ser Gln Ala Lys Asp Thr Trp Ser Leu Ile His Lys Gly Gly
35                  40                  45                  50 ccc tac ccg tat ccg cgc aat gac gac gtc gtc ttc cag aac cgg gag    288
Pro Tyr Pro Tyr Pro Arg Asn Asp Asp Val Val Phe Gln Asn Arg Glu
                55                  60                  65 aaa aag ctg ccc gcg gag aag aac ggc tat tac cac gag tac acc gtg    336
Lys Lys Leu Pro Ala Glu Lys Asn Gly Tyr Tyr His Glu Tyr Thr Val
            70                  75                  80 aaa acg ccc ggg agc ccg gac cga ggg gcc cgc cgg ttg atc acg ggg    384
Lys Thr Pro Gly Ser Pro Asp Arg Gly Ala Arg Arg Leu Ile Thr Gly
        85                  90                  95 gcg ggg aaa gag ttg tat tac aca ggg gat cac tac gcg tcg ttc gtc    432
Ala Gly Lys Glu Leu Tyr Tyr Thr Gly Asp His Tyr Ala Ser Phe Val
100                 105                 110 gtt gtg gat ccg gca cgg tgagcggcga cgggacggcg cgggccgcgg           480
Val Val Asp Pro Ala Arg
115                 120 cggacacggc tttcgcgcgc ggggcttatc cgcatcgggt agacggagcg cggacgctgg    540
acaaactgtc cacgttggac gcgatcggcg aggcgctgtc ttttccggcc tatttcgggc    600
ggaatctgga cgcgctgtac gacatgctca cggatctgtc gtggttgccg accgcgagc     660 acgtgctgat ctggtccggt tcggacggat tgaaggccgc cgagcccaag gcttatctgg    720
```

-continued

```
cggtgcgcag cgtgttgtcg gacgcgcagc gggccatggg ctccggcgac cggcggctga    780
ccttggtgct ggtggattcc tga                                            803
```

<210> SEQ ID NO 46
<211> LENGTH: 150
<212> TYPE: PRT
<213> ORGANISM: Amycolatopsis circi

<400> SEQUENCE: 46

```
Met Val Asn Arg Arg Arg Ile Thr Ala Ala Leu Val Gly Leu Leu Val
-30                 -25                 -20                 -15

Leu Val Leu Gly Gly Trp Leu Val Lys Glu Thr Ala Gly Ser Ser Asp
            -10                  -5                  -1  1

Ser Pro Ala Pro Ser Ser Ser Gly Ala Pro Ala Ala Ala Ser Gly
         5                  10                  15

Lys Val Pro Gly Ala Asp Ser Lys Leu Pro Val Lys Pro Leu Ser Ser
 20                  25                  30

Leu Pro Ser Gln Ala Lys Asp Thr Trp Ser Leu Ile His Lys Gly Gly
 35                  40                  45                  50

Pro Tyr Pro Tyr Pro Arg Asn Asp Asp Val Val Phe Gln Asn Arg Glu
                 55                  60                  65

Lys Lys Leu Pro Ala Glu Lys Asn Gly Tyr Tyr His Glu Tyr Thr Val
             70                  75                  80

Lys Thr Pro Gly Ser Pro Asp Arg Gly Ala Arg Arg Leu Ile Thr Gly
                 85                  90                  95

Ala Gly Lys Glu Leu Tyr Tyr Thr Gly Asp His Tyr Ala Ser Phe Val
100                 105                 110

Val Val Asp Pro Ala Arg
115                 120
```

<210> SEQ ID NO 47
<211> LENGTH: 730
<212> TYPE: DNA
<213> ORGANISM: Paenibacillus sp.
<220> FEATURE:
<221> NAME/KEY: CDS
<222> LOCATION: (1)..(435)
<220> FEATURE:
<221> NAME/KEY: sig_peptide
<222> LOCATION: (1)..(78)
<220> FEATURE:
<221> NAME/KEY: mat_peptide
<222> LOCATION: (79)..(435)
<220> FEATURE:
<221> NAME/KEY: misc_feature
<222> LOCATION: (455)..(727)
<223> OTHER INFORMATION: Inhibitor

<400> SEQUENCE: 47

```
gtg tat att aaa aaa tgg cta ggt gct gta ctc att att ctt gcg acg    48
Val Tyr Ile Lys Lys Trp Leu Gly Ala Val Leu Ile Ile Leu Ala Thr
    -25                 -20                 -15 atg ctg ttc gca ggt tgt tca ctt gaa tcg cta tct gta ggt gat acg    96
Met Leu Phe Ala Gly Cys Ser Leu Glu Ser Leu Ser Val Gly Asp Thr
-10                  -5                  -1  1                  5 aac cag act cat gct gtc ttg aac caa ttt gac gaa gtt gcc aat tat   144
Asn Gln Thr His Ala Val Leu Asn Gln Phe Asp Glu Val Ala Asn Tyr
             10                  15                  20 ctt gcc gag cat cag gaa ctt ccg gac aat tat att acc aag aag gag   192
Leu Ala Glu His Gln Glu Leu Pro Asp Asn Tyr Ile Thr Lys Lys Glu
 25                  30                  35
```

```
gcc aga gct tta ggc tgg gaa cca agt gaa gga aat ttg caa gat atg    240
Ala Arg Ala Leu Gly Trp Glu Pro Ser Glu Gly Asn Leu Gln Asp Met
     40                  45                  50 gcc cca ggc aaa agt atc ggc ggt gat att ttt cag aat cgg gaa ggc    288
Ala Pro Gly Lys Ser Ile Gly Gly Asp Ile Phe Gln Asn Arg Glu Gly
 55                  60                  65                  70 ctg tta ccc aag aaa aag gga aga acg tgg tac gag gca gat atc aat    336
Leu Leu Pro Lys Lys Lys Gly Arg Thr Trp Tyr Glu Ala Asp Ile Asn
                 75                  80                  85 tat tcc ggt gga acc cgg ggg agt gac cga atc ctc tat tcc agt gat    384
Tyr Ser Gly Gly Thr Arg Gly Ser Asp Arg Ile Leu Tyr Ser Ser Asp
         90                  95                 100 ggc tta ata tac aag aca acc gat cat tat cgc acg ttt gaa caa atc    432
Gly Leu Ile Tyr Lys Thr Thr Asp His Tyr Arg Thr Phe Glu Gln Ile
            105                 110                 115 aaa tgaccaaagg taggatggta tgaagacagt aatcattgat ggaaatgata         485
Lys ttcatggaaa agaagagctg catgatattc ttcaggcgaa gctggggtta gatgactctt    545
acgggcggaa tctcgatgcg ttatgggatg tcattacagg cttcatttca attccactaa    605
ccattcaatg ggtgaatttt gaggccagta ggtctgtgct tggagaatac gctgatcaac    665
tattggagtt attgcgtgac gcagaagaag agctggatcg atttcaattg gatctgaaaa    725
tgtaa                                                                730

<210> SEQ ID NO 48
<211> LENGTH: 145
<212> TYPE: PRT
<213> ORGANISM: Paenibacillus sp.

<400> SEQUENCE: 48

Val Tyr Ile Lys Lys Trp Leu Gly Ala Val Leu Ile Ile Leu Ala Thr
        -25                 -20                 -15

Met Leu Phe Ala Gly Cys Ser Leu Glu Ser Leu Ser Val Gly Asp Thr
-10                  -5                  -1   1               5

Asn Gln Thr His Ala Val Leu Asn Gln Phe Asp Glu Val Ala Asn Tyr
             10                  15                  20

Leu Ala Glu His Gln Glu Leu Pro Asp Asn Tyr Ile Thr Lys Lys Glu
         25                  30                  35

Ala Arg Ala Leu Gly Trp Glu Pro Ser Glu Gly Asn Leu Gln Asp Met
     40                  45                  50

Ala Pro Gly Lys Ser Ile Gly Gly Asp Ile Phe Gln Asn Arg Glu Gly
 55                  60                  65                  70

Leu Leu Pro Lys Lys Lys Gly Arg Thr Trp Tyr Glu Ala Asp Ile Asn
                 75                  80                  85

Tyr Ser Gly Gly Thr Arg Gly Ser Asp Arg Ile Leu Tyr Ser Ser Asp
         90                  95                 100

Gly Leu Ile Tyr Lys Thr Thr Asp His Tyr Arg Thr Phe Glu Gln Ile
            105                 110                 115

Lys

<210> SEQ ID NO 49
<211> LENGTH: 719
<212> TYPE: DNA
<213> ORGANISM: Paenibacillus sp.
<220> FEATURE:
<221> NAME/KEY: CDS
<222> LOCATION: (1)..(432)
```

```
<220> FEATURE:
<221> NAME/KEY: sig_peptide
<222> LOCATION: (1)..(81)
<220> FEATURE:
<221> NAME/KEY: mat_peptide
<222> LOCATION: (82)..(432)
<220> FEATURE:
<221> NAME/KEY: misc_feature
<222> LOCATION: (447)..(716)
<223> OTHER INFORMATION: Inhibitor

<400> SEQUENCE: 49 atg ttt ttt aga aaa ata ggt tat acg ttg tta att atc ttg gct gca        48
Met Phe Phe Arg Lys Ile Gly Tyr Thr Leu Leu Ile Ile Leu Ala Ala
        -25                 -20                 -15 ctg gtg ttc tca ggt tgt acc ccg cag tcg att ctg gat cag act acg        96
Leu Val Phe Ser Gly Cys Thr Pro Gln Ser Ile Leu Asp Gln Thr Thr
    -10                  -5              -1   1                5 act acg gct tca cag gat atg gga ttt gat gag gtc gcc aag tat ata       144
Thr Thr Ala Ser Gln Asp Met Gly Phe Asp Glu Val Ala Lys Tyr Ile
                 10                  15                  20 tcg gag cac aat gcg ctt ccg ccg aac tac att acg aag aaa gag gct       192
Ser Glu His Asn Ala Leu Pro Pro Asn Tyr Ile Thr Lys Lys Glu Ala
             25                  30                  35 aga gca ttg ggc tgg gaa cca agt gaa ggc aat ttg caa gaa gtt gct       240
Arg Ala Leu Gly Trp Glu Pro Ser Glu Gly Asn Leu Gln Glu Val Ala
         40                  45                  50 cca ggc aaa agc atc ggt ggg gat gtg ttt aga aat cga gaa ggc ttg       288
Pro Gly Lys Ser Ile Gly Gly Asp Val Phe Arg Asn Arg Glu Gly Leu
 55                  60                  65 tta ccg aat aag aaa ggc cga acg tgg tat gaa gct gac atc cat tat       336
Leu Pro Asn Lys Lys Gly Arg Thr Trp Tyr Glu Ala Asp Ile His Tyr
 70                  75                  80                  85 gca ggt gga aga cgt gga agt gat cga atc tta tat tca aac gac gga       384
Ala Gly Gly Arg Arg Gly Ser Asp Arg Ile Leu Tyr Ser Asn Asp Gly
                 90                  95                 100 cta atc tat aag aca aca gac cat tat gaa tca ttt gag cag tta aaa       432
Leu Ile Tyr Lys Thr Thr Asp His Tyr Glu Ser Phe Glu Gln Leu Lys
                105                 110                 115 taacggaggg tattatgaat atcattcaga ttgatggaga gcaattactt gcgagagatg    492
aactgcatgc catacttcag gagaagcttg aattgggaga acactacgga cgtaacttag    552
acgcgctgtg ggactgctta acaggggaag tgagcatgcc gatcaccatt cagtgggttc    612
atttcgagaa aagtaaacaa gtactaggag gatacgctga ccaagtcatt gatttgatgc    672
gcgaggtaga agaggagatc gaaggattca cattggaatt gaagtag                  719

<210> SEQ ID NO 50
<211> LENGTH: 144
<212> TYPE: PRT
<213> ORGANISM: Paenibacillus sp.

<400> SEQUENCE: 50

Met Phe Phe Arg Lys Ile Gly Tyr Thr Leu Leu Ile Ile Leu Ala Ala
        -25                 -20                 -15

Leu Val Phe Ser Gly Cys Thr Pro Gln Ser Ile Leu Asp Gln Thr Thr
    -10                  -5              -1   1                5

Thr Thr Ala Ser Gln Asp Met Gly Phe Asp Glu Val Ala Lys Tyr Ile
                 10                  15                  20

Ser Glu His Asn Ala Leu Pro Pro Asn Tyr Ile Thr Lys Lys Glu Ala
             25                  30                  35
```

```
Arg Ala Leu Gly Trp Glu Pro Ser Glu Gly Asn Leu Gln Glu Val Ala
            40                  45                  50

Pro Gly Lys Ser Ile Gly Gly Asp Val Phe Arg Asn Arg Glu Gly Leu
 55                  60                  65

Leu Pro Asn Lys Lys Gly Arg Thr Trp Tyr Glu Ala Asp Ile His Tyr
 70                  75                  80                  85

Ala Gly Gly Arg Arg Gly Ser Asp Arg Ile Leu Tyr Ser Asn Asp Gly
                90                  95                 100

Leu Ile Tyr Lys Thr Thr Asp His Tyr Glu Ser Phe Glu Gln Leu Lys
               105                 110                 115

<210> SEQ ID NO 51
<211> LENGTH: 839
<212> TYPE: DNA
<213> ORGANISM: Paenibacillus sp.
<220> FEATURE:
<221> NAME/KEY: CDS
<222> LOCATION: (1)..(570)
<220> FEATURE:
<221> NAME/KEY: sig_peptide
<222> LOCATION: (1)..(102)
<220> FEATURE:
<221> NAME/KEY: mat_peptide
<222> LOCATION: (103)..(570)
<220> FEATURE:
<221> NAME/KEY: misc_feature
<222> LOCATION: (570)..(836)
<223> OTHER INFORMATION: Inhibitor

<400> SEQUENCE: 51 atg ttt tat gta atg atg aaa aaa atg ggc cga tgg tca cgt tcc ggg     48
Met Phe Tyr Val Met Met Lys Lys Met Gly Arg Trp Ser Arg Ser Gly
                -30                 -25                 -20 ttg gca gcg ata att gtt atg ttg atg att gta ctg act ggc tgt gcg     96
Leu Ala Ala Ile Ile Val Met Leu Met Ile Val Leu Thr Gly Cys Ala
        -15                 -10                  -5 aat gcc act gag aac caa tcc cca gcc ttc cag gag cca aac tct tct    144
Asn Ala Thr Glu Asn Gln Ser Pro Ala Phe Gln Glu Pro Asn Ser Ser
 -1   1               5                  10 gtg tca aac tcc agt cca acg gaa cag ccg cag cca tcc cct atc ccg    192
Val Ser Asn Ser Ser Pro Thr Glu Gln Pro Gln Pro Ser Pro Ile Pro
 15                  20                  25                  30 acg aac tcc gaa gtg ggg gag aat gtc caa gcc ccg ctt acc agc ttc    240
Thr Asn Ser Glu Val Gly Glu Asn Val Gln Ala Pro Leu Thr Ser Phe
                 35                  40                  45 aag gct gta tcg gat tac att cgg gaa cac cat aca ctt ccg gca aat    288
Lys Ala Val Ser Asp Tyr Ile Arg Glu His His Thr Leu Pro Ala Asn
         50                  55                  60 ttc att acc aaa aaa gaa gcc gag cag ctc ggc tgg gtc cca gcc aaa    336
Phe Ile Thr Lys Lys Glu Ala Glu Gln Leu Gly Trp Val Pro Ala Lys
 65                  70                  75 gga aac ctg gac caa gta gcg cct ggt aaa agc ata ggt ggt gac cgc    384
Gly Asn Leu Asp Gln Val Ala Pro Gly Lys Ser Ile Gly Gly Asp Arg
     80                  85                  90 ttc gga aat cgg gaa gga ctg ctg cct aag gca aaa aac cgg att tgg    432
Phe Gly Asn Arg Glu Gly Leu Leu Pro Lys Ala Lys Asn Arg Ile Trp
 95                 100                 105                 110 tat gaa gcg gat att aac tat act aag aag tcg cgc ggc gcg gat cgg    480
Tyr Glu Ala Asp Ile Asn Tyr Thr Lys Lys Ser Arg Gly Ala Asp Arg
                115                 120                 125 gtg ctc tac tcc aat gat gga tta att tac atg act acc gat cat tat    528
Val Leu Tyr Ser Asn Asp Gly Leu Ile Tyr Met Thr Thr Asp His Tyr
        130                 135                 140
```

```
aag tcg ttt acg gat att acg aag gaa ggc agt gtc ccc gaa         570
Lys Ser Phe Thr Asp Ile Thr Lys Glu Gly Ser Val Pro Glu
        145                 150                 155 tgagtaacgt tgtggaactg agacagtccg agggagatcg ttatgagaac gtacatgatt   630
ggttacagca ggagcttaag ctgcctgaat ggtacggtca aaatttagat gcattatggg   690
attgtgttac cgggcatctg cctttaccac tgaagatcac atggattgcg gattccgaga   750
acgaagaacg ttattccgcc gtgacagagg tttttcagga tgcagccgat caatatgatg   810
agataagctt cgaatatgtc actggttag                                    839

<210> SEQ ID NO 52
<211> LENGTH: 190
<212> TYPE: PRT
<213> ORGANISM: Paenibacillus sp.

<400> SEQUENCE: 52

Met Phe Tyr Val Met Met Lys Lys Met Gly Arg Trp Ser Arg Ser Gly
                -30                 -25                 -20

Leu Ala Ala Ile Ile Val Met Leu Met Ile Val Leu Thr Gly Cys Ala
            -15                 -10                  -5

Asn Ala Thr Glu Asn Gln Ser Pro Ala Phe Gln Glu Pro Asn Ser Ser
 -1   1                   5                  10

Val Ser Asn Ser Ser Pro Thr Glu Gln Pro Gln Pro Ser Pro Ile Pro
 15                  20                  25                  30

Thr Asn Ser Glu Val Gly Glu Asn Val Gln Ala Pro Leu Thr Ser Phe
                 35                  40                  45

Lys Ala Val Ser Asp Tyr Ile Arg Glu His His Thr Leu Pro Ala Asn
             50                  55                  60

Phe Ile Thr Lys Lys Glu Ala Glu Gln Leu Gly Trp Val Pro Ala Lys
             65                  70                  75

Gly Asn Leu Asp Gln Val Ala Pro Gly Lys Ser Ile Gly Gly Asp Arg
 80                  85                  90

Phe Gly Asn Arg Glu Gly Leu Leu Pro Lys Ala Lys Asn Arg Ile Trp
 95                 100                 105                 110

Tyr Glu Ala Asp Ile Asn Tyr Thr Lys Lys Ser Arg Gly Ala Asp Arg
                115                 120                 125

Val Leu Tyr Ser Asn Asp Gly Leu Ile Tyr Met Thr Thr Asp His Tyr
            130                 135                 140

Lys Ser Phe Thr Asp Ile Thr Lys Glu Gly Ser Val Pro Glu
        145                 150                 155

<210> SEQ ID NO 53
<211> LENGTH: 766
<212> TYPE: DNA
<213> ORGANISM: Alkalimonas sp.
<220> FEATURE:
<221> NAME/KEY: CDS
<222> LOCATION: (1)..(414)
<220> FEATURE:
<221> NAME/KEY: sig_peptide
<222> LOCATION: (1)..(69)
<220> FEATURE:
<221> NAME/KEY: mat_peptide
<222> LOCATION: (70)..(414)
<220> FEATURE:
<221> NAME/KEY: misc_feature
<222> LOCATION: (401)..(763)
<223> OTHER INFORMATION: Inhibitor

<400> SEQUENCE: 53
```

```
atg aag aaa ctt ctt gtt gta cta ctg gtt ctg gcc ggt ttt tat cac        48
Met Lys Lys Leu Leu Val Val Leu Leu Val Leu Ala Gly Phe Tyr His
        -20                 -15                 -10 ttt tac cag agc gat cgt ggc cag cca tcg gta act cca gga gct gaa        96
Phe Tyr Gln Ser Asp Arg Gly Gln Pro Ser Val Thr Pro Gly Ala Glu
         -5              -1   1                  5 gta acc cag tct ggc agt ggt gca caa ccg cgc atg tct gcc cag cag       144
Val Thr Gln Ser Gly Ser Gly Ala Gln Pro Arg Met Ser Ala Gln Gln
10                   15                  20                  25 ttg gaa ctg caa aag acg ctg cag cgg atc caa ggc aac ggc cct ttt       192
Leu Glu Leu Gln Lys Thr Leu Gln Arg Ile Gln Gly Asn Gly Pro Phe
                30                  35                  40 cct tat gac cgt gat ggc att acc ttc cac aat cgg gag cgt ttg ttg       240
Pro Tyr Asp Arg Asp Gly Ile Thr Phe His Asn Arg Glu Arg Leu Leu
            45                  50                  55 ccg att aaa ccc aga ggt tac tac cgc gaa tat acg gtg gat aca cca       288
Pro Ile Lys Pro Arg Gly Tyr Tyr Arg Glu Tyr Thr Val Asp Thr Pro
        60                  65                  70 ggt ctt tca cat cgt gga cca aga cga gta gtc act gga ggg aat ccg       336
Gly Leu Ser His Arg Gly Pro Arg Arg Val Val Thr Gly Gly Asn Pro
75                  80                  85 ccg gta gtc ttt tat tac act gaa gat cac tat cag tcc ttt cgt cgc       384
Pro Val Val Phe Tyr Tyr Thr Glu Asp His Tyr Gln Ser Phe Arg Arg
90                  95                  100                 105 atc agt ggt gat cca tat gaa cgc att cat tgacaatcca actgtgcagc         434
Ile Ser Gly Asp Pro Tyr Glu Arg Ile His
                110                 115 ttcggcatga agctgctcca gccgatgctg tctgcctggc ttgcaatggt cgtgttgacc     494
gagagacgat gttagccagc ctaaccactc attttcagtt tcctgattat ttcggcaata     554
attgggatgc agcttacgat ctgttgctgg atagagtgga tgcactggcg gtggacacag     614
gttggcgttt tagttcaggc tcagctttgc acacagatcc cgaggccatc accagttttt     674
tgcagctgat gcaggatctg gttgattatg catccgaccg agggatccga ttacaagttg     734
agctctttct ggactctggt gaggtagatt ga                                   766

<210> SEQ ID NO 54
<211> LENGTH: 138
<212> TYPE: PRT
<213> ORGANISM: Alkalimonas sp.

<400> SEQUENCE: 54

Met Lys Lys Leu Leu Val Val Leu Leu Val Leu Ala Gly Phe Tyr His
        -20                 -15                 -10

Phe Tyr Gln Ser Asp Arg Gly Gln Pro Ser Val Thr Pro Gly Ala Glu
         -5              -1   1                  5

Val Thr Gln Ser Gly Ser Gly Ala Gln Pro Arg Met Ser Ala Gln Gln
10                  15                  20                  25

Leu Glu Leu Gln Lys Thr Leu Gln Arg Ile Gln Gly Asn Gly Pro Phe
                30                  35                  40

Pro Tyr Asp Arg Asp Gly Ile Thr Phe His Asn Arg Glu Arg Leu Leu
            45                  50                  55

Pro Ile Lys Pro Arg Gly Tyr Tyr Arg Glu Tyr Thr Val Asp Thr Pro
        60                  65                  70

Gly Leu Ser His Arg Gly Pro Arg Arg Val Val Thr Gly Gly Asn Pro
75                  80                  85

Pro Val Val Phe Tyr Tyr Thr Glu Asp His Tyr Gln Ser Phe Arg Arg
```

```
                90                   95                  100                 105
Ile Ser Gly Asp Pro Tyr Glu Arg Ile His
            110                 115

<210> SEQ ID NO 55
<211> LENGTH: 707
<212> TYPE: DNA
<213> ORGANISM: Nonomuraea dietziae
<220> FEATURE:
<221> NAME/KEY: CDS
<222> LOCATION: (1)..(405)
<220> FEATURE:
<221> NAME/KEY: sig_peptide
<222> LOCATION: (1)..(81)
<220> FEATURE:
<221> NAME/KEY: mat_peptide
<222> LOCATION: (82)..(405)
<220> FEATURE:
<221> NAME/KEY: misc_feature
<222> LOCATION: (405)..(704)
<223> OTHER INFORMATION: Inhibitor

<400> SEQUENCE: 55 gtg aat ctc acg ggc atc gcg gcg ctc ccg ctc gcc atc gga acg ttc       48
Val Asn Leu Thr Gly Ile Ala Ala Leu Pro Leu Ala Ile Gly Thr Phe
        -25                 -20                 -15 atc ggg ggc tgc ggc gcc gcc agc gct cct gcg gca ctg ccc gag gag       96
Ile Gly Gly Cys Gly Ala Ala Ser Ala Pro Ala Ala Leu Pro Glu Glu
    -10                  -5                  -1   1                5 tcg cgc gcc gcg ccc cca cct gcg gca ctg ccc gaa aag gcg ctg tcc      144
Ser Arg Ala Ala Pro Pro Pro Ala Ala Leu Pro Glu Lys Ala Leu Ser
                 10                  15                  20 gcg ctt ccc cct gag gcg gcc aag acc tgg cgg ctc atc cag agc gac      192
Ala Leu Pro Pro Glu Ala Ala Lys Thr Trp Arg Leu Ile Gln Ser Asp
             25                  30                  35 ggc ccc ttc ccc tac cgg cgc gac ggc gtg gtc ttc cag aac cgc gag      240
Gly Pro Phe Pro Tyr Arg Arg Asp Gly Val Val Phe Gln Asn Arg Glu
         40                  45                  50 cgc atc ctg ccg cag cag aag cgc ggc tac tac cac gag tac acg gtg      288
Arg Ile Leu Pro Gln Gln Lys Arg Gly Tyr Tyr His Glu Tyr Thr Val
     55                  60                  65 ccg acc ccc ggc tca cgc gac aga ggg gcg cgc agg ctc gtc acc ggc      336
Pro Thr Pro Gly Ser Arg Asp Arg Gly Ala Arg Arg Leu Val Thr Gly
 70                  75                  80                  85 acc ggg gtc gac gag ctc tac tac acg ggc gac cac tac cgg tcc ttc      384
Thr Gly Val Asp Glu Leu Tyr Tyr Thr Gly Asp His Tyr Arg Ser Phe
                 90                  95                 100 gtc gcg gtg gac gtg aag cga tgagattcga gcaccggatc aacggctcgc         435
Val Ala Val Asp Val Lys Arg
             105 gactcgacac ctccgacagc gtgatgaccg ccatcgcctc cgcgctgaag ttcccctcct    495 acttcgggta caacctcgac gccctctacg acagcctcac cgacctgtcg tggctccctc    555 ctggcgagca cgtgctcgtc tggtcgagcc cgggggcgtt gcgcgcggcc gacgccaccg    615 cctacgacgc catcgccgcc gtgctggccg acgcggtcgc cgacggcacc ggcggcgacg    675 cctatctgtc cgtcgtcctg cgggccggct ga                                  707

<210> SEQ ID NO 56
<211> LENGTH: 135
<212> TYPE: PRT
<213> ORGANISM: Nonomuraea dietziae

<400> SEQUENCE: 56
```

```
Val Asn Leu Thr Gly Ile Ala Ala Leu Pro Leu Ala Ile Gly Thr Phe
        -25              -20             -15
Ile Gly Gly Cys Gly Ala Ala Ser Ala Pro Ala Ala Leu Pro Glu Glu
-10              -5               -1   1               5
Ser Arg Ala Ala Pro Pro Ala Ala Leu Pro Glu Lys Ala Leu Ser
                10              15              20
Ala Leu Pro Pro Glu Ala Ala Lys Thr Trp Arg Leu Ile Gln Ser Asp
        25              30                      35
Gly Pro Phe Pro Tyr Arg Arg Asp Gly Val Val Phe Gln Asn Arg Glu
        40              45              50
Arg Ile Leu Pro Gln Gln Lys Arg Gly Tyr Tyr His Glu Tyr Thr Val
        55              60              65
Pro Thr Pro Gly Ser Arg Asp Arg Gly Ala Arg Arg Leu Val Thr Gly
70              75              80                      85
Thr Gly Val Asp Glu Leu Tyr Tyr Thr Gly Asp His Tyr Arg Ser Phe
                90              95              100
Val Ala Val Asp Val Lys Arg
                105
```

<210> SEQ ID NO 57
<211> LENGTH: 139
<212> TYPE: PRT
<213> ORGANISM: Stenotrophomonas rhizophila

<400> SEQUENCE: 57

```
Ile Lys Glu Ala Gln Arg Ala Pro Ala Pro Gln Phe Ala Pro Ser Leu
1               5                   10                  15
Thr Gln Pro Gly Ala Asp Pro Ala Pro Ile Asp Asn Ala Pro Thr His
                20                  25                  30
Pro Gly Ala Thr Ala Thr Arg Thr His Asp Ala Leu Pro Ala Phe Leu
            35                  40                  45
Pro Ala Glu Ala Arg Gln Thr Leu Ile Leu Ile Gln Arg Gly Gly Pro
        50                  55                  60
Tyr Pro His Arg Gln Asp Gly Gly Val Phe Ser Asn Arg Glu Gln Arg
65                  70                  75                  80
Leu Pro Asp Arg Pro Arg Gly Tyr Tyr Arg Glu Tyr Thr Val Asp Thr
                85                  90                  95
Pro Gly Ala Gly Asn Arg Gly Ala Arg Arg Ile Val Thr Gly Gly Thr
                100                 105                 110
Pro Pro Thr Gly Trp Phe Tyr Thr Asp His Tyr Glu Thr Phe Arg
            115                 120                 125
Ser Phe Glu Val Pro Pro Ala Gly Ser Trp Gln
    130                 135
```

<210> SEQ ID NO 58
<211> LENGTH: 136
<212> TYPE: PRT
<213> ORGANISM: Erwinia persicina

<400> SEQUENCE: 58

```
Arg Glu His Gly Gln Ser Glu Lys Pro Ala Val Arg Pro Ser Ala Ser
1               5                   10                  15
Val Ser Ala Pro Gln His Asp Ser Asn Asp Ile Asp Val Leu Thr Gln
                20                  25                  30
Gln Gln Arg Val Ala Asp Tyr Leu Arg Gln His Gln Leu Pro Gly
            35                  40                  45
```

Tyr Tyr Ile Arg Lys Gly Glu Ala Arg Gln Gln Gly Trp Asp Pro Ser
            50                  55                  60

Lys Gly Asn Leu Cys Gln Val Leu Pro Gly Arg Ala Ile Gly Gly Asp
 65                  70                  75                  80

Arg Phe Ser Asn Arg Glu Gly Gly Leu Pro Gln Lys Asn Gly Arg Arg
                 85                  90                  95

Trp Phe Glu Ala Asp Val Asn Tyr Ala Cys Gly Arg Arg Gly Thr Asp
            100                 105                 110

Arg Leu Leu Tyr Ser Ser Asp Gly Leu Ile Tyr Leu Thr Arg Asp His
        115                 120                 125

Tyr Arg His Phe Gln Gln Val Asn
        130                 135

<210> SEQ ID NO 59
<211> LENGTH: 119
<212> TYPE: PRT
<213> ORGANISM: Paenibacillus tundrae

<400> SEQUENCE: 59

Val Ser Leu Asn Gly Ser Ser Gln Glu Lys Ala Thr Leu Thr Gln Phe
 1               5                  10                  15

Asp Glu Val Ala Lys Tyr Ile Ser Glu His Asn Glu Leu Pro Glu Asn
             20                  25                  30

Tyr Ile Thr Lys Lys Glu Ala Arg Glu Leu Gly Trp Glu Pro Ser Lys
         35                  40                  45

Gly Asn Leu Glu Lys Val Ala Pro Gly Lys Ser Ile Gly Gly Asp Val
 50                  55                  60

Phe Gln Asn Arg Glu Gly Leu Leu Pro Lys Lys Lys Gly Arg Thr Trp
 65                  70                  75                  80

Tyr Glu Ala Asp Ile Asn Tyr Ser Gly Thr Arg Gly Ser Asp Arg
                 85                  90                  95

Ile Leu Tyr Ser Asn Asp Gly Leu Ile Tyr Lys Thr Thr Asp His Tyr
            100                 105                 110

Arg Thr Phe Glu Gln Ile Glu
        115

<210> SEQ ID NO 60
<211> LENGTH: 117
<212> TYPE: PRT
<213> ORGANISM: Saccharothrix sp.

<400> SEQUENCE: 60

Leu Thr Gly Thr Ser Ser Asp Pro Ala Pro Pro Ser Ala Ser Ala Thr
 1               5                  10                  15

Val Pro Gly Ala Asp Ser Gly Leu Pro Val Glu Pro Leu Ser Ser Leu
             20                  25                  30

Pro Ala Gln Val Lys Thr Thr Trp Glu Leu Ile Gly Arg Gly Gly Pro
         35                  40                  45

Phe Pro His Pro Arg Asn Asp Gly Val Thr Phe Gln Asn Arg Glu Lys
 50                  55                  60

Leu Leu Pro Ala Lys Pro Ser Asp Tyr Tyr Arg Glu Tyr Thr Val Pro
 65                  70                  75                  80

Thr Pro Gly Ser Asp Asp Arg Gly Ala Arg Arg Leu Val Thr Gly Ser
                 85                  90                  95

Ser Asp Glu Val Tyr Tyr Thr Ala Asp His Tyr Glu Ser Phe Val Val
            100                 105                 110

```
Val Asp Val Thr Gly
            115

<210> SEQ ID NO 61
<211> LENGTH: 108
<212> TYPE: PRT
<213> ORGANISM: Saccharopolyspora endophytica

<400> SEQUENCE: 61

Asp Ser Pro Ser Thr Glu Val Pro Gly Ala Ser Gln Ser Gly Leu Gln
1               5                  10                  15

Val Gln Gln Leu Ser Lys Leu Pro Pro Glu Thr Gly Lys Thr Tyr Gln
            20                  25                  30

Leu Ile Val Lys Gly Gly Pro Phe Pro Tyr Pro Gly Lys Asp Gly Ser
        35                  40                  45

Val Phe Gly Asn Arg Glu Gly Glu Leu Pro Glu Gln Lys Ser Gly Tyr
    50                  55                  60

Tyr His Glu Tyr Thr Val Pro Thr Pro Gly Ser Lys Asp Arg Gly Ala
65                  70                  75                  80

Arg Arg Leu Val Thr Gly Gly Gln Asp Glu Val Tyr Tyr Thr Gly Asp
                85                  90                  95

His Tyr Glu Ser Phe Val Val Val Asp Thr Ala Gly
            100                 105

<210> SEQ ID NO 62
<211> LENGTH: 120
<212> TYPE: PRT
<213> ORGANISM: Amycolatopsis circi

<400> SEQUENCE: 62

Ser Asp Ser Pro Ala Pro Ser Ser Ser Gly Ala Pro Ala Ala Ala
1               5                  10                  15

Ser Gly Lys Val Pro Gly Ala Asp Ser Lys Leu Pro Val Lys Pro Leu
            20                  25                  30

Ser Ser Leu Pro Ser Gln Ala Lys Asp Thr Trp Ser Leu Ile His Lys
        35                  40                  45

Gly Gly Pro Tyr Pro Tyr Pro Arg Asn Asp Asp Val Val Phe Gln Asn
    50                  55                  60

Arg Glu Lys Lys Leu Pro Ala Glu Lys Asn Gly Tyr Tyr His Glu Tyr
65                  70                  75                  80

Thr Val Lys Thr Pro Gly Ser Pro Asp Arg Gly Ala Arg Arg Leu Ile
                85                  90                  95

Thr Gly Ala Gly Lys Glu Leu Tyr Tyr Thr Gly Asp His Tyr Ala Ser
            100                 105                 110

Phe Val Val Val Asp Pro Ala Arg
        115                 120

<210> SEQ ID NO 63
<211> LENGTH: 119
<212> TYPE: PRT
<213> ORGANISM: Paenibacillus sp.

<400> SEQUENCE: 63

Leu Ser Val Gly Asp Thr Asn Gln Thr His Ala Val Leu Asn Gln Phe
1               5                  10                  15

Asp Glu Val Ala Asn Tyr Leu Ala Glu His Gln Glu Leu Pro Asp Asn
            20                  25                  30
```

Tyr Ile Thr Lys Lys Glu Ala Arg Ala Leu Gly Trp Glu Pro Ser Glu
            35                  40                  45

Gly Asn Leu Gln Asp Met Ala Pro Gly Lys Ser Ile Gly Gly Asp Ile
 50                  55                  60

Phe Gln Asn Arg Glu Gly Leu Leu Pro Lys Lys Gly Arg Thr Trp
65                  70                  75                  80

Tyr Glu Ala Asp Ile Asn Tyr Ser Gly Gly Thr Arg Gly Ser Asp Arg
                85                  90                  95

Ile Leu Tyr Ser Ser Asp Gly Leu Ile Tyr Lys Thr Thr Asp His Tyr
            100                 105                 110

Arg Thr Phe Glu Gln Ile Lys
        115

<210> SEQ ID NO 64
<211> LENGTH: 117
<212> TYPE: PRT
<213> ORGANISM: Paenibacillus sp.

<400> SEQUENCE: 64

Leu Asp Gln Thr Thr Thr Thr Ala Ser Gln Asp Met Gly Phe Asp Glu
1               5                   10                  15

Val Ala Lys Tyr Ile Ser Glu His Asn Ala Leu Pro Pro Asn Tyr Ile
            20                  25                  30

Thr Lys Lys Glu Ala Arg Ala Leu Gly Trp Glu Pro Ser Glu Gly Asn
        35                  40                  45

Leu Gln Glu Val Ala Pro Gly Lys Ser Ile Gly Gly Asp Val Phe Arg
 50                  55                  60

Asn Arg Glu Gly Leu Leu Pro Asn Lys Lys Gly Arg Thr Trp Tyr Glu
65                  70                  75                  80

Ala Asp Ile His Tyr Ala Gly Gly Arg Gly Ser Asp Arg Ile Leu
                85                  90                  95

Tyr Ser Asn Asp Gly Leu Ile Tyr Lys Thr Thr Asp His Tyr Glu Ser
            100                 105                 110

Phe Glu Gln Leu Lys
        115

<210> SEQ ID NO 65
<211> LENGTH: 156
<212> TYPE: PRT
<213> ORGANISM: Paenibacillus sp.

<400> SEQUENCE: 65

Thr Glu Asn Gln Ser Pro Ala Phe Gln Glu Pro Asn Ser Ser Val Ser
1               5                   10                  15

Asn Ser Ser Pro Thr Glu Gln Pro Gln Pro Ser Pro Ile Pro Thr Asn
            20                  25                  30

Ser Glu Val Gly Glu Asn Val Gln Ala Pro Leu Thr Ser Phe Lys Ala
        35                  40                  45

Val Ser Asp Tyr Ile Arg Glu His His Thr Leu Pro Ala Asn Phe Ile
 50                  55                  60

Thr Lys Lys Glu Ala Glu Gln Leu Gly Trp Val Pro Ala Lys Gly Asn
65                  70                  75                  80

Leu Asp Gln Val Ala Pro Gly Lys Ser Ile Gly Gly Asp Arg Phe Gly
                85                  90                  95

Asn Arg Glu Gly Leu Leu Pro Lys Ala Lys Asn Arg Ile Trp Tyr Glu
            100                 105                 110

Ala Asp Ile Asn Tyr Thr Lys Lys Ser Arg Gly Ala Asp Arg Val Leu
            115                 120                 125

Tyr Ser Asn Asp Gly Leu Ile Tyr Met Thr Thr Asp His Tyr Lys Ser
        130                 135                 140

Phe Thr Asp Ile Thr Lys Glu Gly Ser Val Pro Glu
145                 150                 155

<210> SEQ ID NO 66
<211> LENGTH: 115
<212> TYPE: PRT
<213> ORGANISM: Alkalimonas sp.

<400> SEQUENCE: 66

Gln Pro Ser Val Thr Pro Gly Ala Glu Val Thr Gln Ser Gly Ser Gly
1               5                   10                  15

Ala Gln Pro Arg Met Ser Ala Gln Gln Leu Glu Leu Gln Lys Thr Leu
            20                  25                  30

Gln Arg Ile Gln Gly Asn Gly Pro Phe Pro Tyr Asp Arg Asp Gly Ile
        35                  40                  45

Thr Phe His Asn Arg Glu Arg Leu Leu Pro Ile Lys Pro Arg Gly Tyr
    50                  55                  60

Tyr Arg Glu Tyr Thr Val Asp Thr Pro Gly Leu Ser His Arg Gly Pro
65                  70                  75                  80

Arg Arg Val Val Thr Gly Gly Asn Pro Val Val Phe Tyr Tyr Thr
                85                  90                  95

Glu Asp His Tyr Gln Ser Phe Arg Arg Ile Ser Gly Asp Pro Tyr Glu
            100                 105                 110

Arg Ile His
    115

<210> SEQ ID NO 67
<211> LENGTH: 108
<212> TYPE: PRT
<213> ORGANISM: Nonomuraea dietziae

<400> SEQUENCE: 67

Ala Leu Pro Glu Glu Ser Arg Ala Ala Pro Pro Ala Ala Leu Pro
1               5                   10                  15

Glu Lys Ala Leu Ser Ala Leu Pro Pro Glu Ala Ala Lys Thr Trp Arg
            20                  25                  30

Leu Ile Gln Ser Asp Gly Pro Phe Pro Tyr Arg Arg Asp Gly Val Val
        35                  40                  45

Phe Gln Asn Arg Glu Arg Ile Leu Pro Gln Gln Lys Arg Gly Tyr Tyr
    50                  55                  60

His Glu Tyr Thr Val Pro Thr Pro Gly Ser Arg Asp Arg Gly Ala Arg
65                  70                  75                  80

Arg Leu Val Thr Gly Thr Gly Val Asp Glu Leu Tyr Tyr Thr Gly Asp
                85                  90                  95

His Tyr Arg Ser Phe Val Ala Val Asp Val Lys Arg
            100                 105

<210> SEQ ID NO 68
<211> LENGTH: 462
<212> TYPE: DNA
<213> ORGANISM: Trichoderma harzianum
<220> FEATURE:
<221> NAME/KEY: CDS
<222> LOCATION: (1)..(283)
<220> FEATURE:

```
<221> NAME/KEY: sig_peptide
<222> LOCATION: (1)..(45)
<220> FEATURE:
<221> NAME/KEY: mat_peptide
<222> LOCATION: (46)..(459)
<220> FEATURE:
<221> NAME/KEY: CDS
<222> LOCATION: (350)..(459)

<400> SEQUENCE: 68
```

| | | | | | | | | | | | | | | | | |
|---|---|---|---|---|---|---|---|---|---|---|---|---|---|---|---|---|
| atg | aag | ttc | ctc | ggt | ctc | ctc | tcc | ctc | atc | gcc | ttt | gcc | agc | gcc | gct | 48 |
| Met | Lys | Phe | Leu | Gly | Leu | Leu | Ser | Leu | Ile | Ala | Phe | Ala | Ser | Ala | Ala | |
| -15 | | | | -10 | | | | | -5 | | | | | -1 | 1 | |

| | | | | | | | | | | | | | | | | |
|---|---|---|---|---|---|---|---|---|---|---|---|---|---|---|---|---|
| ccc | ttg | gat | gag | ctc | acc | aag | aga | gac | act | gcc | acc | tgc | ggt | aag | gtc | 96 |
| Pro | Leu | Asp | Glu | Leu | Thr | Lys | Arg | Asp | Thr | Ala | Thr | Cys | Gly | Lys | Val | |
| | | | 5 | | | | | 10 | | | | | 15 | | | |

| | | | | | | | | | | | | | | | | |
|---|---|---|---|---|---|---|---|---|---|---|---|---|---|---|---|---|
| ttc | tat | agc | gcc | agt | gcc | gtt | agt | gcc | gcg | tcc | aac | gcc | gcc | tgc | aac | 144 |
| Phe | Tyr | Ser | Ala | Ser | Ala | Val | Ser | Ala | Ala | Ser | Asn | Ala | Ala | Cys | Asn | |
| | | | 20 | | | | | 25 | | | | | 30 | | | |

| | | | | | | | | | | | | | | | | |
|---|---|---|---|---|---|---|---|---|---|---|---|---|---|---|---|---|
| tac | gtc | cgg | gct | ggc | agc | act | gct | gga | ggc | tcg | act | tat | cct | cac | gta | 192 |
| Tyr | Val | Arg | Ala | Gly | Ser | Thr | Ala | Gly | Gly | Ser | Thr | Tyr | Pro | His | Val | |
| | 35 | | | | | 40 | | | | | 45 | | | | | |

| | | | | | | | | | | | | | | | | |
|---|---|---|---|---|---|---|---|---|---|---|---|---|---|---|---|---|
| tac | aac | aac | tac | gag | ggt | ttc | cgt | ttc | aag | ggt | ctt | tct | aaa | ccg | ttt | 240 |
| Tyr | Asn | Asn | Tyr | Glu | Gly | Phe | Arg | Phe | Lys | Gly | Leu | Ser | Lys | Pro | Phe | |
| 50 | | | | | 55 | | | | | 60 | | | | | 65 | |

| | | | | | | | | | | | | | | |
|---|---|---|---|---|---|---|---|---|---|---|---|---|---|---|
| tat | gag | ttt | cct | att | ctg | tcc | tcg | ggc | aag | act | tat | act | gga | g | 283 |
| Tyr | Glu | Phe | Pro | Ile | Leu | Ser | Ser | Gly | Lys | Thr | Tyr | Thr | Gly | | |
| | | | 70 | | | | | 75 | | | | | | | |

```
gtgcgtggtt cttgatgttt tcgtatgagt aatgagatgt gagactgact gctgaggatg      343
```

| | | | | | | | | | | | | |
|---|---|---|---|---|---|---|---|---|---|---|---|---|
| agatag | gt | tct | cct | ggg | gct | gat | cgt | gtc | gta | att | aat | ggc | cag | tgc | 390 |
| | | Gly | Ser | Pro | Gly | Ala | Asp | Arg | Val | Val | Ile | Asn | Gly | Gln | Cys |
| | | | 80 | | | | | 85 | | | | | 90 | | |

| | | | | | | | | | | | | | | | | |
|---|---|---|---|---|---|---|---|---|---|---|---|---|---|---|---|---|
| tcg | att | gct | ggt | att | atc | aca | cac | act | ggt | gcc | agt | ggt | aac | gct | ttt | 438 |
| Ser | Ile | Ala | Gly | Ile | Ile | Thr | His | Thr | Gly | Ala | Ser | Gly | Asn | Ala | Phe | |
| 95 | | | | | 100 | | | | | 105 | | | | | | |

| | | | | | | |
|---|---|---|---|---|---|---|
| gtt | gct | tgc | gcc | ggt | act | tct | tag | 462 |
| Val | Ala | Cys | Ala | Gly | Thr | Ser | | |
| 110 | | | | | 115 | | | |

```
<210> SEQ ID NO 69
<211> LENGTH: 131
<212> TYPE: PRT
<213> ORGANISM: Trichoderma harzianum

<400> SEQUENCE: 69
```

| | | | | | | | | | | | | | | | |
|---|---|---|---|---|---|---|---|---|---|---|---|---|---|---|---|
| Met | Lys | Phe | Leu | Gly | Leu | Leu | Ser | Leu | Ile | Ala | Phe | Ala | Ser | Ala | Ala |
| -15 | | | | -10 | | | | | -5 | | | | | -1 | 1 |

| | | | | | | | | | | | | | | | |
|---|---|---|---|---|---|---|---|---|---|---|---|---|---|---|---|
| Pro | Leu | Asp | Glu | Leu | Thr | Lys | Arg | Asp | Thr | Ala | Thr | Cys | Gly | Lys | Val |
| | | | 5 | | | | | 10 | | | | | 15 | | |

| | | | | | | | | | | | | | | | |
|---|---|---|---|---|---|---|---|---|---|---|---|---|---|---|---|
| Phe | Tyr | Ser | Ala | Ser | Ala | Val | Ser | Ala | Ala | Ser | Asn | Ala | Ala | Cys | Asn |
| | | | 20 | | | | | 25 | | | | | 30 | | |

| | | | | | | | | | | | | | | | |
|---|---|---|---|---|---|---|---|---|---|---|---|---|---|---|---|
| Tyr | Val | Arg | Ala | Gly | Ser | Thr | Ala | Gly | Gly | Ser | Thr | Tyr | Pro | His | Val |
| | 35 | | | | | 40 | | | | | 45 | | | | |

| | | | | | | | | | | | | | | | |
|---|---|---|---|---|---|---|---|---|---|---|---|---|---|---|---|
| Tyr | Asn | Asn | Tyr | Glu | Gly | Phe | Arg | Phe | Lys | Gly | Leu | Ser | Lys | Pro | Phe |
| 50 | | | | | 55 | | | | | 60 | | | | | 65 |

| | | | | | | | | | | | | | | | |
|---|---|---|---|---|---|---|---|---|---|---|---|---|---|---|---|
| Tyr | Glu | Phe | Pro | Ile | Leu | Ser | Ser | Gly | Lys | Thr | Tyr | Thr | Gly | Gly | Ser |
| | | | 70 | | | | | 75 | | | | | 80 | | |

| | | | | | | | | | | | | | | | |
|---|---|---|---|---|---|---|---|---|---|---|---|---|---|---|---|
| Pro | Gly | Ala | Asp | Arg | Val | Val | Ile | Asn | Gly | Gln | Cys | Ser | Ile | Ala | Gly |
| | | 85 | | | | | 90 | | | | | 95 | | | |

| | | | | | | | | | | | | | | | |
|---|---|---|---|---|---|---|---|---|---|---|---|---|---|---|---|
| Ile | Ile | Thr | His | Thr | Gly | Ala | Ser | Gly | Asn | Ala | Phe | Val | Ala | Cys | Ala |

```
                100                 105                 110

Gly Thr Ser
    115

<210> SEQ ID NO 70
<211> LENGTH: 530
<212> TYPE: DNA
<213> ORGANISM: Fusarium solani
<220> FEATURE:
<221> NAME/KEY: CDS
<222> LOCATION: (1)..(15)
<220> FEATURE:
<221> NAME/KEY: sig_peptide
<222> LOCATION: (1)..(128)
<220> FEATURE:
<221> NAME/KEY: CDS
<222> LOCATION: (87)..(354)
<220> FEATURE:
<221> NAME/KEY: mat_peptide
<222> LOCATION: (129)..(527)
<220> FEATURE:
<221> NAME/KEY: CDS
<222> LOCATION: (418)..(527)

<400> SEQUENCE: 70 atg ctc ttc ttc aag gtacatcagc ctactcaatc tcatcactgc catacccgtc      55
Met Leu Phe Phe Lys
            -15 tcagcactgg ccttgttgct aacctcttca g tcc ctc gct cct ctg gcc gct      107
                                  Ser Leu Ala Pro Leu Ala Ala
                                                      -10 ctc ctg agc gtt gcc gtc gct ggc ccc atc gag agc cgt cag tct gcc      155
Leu Leu Ser Val Ala Val Ala Gly Pro Ile Glu Ser Arg Gln Ser Ala
     -5              -1   1               5 acc acc tgc ggc aac acc gcc tac tct gct gcc cag gtc cgc gcc gct      203
Thr Thr Cys Gly Asn Thr Ala Tyr Ser Ala Ala Gln Val Arg Ala Ala
 10                  15                  20                  25 gcc aac gct gct tgc tcc tac tac cga gcg gat gac act gcc ggt agc      251
Ala Asn Ala Ala Cys Ser Tyr Tyr Arg Ala Asp Asp Thr Ala Gly Ser
             30                  35                  40 tcg acc tac cct cac acc ttc aac aac cgt gag ggc ttc gac ttc ctc      299
Ser Thr Tyr Pro His Thr Phe Asn Asn Arg Glu Gly Phe Asp Phe Leu
     45                  50                  55 gtc agt ggc ccc tac cag gag ttt ccc atc agg tcc agc ggt gtc tac      347
Val Ser Gly Pro Tyr Gln Glu Phe Pro Ile Arg Ser Ser Gly Val Tyr
 60                  65                  70 act ggt g gtatgttctc agataccctt tcctcgtgcc tcgacttgta gtctccgact     404
Thr Gly
    75 aatcccttta tag gc tcc cct ggc gct gac cgt gtt gtc atc aac acc       452
                Gly Ser Pro Gly Ala Asp Arg Val Val Ile Asn Thr
                                     80                  85 agc tgc cag tat gct ggt gcc atc acc cac act gga gct tct ggc aac      500
Ser Cys Gln Tyr Ala Gly Ala Ile Thr His Thr Gly Ala Ser Gly Asn
         90                  95                 100 aac ttt gtt ggc tgc tcg ggc acc aac tag                              530
Asn Phe Val Gly Cys Ser Gly Thr Asn
    105                 110

<210> SEQ ID NO 71
<211> LENGTH: 131
<212> TYPE: PRT
<213> ORGANISM: Fusarium solani

<400> SEQUENCE: 71
```

-continued

```
Met Leu Phe Phe Lys Ser Leu Ala Pro Leu Ala Ala Leu Leu Ser Val
            -15                 -10                 -5

Ala Val Ala Gly Pro Ile Glu Ser Arg Gln Ser Ala Thr Thr Cys Gly
        -1   1               5                   10

Asn Thr Ala Tyr Ser Ala Ala Gln Val Arg Ala Ala Asn Ala Ala
            15                  20                  25

Cys Ser Tyr Tyr Arg Ala Asp Asp Thr Ala Gly Ser Ser Thr Tyr Pro
30                  35                  40                  45

His Thr Phe Asn Asn Arg Glu Gly Phe Asp Phe Leu Val Ser Gly Pro
                50                  55                  60

Tyr Gln Glu Phe Pro Ile Arg Ser Gly Val Tyr Thr Gly Gly Ser
                65                  70                  75

Pro Gly Ala Asp Arg Val Val Ile Asn Thr Ser Cys Gln Tyr Ala Gly
            80                  85                  90

Ala Ile Thr His Thr Gly Ala Ser Gly Asn Asn Phe Val Gly Cys Ser
            95                  100                 105

Gly Thr Asn
110

<210> SEQ ID NO 72
<211> LENGTH: 116
<212> TYPE: PRT
<213> ORGANISM: Trichoderma harzianum

<400> SEQUENCE: 72

Ala Pro Leu Asp Glu Leu Thr Lys Arg Asp Thr Ala Thr Cys Gly Lys
1               5                   10                  15

Val Phe Tyr Ser Ala Ser Ala Val Ser Ala Ala Ser Asn Ala Ala Cys
                20                  25                  30

Asn Tyr Val Arg Ala Gly Ser Thr Ala Gly Gly Ser Thr Tyr Pro His
            35                  40                  45

Val Tyr Asn Asn Tyr Glu Gly Phe Arg Phe Lys Gly Leu Ser Lys Pro
    50                  55                  60

Phe Tyr Glu Phe Pro Ile Leu Ser Ser Gly Lys Thr Tyr Thr Gly Gly
65                  70                  75                  80

Ser Pro Gly Ala Asp Arg Val Val Ile Asn Gly Gln Cys Ser Ile Ala
                85                  90                  95

Gly Ile Ile Thr His Thr Gly Ala Ser Gly Asn Ala Phe Val Ala Cys
            100                 105                 110

Ala Gly Thr Ser
        115

<210> SEQ ID NO 73
<211> LENGTH: 112
<212> TYPE: PRT
<213> ORGANISM: Fusarium solani

<400> SEQUENCE: 73

Gly Pro Ile Glu Ser Arg Gln Ser Ala Thr Thr Cys Gly Asn Thr Ala
1               5                   10                  15

Tyr Ser Ala Ala Gln Val Arg Ala Ala Asn Ala Ala Cys Ser Tyr
            20                  25                  30

Tyr Arg Ala Asp Asp Thr Ala Gly Ser Ser Thr Tyr Pro His Thr Phe
            35                  40                  45

Asn Asn Arg Glu Gly Phe Asp Phe Leu Val Ser Gly Pro Tyr Gln Glu
            50                  55                  60
```

```
Phe Pro Ile Arg Ser Ser Gly Val Tyr Thr Gly Gly Ser Pro Gly Ala
 65                  70                  75                  80

Asp Arg Val Val Ile Asn Thr Ser Cys Gln Tyr Ala Gly Ala Ile Thr
                 85                  90                  95

His Thr Gly Ala Ser Gly Asn Asn Phe Val Gly Cys Ser Gly Thr Asn
            100                 105                 110
```

<210> SEQ ID NO 74
<211> LENGTH: 43
<212> TYPE: DNA
<213> ORGANISM: Artificial sequence
<220> FEATURE:
<223> OTHER INFORMATION: Primer

<400> SEQUENCE: 74
acacaactgg ggatccacca tgaagttcct cggtctcctc tcc           43

<210> SEQ ID NO 75
<211> LENGTH: 40
<212> TYPE: DNA
<213> ORGANISM: Artificial sequence
<220> FEATURE:
<223> OTHER INFORMATION: Primer

<400> SEQUENCE: 75
agatctcgag aagcttacta agaagtaccg gcgcaagcaa               40

<210> SEQ ID NO 76
<211> LENGTH: 141
<212> TYPE: PRT
<213> ORGANISM: Streptomyces aureofaciens

<400> SEQUENCE: 76

```
Met Arg Ile Pro Pro Arg Leu Val Ala Leu Ala Gly Ala Ala Ala Val
  1               5                  10                  15

Ala Ala Thr Leu Ile Ala Gly Pro Val Ala Ala Ala Pro Ala Ser
                 20                  25                  30

His Ala Val Ala Ala Ser Ser Ala Ala Ser Ala Ser Val Lys Ala Val
             35                  40                  45

Gly Arg Val Cys Tyr Ser Ala Leu Pro Ser Gln Ala His Asp Thr Leu
 50                  55                  60

Asp Leu Ile Asp Glu Gly Gly Pro Phe Pro Tyr Ser Gln Asp Gly Val
 65                  70                  75                  80

Val Phe Gln Asn Arg Glu Gly Leu Leu Pro Ala His Ser Thr Gly Tyr
                 85                  90                  95

Tyr His Glu Tyr Thr Val Ile Thr Pro Gly Ser Pro Thr Arg Gly Ala
            100                 105                 110

Arg Arg Ile Ile Thr Gly Gln Gln Trp Gln Glu Asp Tyr Tyr Thr Ala
            115                 120                 125

Asp His Tyr Ala Ser Phe Arg Arg Val Asp Phe Ala Cys
            130                 135                 140
```

<210> SEQ ID NO 77
<211> LENGTH: 131
<212> TYPE: PRT
<213> ORGANISM: Gibberella fujikuroi

<400> SEQUENCE: 77

```
Met Leu Phe Phe Lys Ser Ile Ala Ser Leu Ala Ala Leu Val Ser Leu
  1               5                  10                  15
```

```
Ala Val Ala Ser Pro Ile Glu Ser Arg Gln Ser Ala Thr Thr Cys Gly
            20                  25                  30

Ser Thr Asn Tyr Ser Ala Ser Gln Val Arg Ala Ala Asn Ala Ala
        35                  40                  45

Cys Gln Tyr Tyr Gln Asn Asp Asp Thr Ala Gly Ser Ser Thr Tyr Pro
 50                  55                  60

His Thr Tyr Asn Asn Tyr Glu Gly Phe Asp Phe Pro Val Asp Gly Pro
 65                  70                  75                  80

Tyr Gln Glu Phe Pro Ile Lys Ser Gly Gly Val Tyr Thr Gly Gly Ser
            85                  90                  95

Pro Gly Ala Asp Arg Val Val Ile Asn Thr Asn Cys Glu Tyr Ala Gly
            100                 105                 110

Ala Ile Thr His Thr Gly Ala Ser Gly Asn Asn Phe Val Gly Cys Ser
            115                 120                 125

Gly Thr Asn
    130

<210> SEQ ID NO 78
<211> LENGTH: 18
<212> TYPE: PRT
<213> ORGANISM: Artificial sequence
<220> FEATURE:
<223> OTHER INFORMATION: Motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 78

Tyr Xaa Glu Tyr Thr Val Xaa Thr Pro Xaa Xaa Xaa Xaa Arg Gly Xaa
 1               5                   10                  15

Arg Arg

<210> SEQ ID NO 79
<211> LENGTH: 6
<212> TYPE: PRT
<213> ORGANISM: Artificial sequence
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X = W(Trp) or Y(Tyr)
<220> FEATURE:
<221> NAME/KEY: MISC_FEATURE
<222> LOCATION: (2)..(2)
<223> OTHER INFORMATION: X = Y(Tyr), R(Arg) or F(Phe)
<220> FEATURE:
<221> NAME/KEY: MISC_FEATURE
<222> LOCATION: (4)..(4)
<223> OTHER INFORMATION: X = A(Ala), Y(Tyr), F(Phe), W(Trp) or C(Cys)
<220> FEATURE:
<221> NAME/KEY: MISC_FEATURE
<222> LOCATION: (6)..(6)
<223> OTHER INFORMATION: X = I(Ile) or V(Val)
```

```
<400> SEQUENCE: 79

Xaa Xaa Glu Xaa Asp Xaa
1               5

<210> SEQ ID NO 80
<211> LENGTH: 11
<212> TYPE: PRT
<213> ORGANISM: Artificial sequence
<220> FEATURE:
<223> OTHER INFORMATION: Motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 80

Gly Xaa Xaa Ile Gly Gly Asp Xaa Phe Xaa Asn
1               5                   10

<210> SEQ ID NO 81
<211> LENGTH: 9
<212> TYPE: PRT
<213> ORGANISM: Artificial sequence
<220> FEATURE:
<223> OTHER INFORMATION: Motif
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: X = Y(Tyr), F(Phe) or A(Ala)
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: X = N(Asn) or D(Asp)
<220> FEATURE:
<221> NAME/KEY: misc_feature
<222> LOCATION: (8)..(8)
<223> OTHER INFORMATION: Xaa can be any naturally occurring amino acid

<400> SEQUENCE: 81

Tyr Pro His Xaa Xaa Xaa Xaa Xaa Glu
1               5

<210> SEQ ID NO 82
<211> LENGTH: 6
<212> TYPE: PRT
<213> ORGANISM: Artificial sequence
<220> FEATURE:
<223> OTHER INFORMATION: Motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 82

Pro Gly Xaa Asp Arg Val
```

```
<210> SEQ ID NO 83
<211> LENGTH: 8
<212> TYPE: PRT
<213> ORGANISM: Artificial sequence
<220> FEATURE:
<223> OTHER INFORMATION: Motif
<220> FEATURE:
<221> NAME/KEY: MISC_FEATURE
<222> LOCATION: (6)..(6)
<223> OTHER INFORMATION: X = S(Ser) or R(Arg)
<220> FEATURE:
<221> NAME/KEY: misc_feature
<222> LOCATION: (7)..(7)
<223> OTHER INFORMATION: Xaa can be any naturally occurring amino acid

<400> SEQUENCE: 83

Ile Thr His Thr Gly Ala Xaa Gly
1               5
```